United States Patent
Hamon et al.

(10) Patent No.: US 12,103,927 B2
(45) Date of Patent: Oct. 1, 2024

(54) PYCLEN-BASED MACROCYCLIC LIGANDS, CHELATES THEREOF AND USES THEREOF

(71) Applicants: CENTRE NATIONAL DE LA RECHERCHE SCIENTIFIQUE, Paris (FR); ÉCOLE NORMALE SUPÉRIEURE DE LYON, Lyons (FR); UNIVERSITÉ CLAUDE BERNARD LYON 1 (UCBL1), Villeurbanne (FR); UNIVERSITÉ DE BRETAGNE OCCIDENTALE, Brest (FR)

(72) Inventors: Nadège Hamon, Brest (FR); Maryline Beyler, Brest (FR); Raphaël Tripier, Kersaint-Plabennec (FR); Olivier Maury, Brindas (FR); Janah Shaya, Lyons (FR)

(73) Assignees: CENTRE NATIONAL DE LA RECHERCHE SCIENTIFIQUE, Paris (FR); ÉCOLE NORMALE SUPÉRIEURE DE LYON, Lyons (FR); UNIVERSITÉ CLAUDE BERNARD LYON 1 (UCBL1), Villeurbanne (FR); UNIVERSITÉ DE BRETAGNE OCCIDENTALE, Brest (FR)

( * ) Notice: Subject to any disclaimer, the term of this patent is extended or adjusted under 35 U.S.C. 154(b) by 0 days.

(21) Appl. No.: 17/042,408

(22) PCT Filed: Mar. 29, 2019

(86) PCT No.: PCT/EP2019/058066
§ 371 (c)(1),
(2) Date: Sep. 28, 2020

(87) PCT Pub. No.: WO2019/185901
PCT Pub. Date: Oct. 3, 2019

(65) Prior Publication Data
US 2021/0017180 A1 Jan. 21, 2021

(30) Foreign Application Priority Data
Mar. 30, 2018 (EP) .................................... 18305380

(51) Int. Cl.
C07D 471/08 (2006.01)
A61K 49/00 (2006.01)

(52) U.S. Cl.
CPC ........ C07D 471/08 (2013.01); A61K 49/0021 (2013.01)

(58) Field of Classification Search
CPC ............ A61K 49/0019; A61K 49/0021; A61K 51/0482; C07D 471/08
See application file for complete search history.

(56) References Cited

U.S. PATENT DOCUMENTS

2016/0031910 A1  2/2016 Maury et al.

FOREIGN PATENT DOCUMENTS

WO  2013/011236 A1  1/2013
WO  2014162105 A1  10/2014
(Continued)

OTHER PUBLICATIONS

Le Fur et al. "Stable and Inert Yttrium (III) Complexes with Pyclen-Based Ligands Bearing Pendant Picolinate Arms: Toward New Pharmaceuticals for beta-Radiotherapy." Inorganic Chemistry, Feb. 2018, vol. 57, No. 4, pp. 2051-2063.
(Continued)

Primary Examiner — Michael G. Hartley
Assistant Examiner — Leah H Schlientz
(74) Attorney, Agent, or Firm — Maier & Maier, PLLC

(57) ABSTRACT

A ligand of Formula (A):

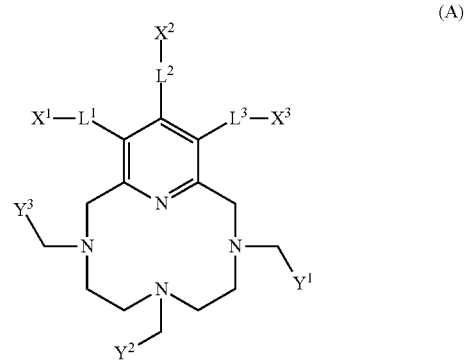

or a carboxylate salt thereof; wherein $Y^1$, $Y^2$ and $Y^3$ each independently represents —COOH or a picolinate of Formula (i):

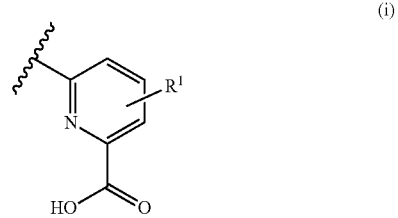

wherein each $R^1$ independently represents a chromophore group; $L^1$, $L^2$ and $L^3$ each independently represents a single bond or a linker; and $X^1$, $X^2$ and $X^3$ each independently represents a hydrogen atom, a coupling function or a biovectorizing group. Also, a process for manufacturing the
(Continued)

ligand and to a process for manufacturing a chelate by complexation by the ligand of a rare-earth cation, preferably a lanthanide cation. Further, a use of the ligand and/or the chelate in biological imaging and/or photoluminescence imaging.

17 Claims, No Drawings

(56) References Cited

FOREIGN PATENT DOCUMENTS

| WO | 2015071334 A1 | 5/2015 |
|---|---|---|
| WO | 2016087667 A1 | 6/2016 |
| WO | 2017/109217 A1 | 6/2017 |

OTHER PUBLICATIONS

D'Alfo et al. "Efficient Sensitization of Europium, Ytterbium, and Neodymium Functionalized Tris-Dipicolinate Lanthanide Complexes through Tunable Charge-Transfer Excited States." Inorganic Chemistry, 2008, vol. 47, No. 22, pp. 10258-10268.
D'Aléo et al. "Design of Dipicolinic Acid Ligands for the Two-Photon Sensitized Luminescence of Europium Complexes with Optimized Cross-Sections." Inorganic Chemistry, 2008, vol. 47, No. 22, pp. 10269-10279.
D'Aléo et al. "Ytterbium-Based Bioprobes for Near-Infrared Two-Photon Scanning Laser Microscopy Imaging." Angewandte Chemie International Edition, 2012, vol. 51, pp. 6622-6625.
Bui et al. "Twisted Charge-Transfer Antennae for Ultra-Bright Terbium (III) and Dysprosium (III) Bioprobes." Chemistry A European Journal, 2018, vol. 24, pp. 3408-3412.
Sy et al. "Spectroscopic Properties of a Family of Mono- to Trinuclear Lanthanide Complexes." European Journal of Inorganic Chemistry, 2017, pp. 2122-2129.
Bui, et al. "Cationic Two-Photon Lanthanide Bioprobes Able to Accumulate in Live Cells." Inorganic Chemistry, 2016, vol. 55, pp. 7020-7025.
Nocton et al. "Water Stability and Luminescence of Lanthanide Complexes of Tripodal Ligands Derived from 1,4,7-Triazacyclononane: Pyridinecarboxamide versus Pyridinecarboxylate Donors." Helvetica Chimica Acta, 2009, vol. 92, pp. 2257-2273.
Walton et al. "Very bright europium complexes that stain cellular mitochondria." Chemical Communications, 2013, vol. 49, No. 16, pp. 1600-1602.
Siaugue et al. "Regioselective synthesis of N-functionalized 12-membered azapyridinomacrocycles bearing trialkylcarboxylic acid side chains." Tetrahedron, 2001, vol. 57, pp. 4713-4718.
Le Fur et al. "Expanding the Family of Pyclen-Based Ligands Bearing Pendant Picolinate Arms for Lanthanide Complexation." Inorganic Chemistry, 2018, vol. 57, No. 12, pp. 6932-6945.
Placide et al. "Two-photon multiplexing bio-imaging using a combination of Eu- and Tb-bioprobes." Dalton Transactions, 2015, vol. 44, pp. 4918-4924.
Bui et al. "Terbium(III) Luminescent Complexes as Millisecond-Scale Viscosity Probes for Lifetime Imaging." Journal of American Chemistry Society, 2017, vol. 139, pp. 7693-7696.
Bui et al. "Near infrared two photon imaging using a bright cationic Yb(III) bioprobe spontaneously internalized into live cells." Chemical Communications, 2017, vol. 53, pp. 6005-6008.
Bui et al. "Unexpected Efficiency of a Luminescent Samarium(III) Complex for Combined Visible and Near-Infrared Biphotonic Microscopy." Chemistry A European Journal, 2015, vol. 21, pp. 17757-17761.
Le Fur et al. "The role of the capping bond effect on pyclen natY3+/90Y3+ chelates: full control of the regiospecific N-functionalization makes the difference." Chemical Communications, Sep. 7, 2017, vol. 53, No. 69, 5 pages.
Le Fur et al. "A Coordination Chemistry Approach to Fine-Tune the Physicochemical Parameters of Lanthanide Complexes Relevant to Medical Applications." Chemistry A European Journal, 2018, vol. 24, pp. 3127-3131.
International Search Report issued on Jun. 5, 2019 in corresponding International application No. PCT/EP2019/058066; 4 pages.
Marine Soulie et al: "Comparative Analysis of Conjugated Alkynyl Chromophore-Triazacyclononane Ligands for Sensitized Emission of Europium and Terbium", Chemistry—A European Journal, vol. 20, No. 28, Jun. 17, 2014 (Jun. 17, 2014) , pp. 8636-8646, 12 pgs.
Adrien Bourdolle et al: "Modulating the Photophysical Properties of Azamacrocyclic Europium Complexes with Charge-Transfer Antenna Chromophores", Inorganic Chemistry, vol. 50, No. 11, Jun. 6, 2011 (Jun. 6, 2011), pp. 4987-4999, 14 pgs.

PYCLEN-BASED MACROCYCLIC LIGANDS, CHELATES THEREOF AND USES THEREOF

FIELD

The present invention relates to macrocyclic ligands, chelates of the ligands with metallic cations, and manufacturing processes thereof.

The present invention also relates to the use of chelates comprising pyclen-based macrocyclic ligands in imaging, preferably by luminescence under one- or two-photons excitation, especially in medical imaging in vivo or in vitro, molecular imaging, cellular imaging and/or bioassays imaging such as fluoro-immunoassays.

BACKGROUND

The use of cationic metals in the form of a chelate comprising a metallic cation and one or more ligands in biological imaging such as cellular imaging is well-known; for example, as tags in bioassays or as optical probes. Chelates of trivalent rare-earth elements such as lanthanide cations ($Ln^{3+}$) have attracted special attention in medical imaging due to their optical properties (e.g., $Eu^{3+}$, $Tb^{3+}$, $Yb^{3+}$, $Sm^{3+}$, $Er^{3+}$, $Nd^{3+}$ or $Dy^{3+}$) and magnetic properties (e.g., $Gd^{3+}$ or $Dy^{3+}$).

A chelate for use in photoluminescence studies in vitro or in vivo should have a sufficiently high brightness (B) at the excitation wavelength (typically ranging from 337 to 405 nm for fluorescence microscopy), which necessitates a high emission quantum yield ($\Phi$) and/or a high molar absorption coefficient ($\varepsilon$) at the excitation wavelength as the brightness is, by definition, the product of the emission quantum yield ($\Phi$) by the molar extinction coefficient ($\varepsilon$) (or by the cross section ($\sigma$) for two-photon absorption).

Moreover, a chelate for use in photoluminescence studies in vitro should preferably have a suitable emission wavelength range, typically comprised between 700 and 900 nm ("near infra-red" or "NIR"), also referred as "therapeutic range". Radiations emitted within this wavelength range pass through the biological tissues, such as for example skin, so that images can be recorded in vivo. Three-dimensional images of a living section of a body can even be obtained by using confocal microscopy. Furthermore, no deleterious effects are caused to cells or tissues traversed by emission in 700-900 nm, contrary to radiations emitted in lower wavelength range, such as for example in 400-600 nm.

Advantageously, the release of the metallic cation in vivo or in biological medium of assay shall be avoided in order to prevent toxicity and/or decrease in imaging quality, so that the ligand shall strongly complex the lanthanide cation. Functionalization of the ligand is also often required to achieve bio-vectorization and/or solubilizing the chelate in the imaging medium, which is typically an aqueous medium. Functionalization may also be used as a means to prevent non-specific interaction with a biomacromolecule, through the inclusion of peripheral fragments in the ligand.

Existing ligands and lanthanide chelates have limitations impairing their use in photoluminescence in vitro or in vivo imaging studies. Some of existing complexes may have for example insufficient complexation strength (e.g. DTPA, EDTA), limited brightness, and/or cannot be easily functionalized (e.g., TACN). Therefore, there is a need for ligands with improved complexation properties, improved brightness and/or which can easily be functionalized.

Pyclen is an azamacrocyclic framework, which incorporates an aromatic pyridine moiety to the 12-memberred macrocyclic unit. Due to its relatively more rigid structure compared to cyclic polyamino-ligands usually used and considering the $sp^2$ character of the pyridinic nitrogen which limits coordination possibilities, pyclen was not considered as a very promising ligand. However, pyclen ligands functionalized with three carboxylate arms, such as PCTA, surprisingly form rather stable complexes with metallic cations such as lanthanide cations, achieving suitable thermodynamic stability and kinetic inertness. Such complexes are rapidly formed (e.g., compared to DOTA).

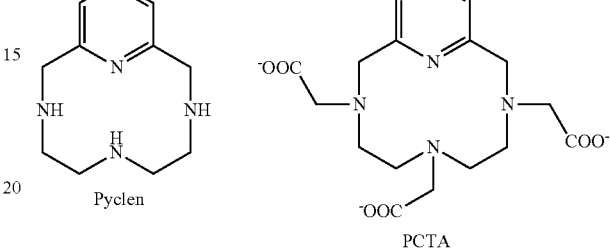

WO 2017/109217 A1 international application is directed to lanthanide chelates and discloses PCTA-based ligands wherein one, two or three carboxylate arms are replaced by a picolinate arm. WO 2017/109217 A1 further discloses that the introduction of picolinate arms improves significantly the ability of the ligands to complex metallic cations such as lanthanide cations, in terms of thermodynamic stability or complexation kinetics. The chelates disclosed therein are presented as useful for radiotherapy purposes by means of the complexation of rare-earth elements including yttrium and lanthanide radioelements.

Le Fur et al. investigated the complexation properties of pyclen-picolinate ligands comprising either one or two picolinate arms (ligands $C_1$-$C_4$ as shown below).

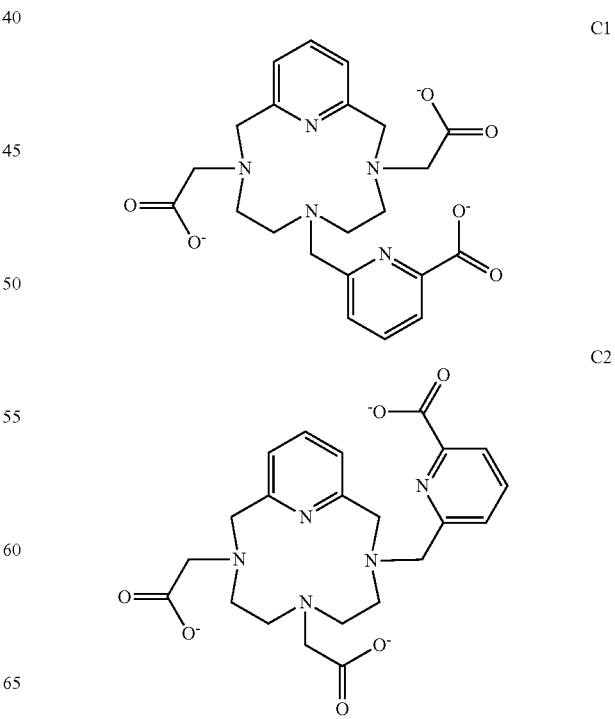

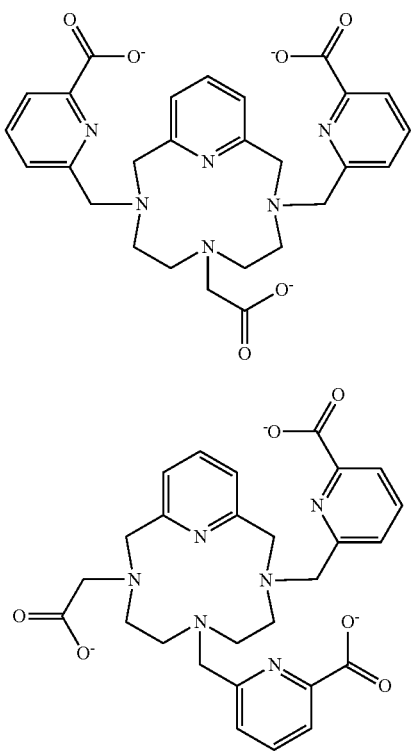

They evidenced that yttrium (III) chelates obtained from ligands C3 and C4, with two picolinate arms present higher thermodynamic stabilities and higher chemical inertness than [Y(C)] and [Y(C2)] chelates. Although both ligands C3 and C4 lead to stable chelates, it was found that the arrangement of picolinate arms around the pyclen cycle is not indifferent, as [Y(C3)] chelate is more labile than [Y(C4)] due to a weaker complexation by the carboxylate group in the former (Le Fur, M. et al., *Inorganic Chemistry* 2018, Vol. 57, No. 4, pp. 2015-2063). However, as yttrium (Y) is not luminescent, such Y(III) complexes are not suitable for photoluminescence imaging studies.

The Applicant was interested in providing lanthanide chelates for use in photoluminescence studies in vivo and considered pyclen-based ligands because of their potent complexing properties. However, when studying the photophysical properties of europium(III) (Eu(III)) complexes of ligands C3 and C4 above, the Applicant found out that although they were of interest for in vitro imaging, they were not suitable for use in photoluminescence imaging in biological medium (in vivo). Indeed, [Eu(C3)] and [Eu(C4)] chelates emitted in a wavelength range of 400-650 nm: they are thus suitable for in vitro imaging, but not for in vivo imaging as their emission wavelength is too low. Moreover, [Eu(C3)] and [Eu(C4)] chelates have a relatively limited molar absorption coefficient (E) at the desired wavelength range (337-405 nm), hence limited brightness, as evidenced in the experimental part of the present application (Example 3-2 below).

Therefore, there remains a need of lanthanide complexes of pyclen-based ligands with improved spectroscopic properties for use in photoluminescence especially for in vitro studies.

Addition of a conjugate "antenna" chromophore group in a picolinate arm of a ligand has been presented as a means of rendering the ligand suitable for carrying out two-photon absorption luminescence (D'Aléo, A. et al., *Inorganic Chemistry*, 2008, Vol. 47, pp. 10258-10268; D'Aléo, A. et al., *Inorganic Chemistry*, 2008, Vol. 47, pp. 10269-10279), thereby shifting the excitation wavelength in the "therapeutic range" (700-900 nm) and, in some cases, also improving the brightness of the metal chelate, as illustrated in the case of TACN-based ligands (D'Aléo, A. et al., *Angewandte Chemie International Edition*, 2012, Vol. 51, pp. 6622-6625; Soulié, F. et al., *Chemistry a European Journal*, 2014, Vol. 20, pp. 8636-8646; Bui, A.-T. et al., *Chemistry a European Journal*, 2018, Vol. 24, pp. 3408-3412; WO 2013/011236 A1, Lamarque, L. et al.; WO 2014/162105 A1, Maury, O. et al.). However, it was equally shown in the art that such modification, even when it is not directly made on the macrocyclic core structure, can decrease the brightness of the complex (*Inorganic Chemistry*, 2011, Vol. 50, pp. 4987-4999; *European Journal of Inorganic Chemistry*, 2017, pp. 2122-2129; *Inorganic Chemistry*, 2016, Vol. 55, pp. 7020-7025; *Helvetica Chimica Acta*, 2009, Vol. 92, pp. 2257-2273). Indeed, the introduction of a chromophore in the structure of the ligand is susceptible to affect its conformation and/or flexibility (e.g., because of steric effects); and/or to alter the repartition of electronic charges within the ligand (e.g., because of groups attracting or repulsing electrons). Consequently, the introduction of a chromophore may have an effect on steric constrains and/or on the electrostatic interactions within the chelate. In other words, although the inclusion of an "antenna" chromophore can be useful for photoluminescence imaging in biological medium, there is a risk of actually losing the luminescence and/or coordination properties. For these reasons, establishing a relationship between the structure and the spectroscopic properties of lanthanide complexes in solution has achieved very limited success; and trying to design lanthanide complexes with predetermined emission properties by means of addition of known chromophores groups to a ligand remains highly hazardous. This is evidenced by comparative data from prior art provided in the experimental part of the present application (Example 3-2 below).

The Applicant carried out in-depth research in order to provide novel pyclen-based ligands and unexpectedly found that lanthanide complexes wherein the ligand is a pyclen substituted by two picolinate arms, both picolinate bearing an arylalkyne- or alkoxyaryl-based chromophore antenna, surprisingly present suitable spectroscopic properties for use in photoluminescence studies, especially presented high brightness.

The lanthanide chelates obtained from the ligands according to the invention provide both potent chelation of the cation and appropriate emission properties. They may emit at the "therapeutic range" (NIR) under two-photon absorption and are thus useful for performing in vivo imagery. The chromophores in the ligands may further comprise hydrophilic groups, thus improving the solubility of the lanthanide chelate in aqueous medium and further limiting non-specific interaction with biomacromolecules. Moreover, the pyridyl unit can be easily functionalized, thus allowing the conjugation of the ligand to an external moiety for bio-vectorization of the lanthanide chelate. Functionalization on the pyridyl is advantageous compared to functionalization on ethylene, because it avoids the creation of an asymmetric carbon (C*).

SUMMARY

The present invention relates to a compound of Formula (A):

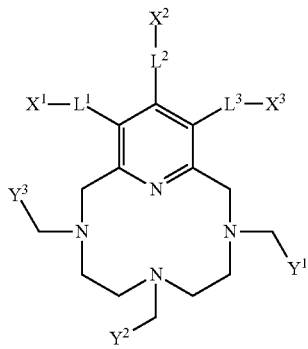

(A)

or a salt thereof, preferably a carboxylate salt thereof;
wherein $Y^1$, $Y^2$ and $Y^3$ each independently represents —COOH or a picolinate of Formula (i):

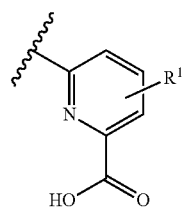

(i)

wherein each $R^1$ independently represents
a chromophore group of Formula (ii):

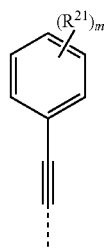

(ii)

wherein m is an integer ranging from 1 to 5, preferably ranging from 1 to 3; and each $R^{21}$ independently represents alkyl, alkoxy, —O-polyether, —S-alkyl, —S-polyether, or —NRR' wherein R represents hydrogen, alkyl, or polyether, and R' represents independently polyether; wherein each $R^{21}$ group is optionally substituted by at least one -$L^{41}$-$Z^{41}$ group;

or a chromophore group of Formula (iii):

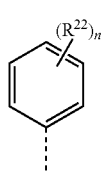

(iii)

wherein n is an integer ranging from 1 to 5, preferably ranging from 1 to 3; and each $R^{22}$ independently represents alkyl, alkoxy, —O-polyether, —S-alkyl, —S-polyether, or —NRR' wherein R represents hydrogen, alkyl, or polyether, and R' represents independently polyether; wherein each $R^{22}$ group is optionally substituted by at least one -$L^{42}$-$Z^{42}$ group;

provided that at least one $R^{22}$ represents alkoxy, —O-polyether, —S-alkyl or —S-polyether;

wherein $L^{41}$ and $L^{42}$ each independently represents a single bond; or a linker selected from alkyl, aryl, arylalkyl, alkylaryl, heteroalkyl, heteroaryl, heteroarylalkyl, alkylheteroaryl, alkenyl and alkynyl; said linker optionally additionally comprising a coupling product through which $R^{21}$ and $R^{22}$ are bounded to $L^{41}$ and $L^{42}$ respectively;

wherein $Z^{41}$ and $Z^{42}$ each independently represents a water-solubilizing group selected from polyethers and betaines;

provided that at least two among $Y^1$, $Y^2$ and $Y^3$ represents a picolinate of Formula (i);

$L^1$, $L^2$ and $L^3$ each independently represents a single bond or a linker selected from alkyl, aryl, arylalkyl, alkylaryl, heteroalkyl, heteroaryl, heteroarylalkyl, alkylheteroaryl, alkenyl and alkynyl; said linker optionally additionally comprising a coupling product through which $X^1$, $X^2$ and $X^3$ are bounded to $L^1$, $L^2$ and $L^3$ respectively;

$X^1$, $X^2$ and $X^3$ each independently represents a hydrogen atom, a coupling function as defined below or a bio-vectorizing group as defined below.

According to one embodiment, the chromophore group of Formula (iii) comprises at least one $R^{22}$ group in ortho-position which represents methyl.

According to one embodiment, the compound is of Formula (B-1) or of Formula (B-2):

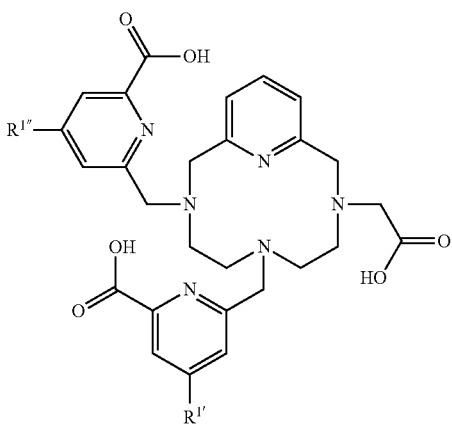

(B-1)

-continued
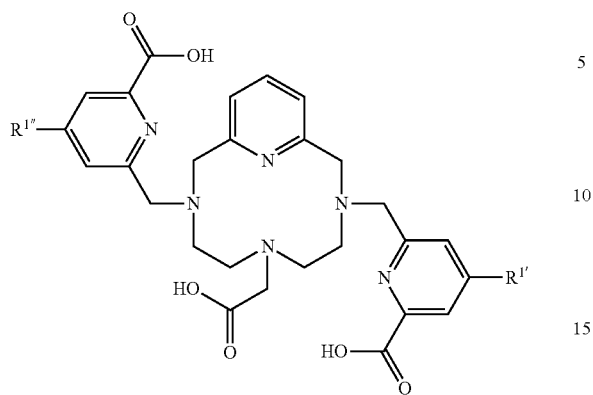
(B-2)
or a carboxylate salt thereof; wherein $R^{1'}$ and $R^{1'''}$ each represents independently $R^1$ as defined in claim 1.
According to one embodiment, the compound is of Formula (C-1) or of Formula (C-2):
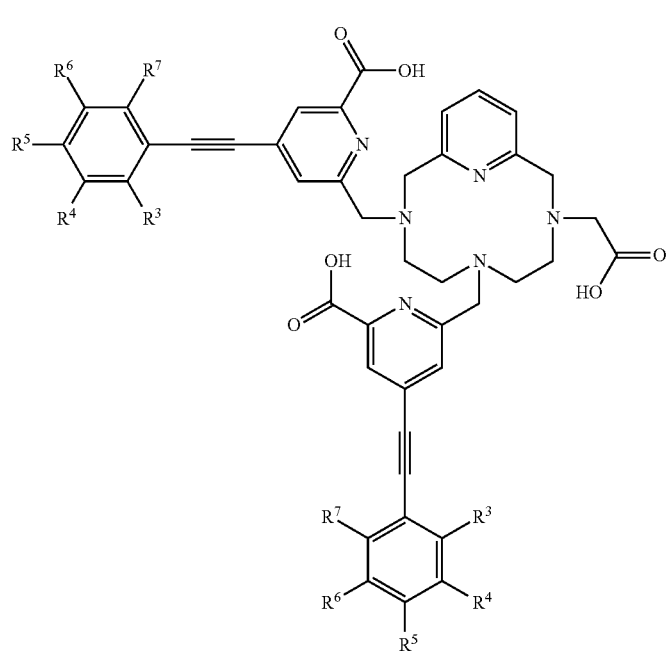
(C-1)
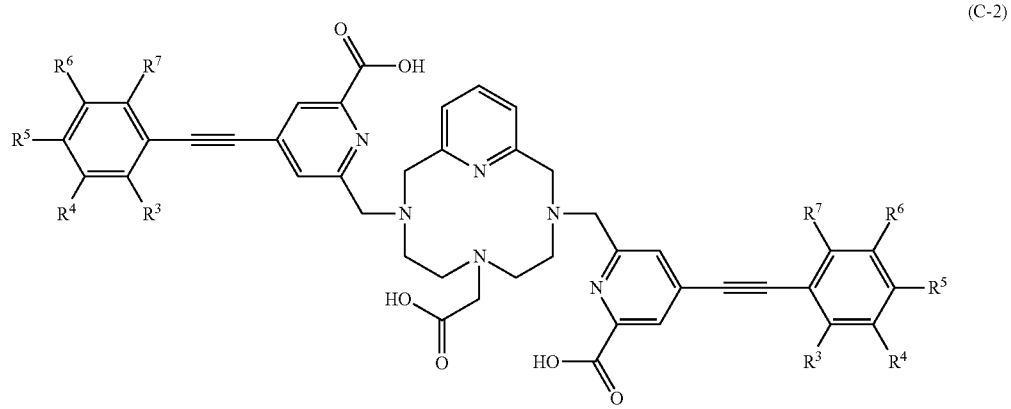
(C-2)
or a carboxylate salt thereof;

wherein $R^3$, $R^4$, $R^5$, $R^6$ and $R^7$ independently represent hydrogen, alkyl, alkoxy, —O-polyether, or —NRR' wherein R and R' represents independently polyether; provided that at least one among $R^3$, $R^4$, $R^5$, $R^6$ and $R^7$ represents —O-polyether or —NRR'.

According to one embodiment, the compound is of Formula (C-3) or of Formula (C-4):

(C-3)

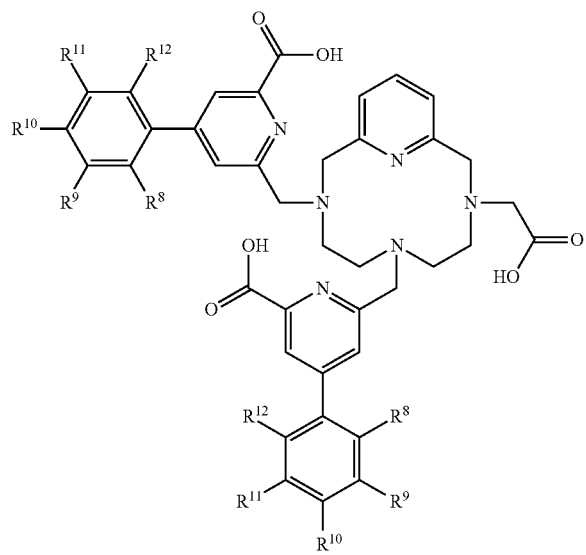

(C-4)

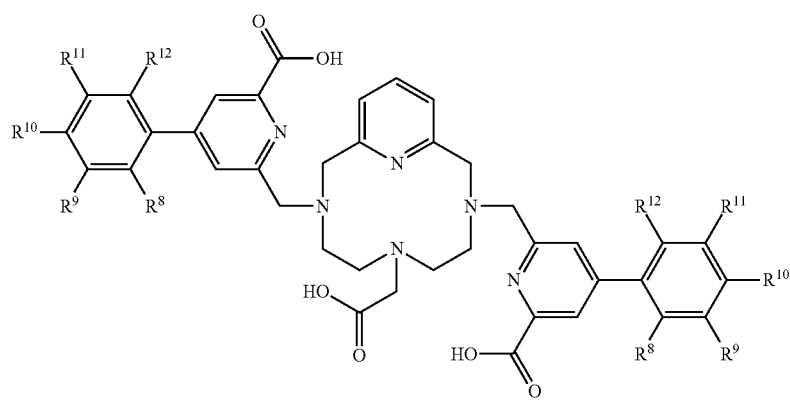

or a carboxylate salt thereof; wherein $R^8$, $R^9$, $R^{10}$, $R^{11}$ and $R^{12}$ independently represent hydrogen, alkyl, alkoxy, or —O-polyether; provided that at least one among $R^8$, $R^9$, $R^{10}$, $R^{11}$ and $R^{12}$ represents —O-polyether.

According to one embodiment, the compound is a triple potassium carboxylate salt of a compound of Formula (A).

According to one embodiment, the polyether in the chromophore group is a polyethylene glycol (PEG).

According to one embodiment, $L^{41}$ and $L^{42}$ each independently represents a single bond or an alkyl comprising a coupling product which is a triazolyl group through which $R^{21}$ and $R^{22}$ are bounded to $L^{41}$ and $L^{42}$ respectively.

According to one embodiment, $Z^{41}$ and $Z^{42}$ each independently represents a water solubilizing group being a betaine.

According to one embodiment, $L^1$, $L^2$ and $L^3$ each independently represents a single bond; or a linker selected from alkyl, arylalkyl, heteroalkyl, heteroaryl, heteroarylalkyl, alkylheteroaryl, alkenyl and alkynyl; said linker optionally additionally comprising a coupling product through which $X^1$, $X^2$ and $X^3$ are bounded to $L^1$, $L^2$ and $L^3$ respectively.

According to one embodiment, the compound is selected from compounds A1 to A6 represented on claim 10 below and/or on Table 1 below, and carboxylate salts thereof.

The present invention further relates to a chelate resulting from the complexation of a compound according to the invention with a lanthanide cation selected from cerium (III), praseodymium (III), neodymium (III), samarium (III), europium (III), gadolinium (III), terbium (III), dysprosium (III), holmium (III), erbium (III), thulium (III), ytterbium (III) and lutetium (III); preferably selected from neodymium (III), samarium (III), europium (III), terbium (III), dysprosium (III), erbium (III) and ytterbium (III); more preferably europium (III).

The present invention further relates to a pharmaceutical composition comprising the chelate according to the invention, in association with at least one pharmaceutically acceptable excipient.

The present invention further relates to a process for manufacturing a chelate according to the invention comprising a step of contacting a compound according to the invention with a lanthanide cation selected from cerium (III), praseodymium (III), neodymium (III), samarium (III), europium (III), gadolinium (III), terbium (III), dysprosium (III), holmium (III), erbium (III), thulium (III), ytterbium (III), lutetium (III); preferably a lanthanide cation selected from neodymium (III), samarium (III), europium (III), terbium (III), dysprosium (III), erbium (III) and ytterbium (III); more preferably europium (III).

The present invention further relates to the use of a compound according to the invention in the manufacture of a chelate according to the invention.

The present invention further relates to the use of a chelate according to the invention in biological imaging, preferably in medical imaging. The present invention further relates to the use of a chelate according to the invention in fluorescence or phosphorescence microscopy, preferably in Fluorescence Resonance Energy Transfer (FRET).

The present invention further relates to a compound of Formula (E):

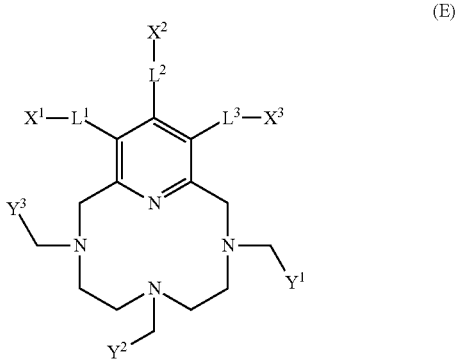

wherein
$Y^1$, $Y^2$ and $Y^3$ each independently represents —$COOR^E$ or a picolinate ester of Formula (i-E):

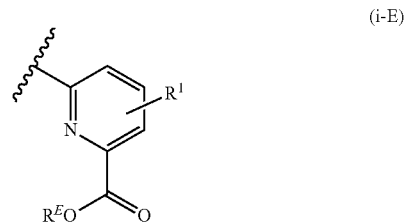

wherein
each $R^E$ independently represents alkyl, preferably methyl or tert-butyl; and
each $R^1$ independently represents a chromophore group of Formula (ii) or a chromophore group of Formula (iii) as defined above;
provided that at least two among $Y^1$, $Y^2$ and $Y^3$ represents a picolinate ester of Formula (i-E); and $L^1$, $L^2$, $L^3$, $X^1$, $X^2$ and $X^3$ are as defined above.

DEFINITIONS

Where chemical substituents are combinations of chemical groups, the point of attachment of the substituent to the molecule is by the last chemical group recited. For example, an arylalkyl substituent is linked to the rest of the molecule through the alkyl moiety and it may be represented as follows: "aryl-alkyl-".

In the present invention, the following terms have the following meanings:

"About" preceding a figure means plus or less 10% of the value of said figure.

"Activating function" refers to a chemical moiety capable to render reactive a chemical function. For example, for a carboxylic acid chemical function, an activating function may be N-hydroxysuccinimide, N-hydroxyglutarimide, maleimide, halide or anhydride moieties.

"Activated carboxylic acid" refers for example to acid anhydride or acyl halide.

"Activated ester" refers to an ester in which the alkoxy group is replaced by an electron-withdrawing group. Examples of activated esters are N-hydroxysuccinimide ester, N-hydroxyglutarimide ester, N-hydroxybenzotriazole ester, maleimide ester or pentafluorophenyl ester.

"Alkene" or "alkenyl" refer to any linear or branched hydrocarbon chain with 2 to 12 carbon atoms, preferably 2 to 6 carbon atoms, having at least one double bond. Examples of alkenyl groups are ethenyl, 2-propenyl, 2-butenyl, 3-butenyl, 2-pentenyl and its isomers, 2-hexenyl and its isomers, or 2,4-pentadienyl.

"Alkoxy" refers to a group of formula —O-alkyl.

"Alkyl" refers to any saturated linear or branched hydrocarbon chain with 1 to 12 carbon atoms, preferably 1 to 6 carbon atoms, and more preferably 1 to 3 carbon atoms. Examples of alkyl groups are methyl, ethyl, n-propyl, i-propyl, n-butyl, i-butyl, s-butyl, t-butyl, pentyl and its isomers (e.g. n-pentyl or i-pentyl), or hexyl and its isomers (e.g., n-hexyl or i-hexyl).

"Alkylaryl" refers to an aryl group substituted by an alkyl group: alkyl-aryl-.

"Alkylheteroaryl" refers to an aryl group substituted by an alkyl group: alkyl-heteroaryl-.

"Alkyne" or "alkynyl" refer to any linear or branched hydrocarbon chain with 2 to 12 carbon atoms, preferably 2 to 6 carbon atoms, having at least one triple bond. Examples of alkynyl groups are ethynyl, 2-propynyl, 2-butynyl, 3-butynyl, 2-pentynyl and its isomers, or 2-hexynyl and its isomers.

"Amine" refers to the group —$NH_2$ and to secondary amines —NHR wherein R is different from hydrogen, preferably wherein R is an alkyl group.

"Aminooxy" refers to a —O—$NH_2$ group.

"Antibody" refers to monoclonal antibodies (mAb), polyclonal antibodies, multispecific antibodies (e.g., bispecific antibodies), hybrid or chimeric antibodies and antibody fragments, so long as they exhibit the desired biological activity. An "antibody fragment" comprises a portion of an intact antibody, preferably the antigen binding or variable region of the intact antibody. Examples of antibody fragments include Fab, Fab', F(ab')2, and Fv fragments; diabodies; linear antibodies; single-chain antibody molecules, especially single-chain variable fragment (scFv); and multispecific antibodies formed from antibody fragments.

"Aryl" refers to a polyunsaturated, aromatic hydrocarbon group with 5 to 12 carbon atoms, preferably 6 to 10 carbon atoms, having a single ring (i.e., phenyl) or multiple aromatic rings fused together (e.g., naphtyl) or linked covalently, wherein at least one ring is aromatic. The aromatic ring may optionally include one to two additional rings (either cycloalkyl, heterocyclyl or heteroaryl) fused thereto. Examples of aryl are phenyl, biphenylyl, biphenylenyl, 5- or 6-tetralinyl, naphthalen-1- or -2-yl, 4-, 5-, 6 or 7-indenyl, 1- 2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

"Arylalkyl" refers to an alkyl group substituted by an aryl group: aryl-alkyl-.

"Betaine" refers to a zwitterionic group of atoms in a molecule; i.e., a group bearing both a positive and a negative electronic charge; wherein the positive charge bearing atom does not carry a hydrogen atom and is not adjacent to the negative charge bearing atom. Typically, betaine groups are linear groups associating (1) one ammonium cation or aromatic iminium and (2) one sulfonate, phosphonate or carboxylate anionic group, and (3) one hydrocarbon chain comprising 1 to 6 carbon atoms spacing the cation and the anion. Preferably, the aromatic iminium group is pyridinium or imidazolium. Preferably, the anionic group is sulfonate. Preferably, the hydrocarbon chain is an alkene chain. Preferably, the hydrocarbon chain comprises 1 to 4 carbon atoms.

"Biological imaging" refers to any imaging method used in biology. Typically, medical imaging comprises a step of analysis of a biological sample by an imaging method. Preferably, the biological sample is obtained from a subject prior to the analysis step.

"Bio-vectorizing group" refers to a molecule being able to recognize a predefined biological target. Preferably, "bio-vectorizing group" are biomolecules, organic compounds or nanocarriers. "Biomolecules" include antibodies, peptides, proteins, lipids, polysaccharide, fatty acid, hapten, liposome, and polyamine; selected to bind biological targets. "Organic compounds" include fluorophores, chromophores and macrocyclic chelates. "Nanocarriers" include solid supports such as nanoparticle or polymeric microparticle, and cationic group suitable for cellular internalization.

Bio-vectorizing groups and biological targets of interest are illustrated by the examples below:

| Group type | Biological target | Group family | Examples of bio-vectorizing group |
|---|---|---|---|
| antibody | CD20 | anti CD20 | Tositumomab (BEXXAR), ibritumumab tiuxetan (Zevalin) Rituximab, Ofatumumab |
| antibody | CEA | anti CEA | IMMU-4, arcitumomab, M5A, T84, 2A3, 2A3-mFc, 9A6 |
| peptide | gastrin-releasing peptide (GRP) receptors | Bombesin, derivatives and analogs of bombesin | PEG4-Bombesin, Bombesin, -[D-Tyr$^6$, βala$^{11}$, Thi$^{13}$, Nle$^{14}$] bombesin, PEG2-[D-Tyr$^6$, βala$^{11}$, Thi$^{13}$, Nle$^{14}$] bombesin, -4-amino-1-carboxymethyl-piperidine-D-Phe-Gln-Trp-Ala-Val-Gly-His-Sta-Leu-NH$_2$, D-Phe-Gln-Trp-Ala-Val-Gly-His-Sta-Leu-NH$_2$, RGD-BBN |
| antibody | HER2 | anti HER2 | ZHER2:342, ZHER2:2891, ZHER2:2395, ZHER2:2891-ABD035 and derivatives thereof, ABY-025, ABY-028 and derivatives thereof |
| antibody | EGFR | anti EGFR | Cetuximab, panitumumab, L19-SIP |
| peptide | somatostatin receptors | somatostatin analogs | OCTREOTIDE, TATE, TOC, octreotate, 1-Nal$^3$-octreotide (NOC), lanreotide, p-Cl-Phe-cyclo(D-Cys-Tyr-D-Aph(Cbm)-Lys-Thr-Cys)D-Tyr-NH$_2$ (LM3), p-NO$_2$-Phe-cyclo(D-Cys-Tyr-D-Aph(Cbm)-Lys-Thr-Cys)D-Tyr-NH$_2$ (JR10), Cpa-cyclo(D-Cys-Tyr-D-Aph(Cbm)-Lys-Thr-Cys)D-Tyr-NH$_2$, pansomatostatin |
| peptide | alphavbeta3 integrin | RGD peptides | Cyclo-RGD, RGD tetramer |
| minibody | PSMA-prostate | Anti-PSMA | HuJ591 minibody |
| mAb | PSMA-prostate | Anti-PSMA | J591, 7E11 |
| small molecule | carboxypeptidase of PSMA | urea-based inhibitors | Lys-urea-Asp sequence and derivatives thereof |
| small molecule | Bones | Bone mineralization | Phosphonates, biphosphonates |
| peptide | cholecystokinin-2 receptors (CCK) | CCK analogs | minigastrin |
| peptide | melanocortin-1 receptor | α-MSH analogs | [Ser-Tyr-Ser-Met-Glu-His-Phe-Arg-Trp-Gly-Lys-Pro-Val]-NH$_2$ |
| small molecules | melanocortin-1 receptor | benzamide derivatives | benzamides derivatives |
| peptide | NK1-receptor-glioblastoma | neuropeptide | P substance |
| peptide | chemokine receptor 4 (CXCR4) | Chemokine analogs | fusine, CD 184, SDF-1a(CXCL12) |
| cationic group | mitochondria | — | Phosphonium moieties |

"Brightness (B)" refers to the amount of radiation emitted by a chromophore or dye. In the case of one-photon absorption, B is defined as the product of the emission quantum yield ($\Phi$) by the molar absorption coefficient ($\varepsilon$), i.e., $B=\varepsilon \cdot \Phi$, at a given excitation wavelength. In the case of two-photon absorption, B is defined as the product of the emission quantum yield ($\Phi$) by the cross section ($\sigma$), i.e., $B=\varepsilon \cdot \sigma$, at a given excitation wavelength.

"Carboxylate ester" refers to an ester of a molecule, said molecule comprising at least one carboxylic acid function (—COOH), wherein the ester is formed by esterification of at least one carboxylic acid function of the molecule. Preferred carboxylic esters are methyl esters. "Mono-ester", "di-ester" and "tri-ester" respectively refers to esters wherein exactly one, two and three carboxylic acid functions have been esterified.

"Carboxylate salt" refers to a salt of a molecule, said molecule comprising at least one carboxylic acid function (—COOH), wherein the salt is formed by deprotonation of at least one carboxylic acid function of the molecule. Preferred carboxylic salts are potassium or sodium salts, more preferably potassium salts. "Mono" salt, "double" salt and "triple" salt respectively refers to salts wherein exactly one, two and three carboxylic acid functions have been deprotonated.

"Chromophore group" refers to a conjugated group of atoms in a molecule which modifies the wavelength range of the radiation absorbed and/or emitted by the molecule; and/or which increases the amount of light absorbed and/or emitted by the molecule. Examples of chromophore groups are provided hereafter.

"Complex" or "chelate" are synonyms and refer to the association of a ligand binding a metal ion. Chelation (or complexation) involves the formation or presence of two or more separate coordinate bonds between a polydentate (multiple bonded) molecule and a single central atom. Polydentate molecules are often organic compounds, and are called ligands, chelants, chelatants, chelators, chelating agents, or sequestering agents. Preferably, the ligand is anionic and forms a chelate with a metallic cation.

"Coupling function" refers to a function capable to react with another function to form a covalent linkage, i.e., is covalently reactive under suitable reaction conditions, and generally represents a point of attachment for another substance. The coupling function is a moiety on the compounds of the present invention that is capable of chemically reacting with a functional group on a different compound to form a covalent linkage. Coupling functions generally include nucleophiles, electrophiles and photoactivable groups. Examples of coupling functions are amine; isothiocyanate; isocyanate; activated ester such as for example N-hydroxysuccinimide ester, N-hydroxyglutarimide ester or maleimide ester; carboxylic acid; activated carboxylic acid such as for example acid anhydride or acid halide; alcohol; alkene, alkyne (e.g., —C≡CH); halide; azide; siloxy; phosphonic acid; thiol; tetrazine; norbornen; oxoamine; aminooxy; thioether; haloacetamide (i.e., —NH—C(O) $CH_2X$ moiety wherein X is an halogen atom) such as for example chloroacetamide, bromoacetamide or iodoacetamide; glutamate; glutaric anhydride, succinic anhydride, maleic anhydride; aldehyde; ketone; hydrazide; chloroformate and maleimide.

"Coupling product" refers to the residue of a coupling function resulting from the reaction between two coupling functions, for example a functionally related group of atoms (such as amide —C(O)—NH— group) or a heterocycle (such as triazolyl group).

For example, reaction between two coupling functions A and B may lead to the following coupling products:

| Coupling function A | Coupling function B | Coupling product |
|---|---|---|
| R-N$_3$ | R-C ≡ CH | triazolyl group |
| R-NH$_2$ | R'-COOH | R-NH(C = O)-R' |
| R-SH | R'-SH | R-SS-R' |
| R-OH | R'-(epoxide group) | R-OCH$_2$CH(OH)-R' |
| R-NH$_2$ | R'-(epoxide group) | R-NHCH$_2$CH(OH)-R' |
| R-SH | R'-(epoxide group) | R-SCH$_2$CH(OH)-R' |
| R-NH$_2$ | R'-CHO | R-N = CH-R' |
| R-NH$_2$ | R'-NCO | R-NH(C = O)NH-R |
| R-NH$_2$ | R'-NCS | R-NH(C = S)NH-R' |
| R-SH | R'-(C = O)CH$_3$ | R-(C = O)CH$_2$S-R' |
| R-SH | R'-O(C = O)X | R-S(C = O)O-R' |
| R-CH = CH$_2$ | R'-SH | R-CH$_2$CH$_2$S-R' |
| R-OH | R'-NCO | R-O(C = O)NH-R' |
| R-SH | R'-(C = O)CH$_2$X | R-SCH$_2$(C = O)-R' |
| R-NH$_2$ | R'-(C = O)N$_3$ | R-NH(C = O)-R' |
| R-COOH | R'-COOH | R-(C = O)O(C = O)-R' |
| R-SH | R'-X | R-S-R' |
| R-NH$_2$ | R-CH$_2$C(NH$^{2+}$)OCH$_3$ | R-NHC(NH$^{2+}$)CH$_2$-R' |
| R-NHNH$_2$ | R'-CHO | R-NHNH = CH-R' | wherein X represents a halogen atom.

"Cross section ($\sigma$)" refers to a measure of the light absorbing capacity of a chromophore or dye in the case of two-photon absorption.

"Emission quantum yield ($\Phi$)" refers to the ratio between the number of photons emitted by a chromophore or dye and the number of photons absorbed by the chromophore or dye.

"Fatty acid" refers to a carboxylic acid with along aliphatic tail (chain), such as, for example, from 4 to 36 atoms of carbon, which is either saturated or unsaturated.

"Halide" refers to a fluorine, chlorine, bromine or iodine atom; preferably a chlorine or bromine atom.

"Hapten" refers to a small molecule that can elicit an immune response only when attached to a large carrier. Examples of haptens are those disclosed in FR 2697255 A1 (Gruaz-Guyon et al.) and US 2012/0282178 A1 (McBride et al.), especially haptens listed in the claims thereof.

"Heteroalkyl" refers to an alkyl group as defined hereinabove wherein one or more carbon atoms are replaced by a heteroatom selected from oxygen, nitrogen and sulphur atoms. In heteroalkyl groups, the heteroatoms are bond along the alkyl chain only to carbon atoms, i.e., each heteroatom is separated from any other heteroatom by at least one carbon atom. However, the nitrogen and sulfur heteroatoms may optionally be oxidized and the nitrogen heteroatoms may optionally be quaternized. An heteroalkyl is bond to another group or molecule only through a carbon atom, i.e., the bounding atom is not selected among the heteroatoms included in the heteroalkyl group.

"Heteroaryl" refers to aromatic rings or aromatic ring systems with 5 to 12 carbon atoms, preferably 6 to 10 carbon atoms, having one or two rings which are fused together or linked covalently, wherein at least one ring is aromatic, and wherein one or more carbon atoms in one or more of these rings is replaced by oxygen, nitrogen and/or sulfur atoms, wherein the nitrogen and sulfur heteroatoms may optionally be oxidized and the nitrogen heteroatoms may optionally be quaternized. Such rings may be fused to an aryl, cycloalkyl, heteroaryl or heterocyclyl ring. Examples of heteroaryl are furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2, 1-b] [1,3] thiazolyl or thieno [3,2-b] furanyl.

"Heteroarylalkyl" refers to an alkyl group substituted by an aryl group: heteroaryl-alkyl-.

"Ketone" refers to a functional group with the connectivity C—(C=O)—C.

"Imaging" refers to any method of analysis which creates a representation or a reproduction of the form of an object such as for example cells or tissues; especially a visual representation (i.e., the formation of an image).

'Leaving group" refers to a molecular fragment that departs from a molecule with a pair of electrons in heterolytic bond cleavage. Typically, a leaving group is an anion or a neutral molecule, preferably an anion. Examples of leaving groups are sulfonate esters such as tosylate (Ts) or mesylate (Ms).

"Lifetime ($\tau$)" or "luminescence lifetime ($\tau$)" refers to the average time a chromophore or dye stays in its excited state before emitting a photon.

"Ligand" or "chelator" or "chelating agent" are synonyms and refer to a polydentate molecule able to form coordination bonds with a metal ion to give a chelate. Preferably, the ligand is anionic.

"Linker" refers to a single covalent bond or to a moiety comprising series of stable covalent bonds, the moiety often incorporating 1-40 plural valent atoms selected from the group consisting of C, N, O, S and P, that covalently attach a coupling function or a bio-vectorizing group to the ligand of the invention. The number of plural valent atoms in a linker may be, for example, 0, 1, 2, 3, 4, 5, 6, 7, 8, 9, 10, 20, 25 or 30. A linker may be linear or non-linear; some linkers have pendant side chains or pendant functional groups (or both). Examples of such pendant moieties are water-solubilizing groups such as sulfo (—SO$_3$H or —SO$_3^-$) or carboxylate (—COO$^-$). In one embodiment, a linker is composed of any combination of single, double, triple or aromatic carbon-carbon bonds, carbon-nitrogen bonds, nitrogen-nitrogen bonds, carbon-oxygen bonds and carbon-sulfur bonds. Linkers may by way of example consist of a combination of moieties selected from alkyl, —C(O)NH—, —C(O)O—, —NH—, —S—, —O—, —C(O)—, —S(O)$_n$— where n is 0, 1 or 2; 5- or 6-membered monocyclic rings and optional pendant functional groups, for example sulfo, hydroxy or carboxy.

In the compounds according to the invention, a coupling function may be reacted with a substance reactive therewith, whereby the linker becomes bonded to a bio-vectorizing group or to a water-solubilizing group. In this case, the linker contains a coupling product resulting from the coupling reaction, such as for example the carbonyl group of an ester; the triazolo group resulting from a click reaction between an azide and an alkyne; or the —NHC(=S)NH— group resulting from the coupling of an amine on an isothiocyanate function.

"Liposome" refers to an artificial vesicle formed by concentric lipid bilayers, trapping therebetween aqueous compartments. A wide variety of amphiphilic lipids can be used to form liposomes, the most commonly used are the phospholipids.

"Lipid" refers to hydrophobic or amphiphilic small molecules, which are naturally occurring and include fats, waxes, sterols, fat-soluble vitamins (such as vitamins A, D, E, and K), monoglycerides, diglycerides, triglycerides and phospholipids. Lipids may be divided into eight categories: fatty acids, glycerolipids, glycerophospholipids, sphingolipids, saccharolipids, polyketides (derived from condensation of ketoacyl subunits); sterol lipids and prenol lipids (derived from condensation of isoprene subunits).

"Molar absorptivity (s)" or "molar absorption coefficient (s)" or "molecular extinction coefficient (s)" are synonyms and refer to a measure of the light absorbing capacity of a chromophore or dye in the case of one-photon absorption.

"Oil-solubilizing group" refers to a group of atoms in a molecule which increase the lipophilic character of the molecule, and especially which increases the solubility of the molecule in oily media. Examples of oil-solubilizing groups are alkyl and alkenyl groups.

"Oxoamine" refers to a —(C=O)—NH$_2$ group.

"Peptide" refers to a linear polymer of amino acids of less than 50 amino acids linked together by peptide bonds.

"Pharmaceutically acceptable" means that the ingredients of a pharmaceutical composition are compatible with each other and not deleterious to the patient thereof.

"Polyether" or "PE" refers to a group of formula -(alkyl$^1$-O)$_x$-alkyl$^2$; wherein x is an integer ranging from 2 to 20, preferably ranging from 2 to 10, more preferably ranging from 3 to 5; and wherein alkyl$^1$ et alkyl$^2$ are independently selected from (C$_1$-C$_6$)-alkyl groups, preferably from (C$_1$-C$_3$)-alkyl groups. Terminal alkyl (alkyl$^2$) is typically methyl, ethyl or propyl, preferably methyl. Examples of polyethers include polyethylene glycols as defined below.

"Polyethylene glycol" or "PEG" refers to a polyether group of formula —(CH$_2$CH$_2$O)$_x$alkyl$^2$, wherein x is an integer ranging from 2 to 20, preferably ranging from 2 to 10, more preferably ranging from 3 to 5; and wherein alkyl$^2$ is selected from (C$_1$-C$_6$)-alkyl groups, preferably from (C$_1$-C$_3$)-alkyl groups, preferably methyl.

"Polysaccharide" refers to a polymeric carbohydrate molecule composed of long chains of monosaccharide units bound together by glycosidic linkages; which may be linear or branched. Examples include starch, glycogen, cellulose and chitin.

"Protein" refers to a functional entity formed of one or more peptides.

"Siloxy" refers to the function —O—Si(R)$_3$ wherein R represents for example alkyl or aryl.

"Thioether" refers to a functional group with the connectivity C—S—C.

"Water-solubilizing group" refers to a group of atoms in a molecule which increase the hydrophilic character of the molecule, and especially which increases the solubility of the molecule in aqueous media. Examples of water-solubilizing groups are provided below.

DETAILED DESCRIPTION

The present invention relates to a ligand of Formula (I-0)

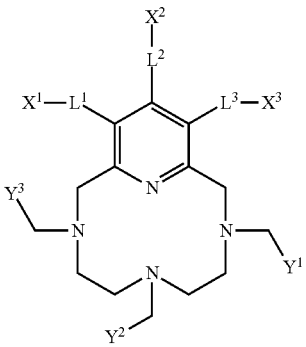

(I-0)

or a salt thereof;
wherein
$Y^1$, $Y^2$ and $Y^3$ each independently represents —COOH, —PO(OH)$R^0$ or an antenna of Formula (i-0):

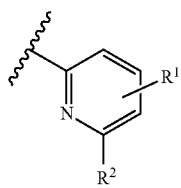

(i-0)

wherein $R^1$ represents a chromophore group and each $R^2$ represent independently represents —COOH or —PO(OH)$R^0$;
wherein each $R^0$ represent independently represents a hydrogen, aryl or alkyl;
provided that at least one among $Y^1$, $Y^2$ and $Y^3$ represents an antenna of Formula (i-0);
$L^1$, $L^2$ and $L^3$ each independently represents:
a single bond; or
a linker; said linker optionally additionally comprising a coupling product through which $X^1$, $X^2$ and $X^3$ are bounded to $L^1$, $L^2$ and $L^3$ respectively;
$X^1$, $X^2$ and $X^3$ each independently represents:
a hydrogen atom;
a coupling function; or
a bio-vectorizing group.

According to one embodiment, all $R^1$ in the ligand represent the same group. According to one embodiment, all $R^2$ in the ligand represent the same group. According to one embodiment, each $R^0$ represent independently represents a hydrogen, phenyl, benzyl, methyl, ethyl, propyl or butyl (e.g., n-butyl, sec-butyl, isobutyl, tert-butyl). In one embodiment, all $R^0$ in the ligand represent the same group.

According to one embodiment, $Y^1$, $Y^2$ and $Y^3$ each independently represents —COOH or an antenna of Formula (i-O), provided that at least one among $Y^1$, $Y^2$ and $Y^3$ represents an antenna of Formula (i-0).

According to one embodiment, each $R^2$ represents —COOH so that $Y^1$, $Y^2$ and $Y^3$ each independently represents —COOH, —PO(OH)$R^0$ or a picolinate of Formula (i):

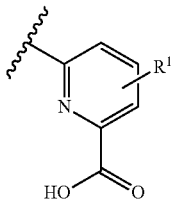

(i)

wherein $R^1$ represents a chromophore group;
provided that at least one among $Y^1$, $Y^2$ and $Y^3$ represents a picolinate of Formula (i).

According to one embodiment, $Y^1$, $Y^2$ and $Y^3$ each independently represents —COOH or a picolinate of Formula (i), provided that at least one among $Y^1$, $Y^2$ and $Y^3$ represents a picolinate of Formula (i).

According to one embodiment, at least two among $Y^1$, $Y^2$ and $Y^3$ represents a picolinate of Formula (i). In one embodiment, exactly two among $Y^1$, $Y^2$ and $Y^3$ represents a picolinate of Formula (i), i.e., one among $Y^1$, $Y^2$ and $Y^3$ represents —COOH and two among $Y^1$, $Y^2$ and $Y^3$ represent a picolinate of Formula (i). In another embodiment, $Y^1$, $Y^2$ and $Y^3$ each represents a picolinate of Formula (i).

According to one embodiment, $L^1$ and $L^3$ each represents a single bond; and $X^1$ and $X^3$ each represents a hydrogen atom; so that the ligand is of Formula (II-0):

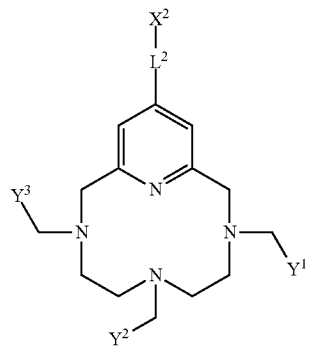

(II-0)

wherein $L^2$, $X^2$, $Y^1$, $Y^2$ and $Y^3$ are as defined hereabove.

According to one embodiment, $L^1$, $L^2$ and $L^3$ each represents a single bond; and $X^1$, $X^2$ and $X^3$ each represents a hydrogen atom; so that the ligand is of Formula (III-0):

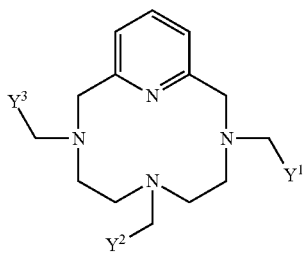

(III-0)

wherein $Y^1$, $Y^2$ and $Y^3$ are as defined hereabove.

According to one embodiment, $R^1$ is in para position relatively to nitrogen atom in Formula (i-0) or in Formula (i).

According to one embodiment, the ligand is of Formula (I-1) or of Formula (I-2):

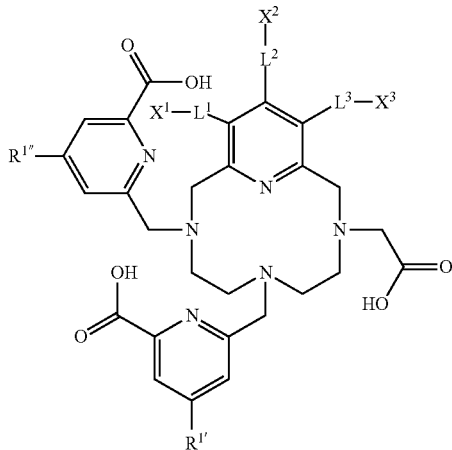
(I-1)

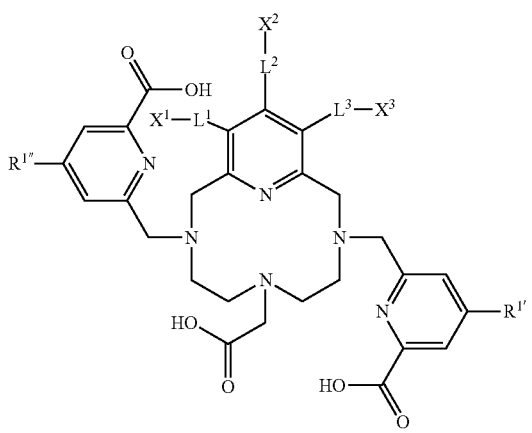
(I-2)

wherein $L^1$, $L^2$, $L^3$, $X^1$, $X^2$ and $X^3$ are as defined hereabove; and $R^{1'}$ and $R^{1'''}$ each represents independently a $R^1$ group as defined above.

According to one embodiment, the ligand is of Formula (II-1) or of Formula (II-2):

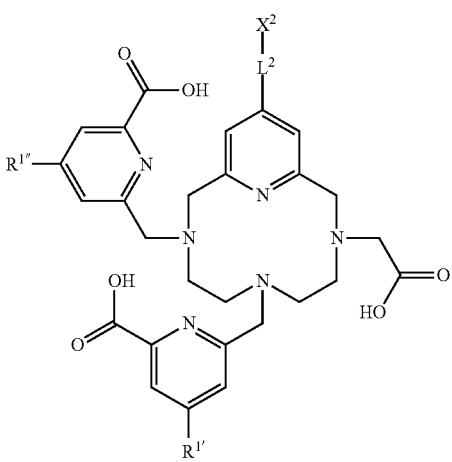
(II-1)

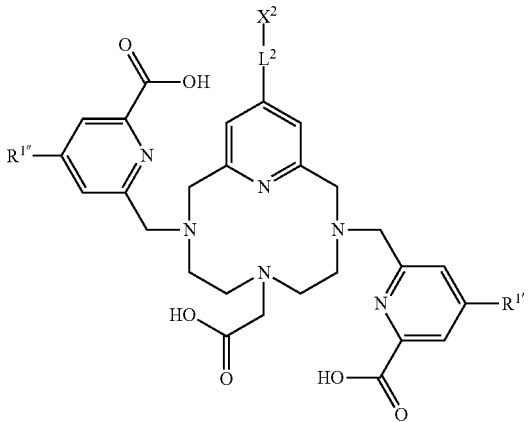
(II-2)

wherein $L^2$ and $X^2$ are as defined hereabove; and $R^{1'}$ and $R^{1'''}$ each represents independently a $R^1$ group as defined above.

According to one embodiment, the ligand is of Formula (III-1) or of Formula (III-2):

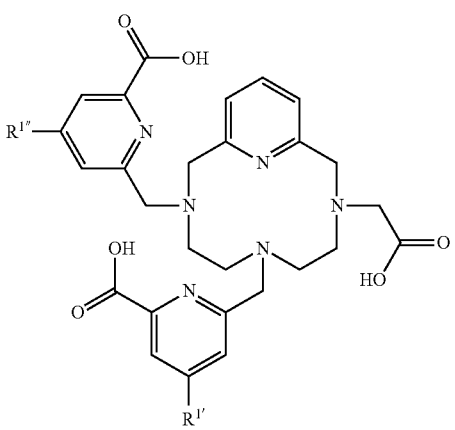
(III-1)

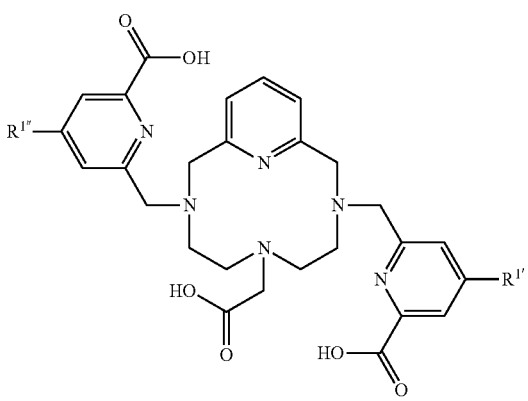
(III-2)

wherein $R^{1'}$ and $R^{1'''}$ each represents independently a $R^1$ group as defined above. According to a first embodiment, the chromophore group $R^1$ is of Formula (ii-0):

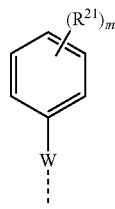

(ii-0)

wherein W is selected from double bond, triple bound, aryl or heteroaryl; m is an integer ranging from 1 to 5; and wherein each $R^{21}$ independently represents alkyl, alkoxy, —S-alkyl, —NH—(CO)-alkyl, —NH—(CS)-alkyl, —NH—(CO)—N($R^{N1}$)($R^{N2}$) wherein $R^{N1}$ and $R^{N2}$ represents independently alkyl, —NH—(CS)—N($R^{N1}$)($R^{N2}$) wherein $R^{N1}$ and $R^{N2}$ represents independently alkyl, or a water-solubilizing group; wherein each $R^{21}$ group is optionally substituted by at least one -$L^{41}$-$Z^{41}$ group;

wherein each $L^{41}$ independently represents a single bond or a linker; said linker optionally additionally comprising a coupling product through which $R^{21}$ is bounded to $L^{41}$; and wherein each $Z^{41}$ independently represents a water-solubilizing group.

In this first embodiment, the chromophore group $R^1$ is preferably of Formula (ii):

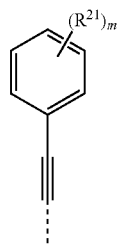

(ii)

wherein m is an integer ranging from 1 to 5; and wherein each $R^{21}$ independently represents alkyl, alkoxy, —S-alkyl, —NH—(CO)-alkyl, —NH—(CS)-alkyl, —NH—(CO)—N($R^{N1}$)($R^{N2}$) wherein $R^{N1}$ and $R^{N2}$ represents independently alkyl, —NH—(CS)—N($R^{N1}$)($R^{N2}$) wherein $R^{N1}$ and $R^{N2}$ represents independently alkyl, or a water-solubilizing group; wherein each $R^{21}$ group is optionally substituted by at least one -$L^{41}$-$Z^{41}$ group as defined hereinabove.

In one embodiment, m is an integer ranging from 1 to 3. In one specific embodiment, m is 1. In one embodiment, each $R^{21}$ group is substituted by exactly one -$L^{41}$-$Z^{41}$ group as defined hereinabove.

In one embodiment, each $R^{21}$ independently represents alkyl, alkoxy, —O-polyether, —S-alkyl, —S-polyether, or —NRR' wherein R represents hydrogen, alkyl, or polyether, and R' represents independently polyether.

In one embodiment, at least one $R^{21}$ represents —O-polyether or —NRR' wherein R represents hydrogen, alkyl, or polyether, and R' represents independently polyether. In one specific embodiment, the polyether is a polyethylene glycol (PEG).

According to one embodiment, $R^{21}$ is in para position relatively to the W group or to the alkyne function.

According to a second embodiment, the chromophore group $R^1$ is of Formula (iii):

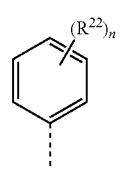

(iii)

wherein n is an integer ranging from 1 to 5; and wherein each $R^{22}$ independently represents alkyl, alkoxy, —S-alkyl, —NH—(CO)-alkyl, —NH—(CS)-alkyl, —NH—(CO)—N($R^{N1}$)($R^{N2}$) wherein $R^{N1}$ and $R^{N2}$ represents independently alkyl, —NH—(CS)—N($R^{N1}$)($R^{N2}$) wherein $R^{N1}$ and $R^{N2}$ represents independently alkyl, or a water-solubilizing group (such as for example —O-polyether or —S-polyether); wherein each $R^{22}$ group is optionally substituted by at least one -$L^{42}$-$Z^{42}$ group;

wherein each $L^{42}$ independently represents a single bond or a linker; said linker optionally additionally comprising a coupling product through which $R^{22}$ is bounded to $L^{42}$; and wherein each $Z^{42}$ independently represents a water-solubilizing group;

provided that at least one $R^{22}$ represents an electron-donor group selected from alkoxy, —O-polyether, —S-alkyl, —S-polyether, —NH—(CO)-alkyl, —NH—(CS)-alkyl, —NH—(CO)—N($R^{N1}$)($R^{N2}$) wherein $R^{N1}$ and $R^{N2}$ represents independently alkyl, and —NH—(CS)—N($R^{N1}$)($R^{N2}$) wherein $R^{N1}$ and $R^{N2}$ represents independently alkyl.

In one embodiment, n is an integer ranging from 1 to 3. In one specific embodiment, n is 1. In one specific embodiment, n is 2. In one specific embodiment, n is 3. In one embodiment, each $R^{22}$ group is substituted by exactly one -$L^{42}$-$Z^{42}$ group as defined hereinabove.

In this second embodiment, the chromophore group $R^1$ is preferably of Formula (iii'):

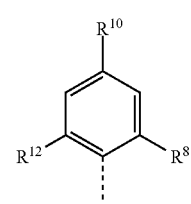

(iii')

wherein R' represents alkyl or alkoxy, preferably alkyl such as for example methyl, $R^{12}$ represents hydrogen, alkyl or alkoxy, preferably hydrogen, and wherein $R^{10}$ represents an electron-donor group selected from alkoxy, —O-polyether, —S-alkyl, —S-polyether, —NH—(CO)-alkyl, —NH—(CS)-alkyl, —NH—(CO)—N($R^{N1}$)($R^{N2}$) wherein $R^{N1}$ and $R^{N2}$ represents independently alkyl, and —NH—(CS)—N($R^{N1}$)($R^{N2}$) wherein $R^{N1}$ and $R^{N2}$ represents independently alkyl; wherein each of $R^8$, $R^{10}$ and $R^{12}$ group is optionally substituted by at least one -$L^{42}$-$Z^{42}$ group as defined hereinabove.

In one embodiment, at least one $R^{22}$ group in ortho-position ($R^8$ or $R^{12}$) represents alkyl, preferably methyl. In one specific embodiment, exactly one $R^{22}$ group in ortho-position ($R^8$ or $R^{12}$) represents alkyl, preferably methyl.

In one embodiment, each $R^{22}$ independently represents alkyl, alkoxy, —O-polyether, —S-alkyl, —S-polyether, or —NRR' wherein R represents hydrogen, alkyl, or polyether, and R' represents independently polyether; provided that at least one $R^{22}$ represents alkoxy, —O-polyether, —S-alkyl or —S-polyether. In one specific embodiment, at least one $R^{22}$ represents —O-polyether.

In one specific embodiment, the polyether is a polyethylene glycol (PEG). In one specific embodiment, the alkoxy is methoxy, ethoxy or propoxy.

According to one embodiment, $R^{22}$ is in para position relatively to picolinate group (i) (dotted line in Formula (ii) or (iii)).

The chromophore group $R^1$ may be substituted by at least one water-solubilizing group in order to improve its solubility in aqueous media. Improving hydrophily of the compound according to the invention may be relevant in order to include said compound in compositions for use in imaging or treatment and/or to solubilize said compound in biological fluids such as blood, human serum and the like.

According to one embodiment, the water-solubilizing group is a polyether or a polyether derivative such as for example polyether, —O-polyether, —S-polyether, or —NRR' wherein R represents hydrogen, alkyl, or polyether, and R' represents independently polyether. In one embodiment, the water-solubilizing group is —O-polyether or —NRR' wherein R and R' represents independently polyether. In one embodiment, the polyether is a polyethylene glycol (PEG). According to one embodiment, the water-solubilizing group is alkoxy or —S-alkyl.

According to one embodiment, the water-solubilizing group is a betaine. In one embodiment, the betaine is selected from compounds of formulae:

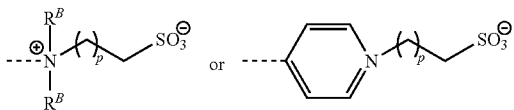

wherein $R^B$ represents a ($C_1$-$C_6$)-alkyl, preferably methyl or ethyl, propyl or butyl, more preferably methyl, and p is an integer ranging from 2 to 7, preferably 2 or 3. In one specific embodiment, the betaine is —$N^+(CH_3)_2$—$(CH_2)_3$—$SO_3^-$. In another specific embodiment, the betaine is —$N^+(C_2H_5)_2$—$(CH_2)_3$—$SO_3^-$. In another specific embodiment, the betaine is —$N^+(C_3H_7)_2$—$(CH_2)_3$—$SO_3^-$. Betaines are advantageous so as to avoid non-specific interaction of the ligand or chelate with biomolecules.

According to one embodiment, the water-solubilizing group is a carboxylate (—COO$^-$) or a sulfonate (—SO$_3^-$) group.

According to one embodiment, the water-solubilizing group is a group of formula -$L^{41}$-$Z^{41}$ or -$L^{42}$-$Z^{42}$ as described hereinabove.

The chromophore group $R^1$ may also be substituted by at least one oil-solubilizing group in order to improve its solubility in oily media.

According to one embodiment, the ligand is of Formula (IV-1-ii) or of Formula (IV-2-ii):

(IV-1-ii)

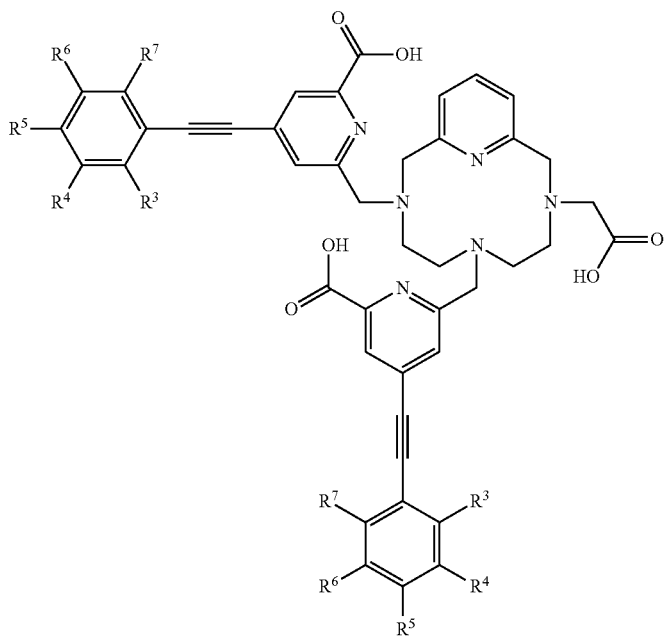

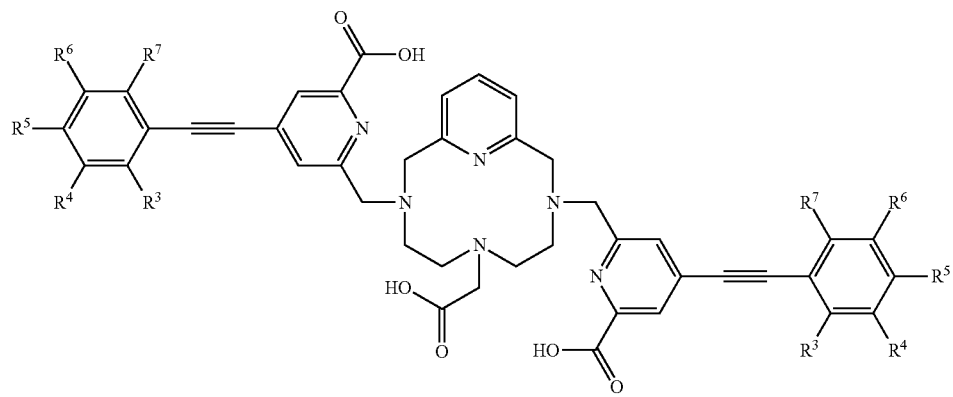

(IV-2-ii)

wherein $R^3$, $R^4$, $R^5$, $R^6$ and $R^7$ independently represent hydrogen, alkyl, alkoxy, —S-alkyl or a water-solubilizing group; preferably hydrogen, alkyl, alkoxy, —O-polyether, or —NRR' wherein R and R' represents independently polyether; provided that at least one among $R^3$, $R^4$, $R^5$, $R^6$ and $R^7$ represents a water-solubilizing group; preferably —O-polyether or —NRR'.

In one embodiment, exactly one among $R^3$, $R^4$, $R^5$, $R^6$ and $R^7$ represents —O-polyether or —NRR' wherein R and R' represent independently polyether. In one embodiment, $R^5$ represents —O-polyether. In one embodiment, $R^5$ represents —NRR' wherein R and R' represent independently polyether.

According to one embodiment, the ligand is of Formula (IV-1-iii) or of Formula (IV-2-iii):

(IV-1-iii)

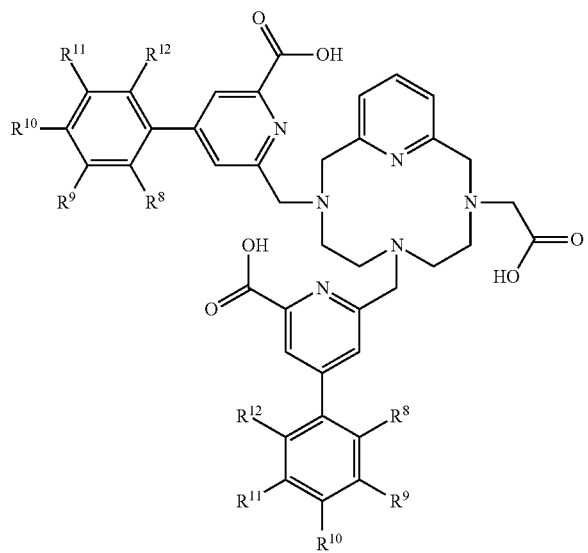

(IV-2-iii)

wherein $R^8$, $R^9$, $R^{10}$, $R^{11}$ and $R^{12}$ independently represent hydrogen, alkyl, alkoxy, —S-alkyl or a water-solubilizing group; preferably hydrogen, alkyl, alkoxy, or —O-polyether; provided that at least one among $R^8$, $R^9$, $R^{10}$, $R^{11}$ and $R^{12}$ represents —O-polyether or —S-polyether; preferably —O-polyether.

In one embodiment, exactly one among $R^8$, $R^9$, $R^{10}$, $R^{11}$ and $R^{12}$ represents —O-polyether. In one embodiment, $R^{10}$ represents —O-polyether.

According to one embodiment, $L^1$, $L^2$ and $L^3$ each independently represents a single bond or a linker selected from alkyl, aryl, arylalkyl, alkylaryl, heteroalkyl, heteroaryl, heteroarylalkyl, alkylheteroaryl, alkenyl and alkynyl; said linker optionally additionally comprising a coupling product through which $X^1$, $X^2$ and $X^3$ are bounded to $L^1$, $L^2$ and $L^3$ respectively. In one embodiment, the linker is selected from alkyl, arylalkyl, heteroalkyl, heteroaryl, heteroarylalkyl, alkylheteroaryl, alkenyl and alkynyl. In one embodiment, the linker is not an aryl. In one embodiment, the linker is not an alkylaryl. In one embodiment, the linker is not an alkyl. In one embodiment, the linker is not an arylalkyl.

According to one embodiment, $X^1$, $X^2$ and $X^3$ each independently represents a hydrogen atom; a coupling function selected from amine; isothiocyanate; isocyanate; activated ester such as for example N-hydroxysuccinimide ester, N-hydroxyglutarimide ester or maleimide ester; carboxylic acid; activated carboxylic acid such as for example acid anhydride or acid halide; alcohol; alkene; alkyne; halide; azide; siloxy; phosphonic acid; thiol; tetrazine; norbornen;

oxoamine; aminooxy; thioether; haloacetamide such as for example chloroacetamide, bromoacetamide or iodoacetamide; glutamate; glutaric anhydride, succinic anhydride, maleic anhydride; aldehyde; ketone; hydrazide; chloroformate; and maleimide; or a bio-vectorizing group.

In one embodiment, the coupling function is selected from following formulae (a), (b), (c), (d), (e), (f) and (g):

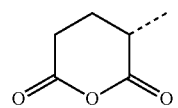
(a)

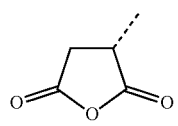
(b)

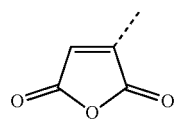
(c)

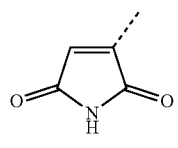
(d)

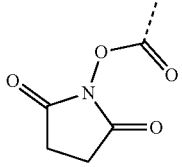
(e)

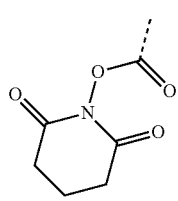
(f)

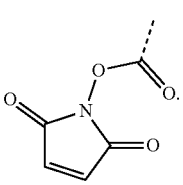
(g)

According to one embodiment, $X^1$, $X^2$ and $X^3$ each independently represents a hydrogen atom; a coupling function; or a bio-vectorizing group selected from antibody such as polyclonal or monoclonal antibody, hybrid or chimeric antibody, single-domain antibody, dimeric or trimeric antibody fragment construct or minibody; hapten; peptide; protein; polysaccharide; fatty acid; liposome; lipid; polyamine such as spermine; nanoparticle; polymeric microparticle; macrocyclic chelate; cationic group suitable for cellular internalization such as for example phosphonium moieties, which are known to target mitochondria (Kalyanaraman, B. et al., *Chemical Reviews*, 2017, Vol. 117, No. 15, pp. 10043-10120); and combinations thereof. Detailed information about suitable bio-vectorizing groups is provided hereabove ("Definitions" section).

According to one embodiment, $L^{41}$ and $L^{42}$ each independently represents a single bond or a linker selected from alkyl, aryl, arylalkyl, alkylaryl, heteroalkyl, heteroaryl, heteroarylalkyl, alkylheteroaryl, alkenyl and alkynyl; said linker optionally additionally comprising a coupling product through which $R^{21}$ and $R^{22}$ are bounded to $L^{41}$ and $L^{42}$ respectively. In one embodiment, $L^{41}$ and $L^{42}$ each independently represents an alkyl such as ethyl, propyl or butyl with optional coupling product. In one specific embodiment, $L^{41}$ and $L^{42}$ each independently represents propyl with optional coupling product.

In one specific embodiment, the coupling product is triazolyl.

According to one embodiment, $Z^{41}$ and $Z^{42}$ each independently represents a water-solubilizing group selected from polyethers and betaines. In one embodiment, $Z^{41}$ and $Z^{42}$ each independently represents a betaine.

The ligand according to the invention encompasses any enantiomers, solvates, polymorphs and multi-component complexes thereof. The ligand according to the invention also encompasses any salt thereof, preferably any pharmaceutically acceptable salt thereof.

Pharmaceutically acceptable salts include the acid addition and base salts thereof. Suitable acid addition salts are formed from acids, which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen, phosphate/dihydrogen, phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemi-salts of acids and bases may also be formed, e.g. hemi-sulphate and hemi-calcium salts. When the compound contains an acidic group as well as a basic group it may also form internal salts. When the compound contains a hydrogen-donating heteroatom (e.g. NH), a pharmaceutically acceptable salt thereof includes also salts and/or isomers formed by transfer of said hydrogen atom to a basic group or atom within the molecule.

These salts may be prepared by standard procedures, e.g., by reacting a free acid with a suitable organic or inorganic base.

Preferred salts are carboxylate salts, preferably triple carboxylate salts. According to an embodiment, the carboxylate salt is a potassium salt, preferably a triple potassium salt.

In one embodiment, the ligand according to the invention is selected from the compounds of Table 1 below, and carboxylate salts thereof:

TABLE 1

| # | Formula | Name |
|---|---|---|
| A1 | | 6,6'-((9-(carboxymethyl)-3,6,9-triaza-1(2,6)-pyridinacyclodecaphane-3,6-diyl)bis(methylene))bis(4-((4-(2-(2-(2-methoxyethoxy)ethoxy)ethoxy)phenyl)ethynyl)picolinic acid) |
| A2 | | 6,6'-((9-(carboxymethyl)-3,6,9-triaza-1(2,6)-pyridinacyclodecaphane-3,6-diyl)bis(methylene))bis(4-((4-(bis(2-(2-(2-methoxyethoxy)ethoxy)ethyl)amino)phenyl)ethynyl)picolinic acid) |

TABLE 1-continued

| # | Formula | Name |
|---|---|---|
| A3 | | 6,6'-((9-(carboxymethyl)-3,6,9-triaza-1(2,6)-pyridinacyclodecaphane-3,6-diyl)bis(methylene))bis(4-(4-(2-(2-(2-methoxyethoxy)ethoxy)ethoxy)-2-methylphenyl)picolinic acid) |
| A4 | | 6,6'-((6-(carboxymethyl)-3,6,9-triaza-1(2,6)-pyridinacyclodecaphane-3,9-diyl)bis(methylene))bis(4-((4-(2-(2-(2-methoxyethoxy)ethoxy)ethoxy)phenyl)ethynyl)picolinic acid) |

TABLE 1-continued

| # | Formula | Name |
|---|---------|------|
| A5 | | 3,3'-(((((((((9-(carboxymethyl)-3,6,9-triaza-1(2,6)-pyridinacyclodecaphane-3,6-diyl)bis(methylene))bis(6-carboxypyridine-2,4-diyl))bis(ethyne-2,1-diyl))bis(4,1-phenylene))bis(oxy))bis(ethane-2,1-diyl))bis(1H-1,2,3-triazole-4,1-diyl))bis(propane-3,1-diyl))bis(dimethyl-ammoniumdiyl))bis(propane-1-sulfonate) |
| A6 | | 6,6'-((1⁴-bromo-9-(carboxymethyl)-3,6,9-triaza-1(2,6)-pyridinacyclodecaphane-3,6-diyl)bis(methylene))bis(4-(4-methoxy-2-methylphenyl)picolinic acid) |

The compounds of Table 1 were named using ChemDraw® Professional 15.0 (PerkinElmer).

In one embodiment, the ligand according to the invention is selected from the triple potassium carboxylate salts of Table 2 below:

TABLE 2

| # | Formula | Name |
|---|---------|------|
| S1 | | potassium 6,6'-((9-(carboxylatomethyl)-3,6,9-triaza-1(2,6)-pyridinacyclodecaphane-3,6-diyl)bis(methylene))bis(4-((4-(2-(2-(2-methoxyethoxy)ethoxy)ethoxy)phenyl)ethynyl)picolinate) |
| S2 | | potassium 6,6'-((9-(carboxylatomethyl)-3,6,9-triaza-1(2,6)-pyridinacyclodecaphane-3,6-diyl)bis(methylene))bis(4-((4-(bis(2-(2-(2-methoxyethoxy)ethoxy)ethyl)amino)phenyl)ethynyl)picolinate) |

TABLE 2-continued

| # | Formula | Name |
|---|---------|------|
| S3 | | potassium 6,6'-((9-(carboxylatomethyl)-3,6,9-triaza-1(2,6)-pyridinacyclodecaphane-3,6-diyl)bis(methylene))bis(4-(4-(2-(2-(2-methoxyethoxy)ethoxy)ethoxy)-2-methylphenyl)picolinate) |
| S4 | | potassium 6,6'-((6-(carboxylatomethyl)-3,6,9-triaza-1(2,6)-pyridinacyclodecaphane-3,9-diyl)bis(methylene))bis(4-((4-(2-(2-(2-methoxyethoxy)ethoxy)ethoxy)phenyl)ethynyl)picolinate) |

TABLE 2-continued

| # | Formula | Name |
|---|---------|------|
| S5 | | potassium 6,6'-((9-(carboxylatomethyl)-3,6,9-triaza-1(2,6)-pyridinacyclodecaphane-3,6-diyl)bis(methylene))bis(4-((4-(2-(1-(3-(dimethyl(3-sulfonatopropyl)ammonio)propyl)-1H-1,2,3-triazol-4-yl)ethoxy)phenyl)ethynyl)picolinate) |
| S6 | | potassium 6,6'-((14-bromo-9-(carboxylatomethyl)-3,6,9-triaza-1(2,6)-pyridinacyclodecaphane-3,6-diyl)bis(methylene))bis(4-(4-methoxy-2-methylphenyl)picolinate) |

The compounds of Table 2 were named using ChemDraw© Professional 15.0 (PerkinElmer).

In another embodiment, the ligand according to the invention is selected from the triple sodium (Na) carboxylate salts of the compounds presented in Table 2 above, i.e., the compounds wherein potassium (K) ion is replaced by sodium (Na) ion. Sodium carboxylate salts are named S1', S2', etc., analogously with the names of the compounds of Table 2 above.

The present invention further relates to a process for manufacturing a ligand according to the invention.

According to one embodiment, the ligand is manufactured by any suitable synthetic method known from a skilled artisan.

According to one embodiment, the ligand according to the invention is obtained starting from a compound of formula (I-$R^P$)

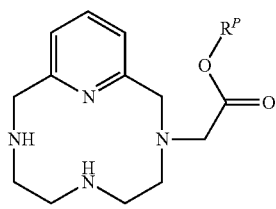
(I-R$^P$)

wherein R$^P$ represents an alkyl group; such as for example:
methyl 3,6,9,15-tetraazabicyclo[9.3.1]pentadecane-1(15),11,13-triene-3-acetate (I4):

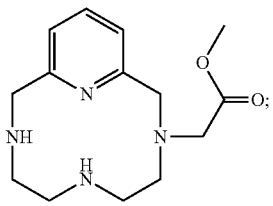
(I4)

or
tert-butyl 2-(3,6,9-triaza-1(2,6)-pyridinacyclodecaphane-6-yl)acetate (I8):

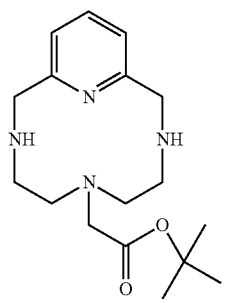
(I8)

According to one embodiment, the process for manufacturing a ligand according to the invention comprises:
(1) reacting I4 or I8 with at least two equivalents of a compound of Formula (i-E):

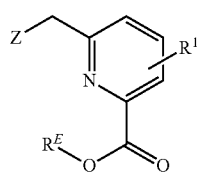
(i-E)

wherein R$^E$ represents a suitable protecting group being an alkyl such as for example methyl, ethyl, isopropyl or tert-butyl; R$^1$ is as described hereabove; and Z represents a suitable leaving group or a halide;
so as to obtain a carboxylate tri-ester of the ligand of formula (III-E):

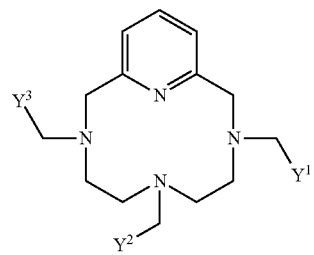
(III-E)

wherein Y$^1$, Y$^2$ and Y$^3$ each independently represents —COOR$^E$ or a picolinate ester of Formula (i-E):

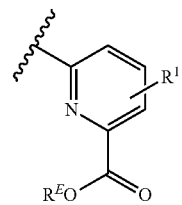

wherein R$^E$ and R$^1$ are as described hereabove;
provided that at least two among Y$^1$, Y$^2$ and Y$^3$ represents a picolinate ester of Formula (i-E); and
(2) deprotecting carboxylate tri-ester (III-E) so as to obtain the ligand.

For example, Z may be mesylate (Ms) and reaction step (1) may be carried out in presence of a base (e.g. potassium carbonate) in a solvent (e.g. acetonitrile).

In a first embodiment, deprotection step (2) is followed by a deprotonation step (3) of the ligand so as to obtain a carboxylate salt. In a second embodiment, a single deprotection-deprotonation step (2-3) is carried out by means of a base, so as to obtain a carboxylate salt directly from carboxylate tri-ester E. For example, deprotection step (2) may be carried out by means of potassium hydroxide (KOH) in a solvent (e.g. EtOH or a mixture of THF and MeOH or THF and EtOH) at 65° C. or at reflux; or by means of diluted hydrochloric acid (3M) at room temperature.

According to one embodiment, the pyridine moiety is functionalized by introduction of a coupling function before carrying out step (1) above. According to another embodiment, the pyridine moiety of the pyclen is functionalized after carrying out step (1) above and before carrying out step (2) above. According to another embodiment, the pyridine moiety is functionalized after carrying out step (2) above.

The present invention further relates to a carboxylate ester of a compound as described hereabove.

According to one embodiment, the carboxylate ester is a compound as described hereabove wherein Y$^1$, Y$^2$ and Y$^3$ each independently represents —COOR$^E$ or a picolinate ester of Formula (i-E):

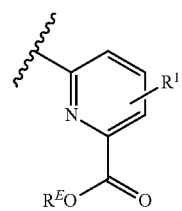

wherein each $R^E$ independently represents alkyl and $R^1$ is a described hereabove. Carboxylate esters according to the invention are useful as synthetic intermediates for manufacturing a ligand according to the invention, because the ester moiety acts as a protective group of the carboxylic acid group during synthesis, which can be removed in presence of a strong basis to yield the corresponding carboxylate salt, as shown hereabove. In one embodiment, $R^E$ represents methyl or tert-butyl.

In one embodiment, the carboxylate ester according to the invention is selected from the carboxylates tri-esters of Table 3 below:

TABLE 3

| # | Formula | Name |
|---|---------|------|
| E1 | 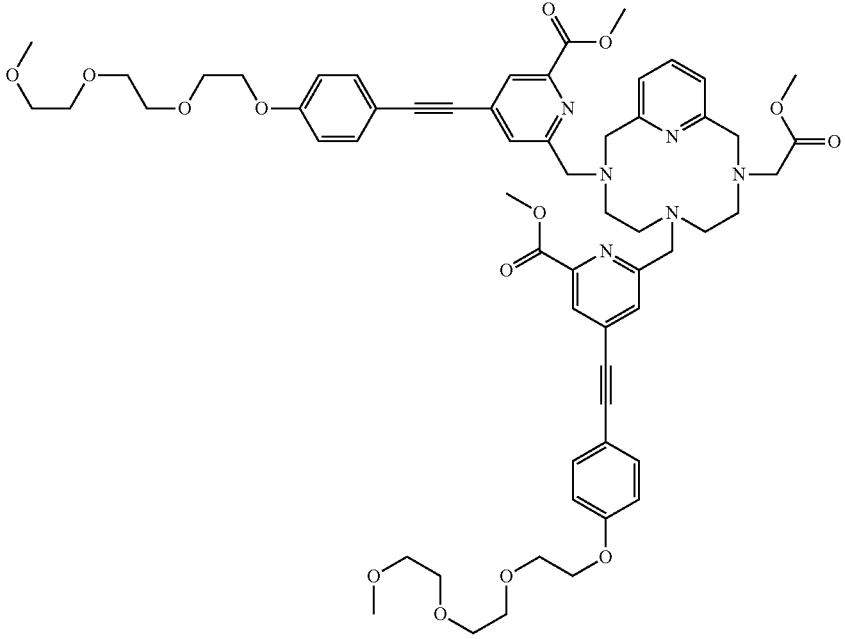 [SMILES: COCCOCCOCCOc1ccc(C#Cc2cc(CN3CCN(CC(=O)OC)Cc4cccc(n4)CN(Cc4cc(C#Cc5ccc(OCCOCCOCCOC)cc5)cc(C(=O)OC)n4)CC3)nc(C(=O)OC)c2)cc1] | dimethyl 6,6'-((9-(2-methoxy-2-oxoethyl)-3,6,9-triaza-1(2,6)-pyridinacyclodecaphane-3,6-diyl)bis(methylene))bis(4-((4-(2-(2-(2-methoxyethoxy)ethoxy)ethoxy)phenyl)ethynyl)picolinate) |
| E2 | 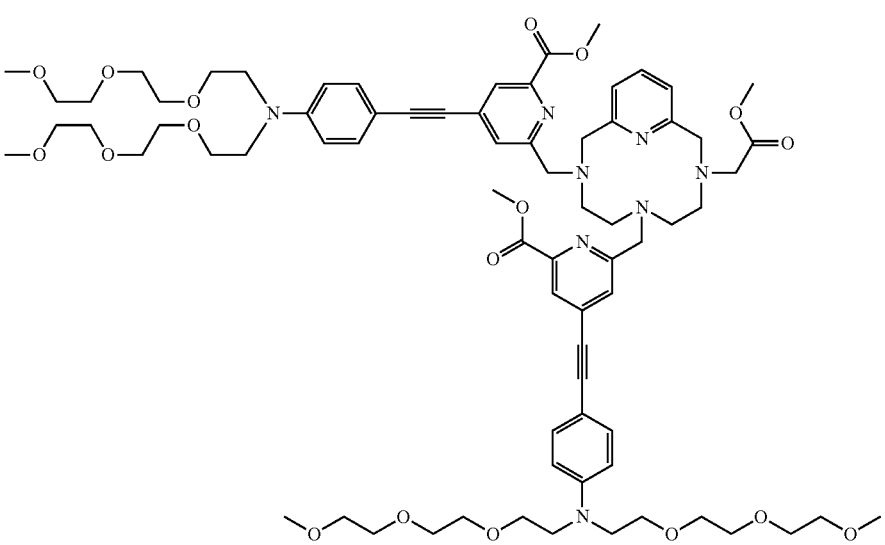 | dimethyl 6,6'-((9-(2-methoxy-2-oxoethyl)-3,6,9-triaza-1(2,6)-pyridinacyclodecaphane-3,6-diyl)bis(methylene))bis(4-((4-(bis(2-(2-(2-methoxyethoxy)ethoxy)ethyl)amino)phenyl)ethynyl)picolinate) |

TABLE 3-continued

| # | Formula | Name |
| --- | --- | --- |
| E3 | | dimethyl 6,6'-((9-(2-methoxy-2-oxoethyl)-3,6,9-triaza-1(2,6)-pyridinacyclodecaphane-3,6-diyl)bis(methylene)) bis(4-(4-(2-(2-(2-methoxyethoxy)ethoxy)ethoxy)-2-methylphenyl)picolinate) |
| E4 | | dimethyl 6,6'-((6-(2-methoxy-2-oxoethyl)-3,6,9-triaza-1(2,6)-pyridinacyclodecaphane-3,9-diyl)bis(methylene)) bis(4-((4-(2-(2-(2-methoxyethoxy)ethoxy)ethoxy)phenyl)ethynyl) picolinate) |

TABLE 3-continued

| # | Formula | Name |
|---|---|---|
| E5 | | 3,3'-((((((((((9-(2-methoxy-2-oxoethyl)-3,6,9-triaza-1(2,6)-pyridinacyclodecaphane-3,6-diyl)bis(methylene))bis(6-(methoxycarbonyl)pyridine-2,4-diyl))bis(ethyne-2,1-diyl))bis(4,1-phenylene))bis(oxy))bis(ethane-2,1-diyl))bis(1H-1,2,3-triazole-4,1-diyl))bis(propane-3,1-diyl))bis(dimethyl-ammoniumdiyl))bis(propane-1-sulfonate) |
| E6 | | dimethyl 6,6'-((14-bromo-9-(2-methoxy-2-oxoethyl)-3,6,9-triaza-1(2,6)-pyridinacyclodecaphane-3,6-diyl)bis(methylene))bis(4-(4-methoxy-2-methylphenyl)picolinate) |

The compounds of Table 3 were named using ChemDraw® Professional 15.0 (PerkinElmer).

The present invention further relates to intermediate compounds useful in a synthesis of a ligand of the invention as described hereabove and/or in a synthesis of a chelate according to the invention as described below.

In one embodiment, the intermediate according to the invention is selected from the compounds of Table 4 below, and salts thereof:

TABLE 4

| # | Formula | Name |
|---|---------|------|
| 117 | | dimethyl 6,6'-((9-(2-methoxy-2-oxoethyl)-3,6,9-triaza-1(2,6)-pyridinacyclodecaphane-3,6-diyl)bis(methylene)) bis(4-((4-((4-(triisopropylsilyl)but-3-yn-1-yl)oxy)phenyl)ethynyl) picolinate) |
| 118 | | dimethyl 6,6'-((9-(2-methoxy-2-oxoethyl)-3,6,9-triaza-1(2,6)-pyridinacyclodecaphane-3,6-diyl)bis(methylene)) bis(4-((4-(but-3-yn-1-yloxy)phenyl)ethynyl) picolinate) |

The compounds of Table 4 were named using ChemDraw® Professional 15.0 (PerkinElmer).

In one specific embodiment, the intermediate is a carboxylic acid of a compound of Table 4 above, i.e., the compound wherein the methyl ester groups are replaced by carboxylic acid group (—COOH).

In one specific embodiment, the intermediate is a triple potassium carboxylate salt of a compound of Table 4 above. In another specific embodiment, the intermediate is a triple sodium carboxylate salt of a compound of Table 4 above.

The present invention further relates to a chelate resulting from the complexation of a ligand according to the invention with a metallic cation.

According to one embodiment, the metallic cation is a lanthanide cation. In one embodiment, the lanthanide cation is selected from cerium (III), praseodymium (III), neodymium (III), samarium (III), europium (III), gadolinium (III), terbium (III), dysprosium (III), holmium (III), erbium (III), thulium (III), ytterbium (III) and lutetium (III). In one specific embodiment, the lanthanide cation is selected from neodymium (III), samarium (III), europium (III), terbium (III), dysprosium (III), erbium (III), and ytterbium (III). In one more specific embodiment, the lanthanide cation is samarium (III). In one more specific embodiment, the lanthanide cation is europium (III). In one more specific embodiment, the lanthanide cation is terbium (III).

In one more specific embodiment, the lanthanide cation is dysprosium (III). In one more specific embodiment, the lanthanide cation is ytterbium (III).

The present invention further relates to a process for manufacturing a chelate comprising a step of contacting a ligand according to the invention with a metallic cation, especially with a lanthanide cation. The present invention further relates to the use of a ligand according to the invention in the manufacture of a chelate, especially a chelate with a lanthanide cation.

According to one embodiment, the process of manufacturing the chelate of the invention comprises reacting the ligand according to the invention with a metallic cation in an aqueous medium, preferably by adjusting the pH at a value ranging from 5 to 8, e.g., with a basis such as potassium carbonate (KOH). The chelation process is preferably conducted at a temperature ranging from room temperature to reflux, preferably at reflux.

In one embodiment, the chelation process is conducted at room temperature or at about 30° C. for a period ranging from 2 to 3 days. In one embodiment, the chelation process is conducted at reflux for a period ranging from 12 to 24 hours.

In an embodiment, the metallic cation used in the process of manufacturing the chelate of the invention is under the form of a metal salt, preferably perchlorate, chloride, bromide, nitrates, sulfates, acetate, triflate salts.

The present invention further relates to a composition comprising a ligand and/or a chelate according to the invention. According to one embodiment, the composition is a pharmaceutical composition comprising a ligand and/or a chelate according to the invention in association with at least one pharmaceutically acceptable excipient.

The present invention further relates to a medicament comprising the ligand and/or the chelate according to the invention. According to one embodiment, the medicament is a radiopharmaceutical comprising a chelate according to the invention.

The present invention further relates to a kit comprising a ligand and/or a chelate according to the invention.

According to one embodiment, the kit comprises a first container comprising the ligand and a second container comprising the metallic cation.

The present invention further relates to a use of a ligand and/or a chelate according to the invention in imaging.

According to one embodiment, the ligand and/or the chelate is used in biological imaging.

In one embodiment, the biological imaging is medical imaging. In one specific embodiment, the medical imaging is in vitro imaging such as cellular or tissue imaging.

In one specific embodiment, the medical imaging is luminescence imaging such as fluorescence or phosphorescence microscopy.

According to one embodiment, the imaging is luminescence imaging, preferably photoluminescence imaging. In one specific embodiment, the luminescence imaging is fluorescence microscopy or phosphorescence microscopy; under one-photon excitation (mono-photonic) or two photons excitation (bi-photonic). In one further specific embodiment, the luminescence imaging is Fluorescence Resonance Energy Transfer (FRET). In one further specific embodiment, the luminescence imaging is Homogeneous Time Resolved Fluorescence® (HTRF®) bioassay. In one further specific embodiment, the luminescence imaging is two-photon absorption (TPA).

According to one embodiment, the chelate is used as a tag in bioassays or as an optical probe.

According to one embodiment, a chelate of lanthanide, preferably europium (III), terbium (III), samarium (III) or ytterbium (III), is used in photoluminescence imaging.

The present invention further relates to a chelate according to the invention for use as a medicament. According to one embodiment, the chelate is for use as a radiopharmaceutical. For example, chelates of radioisotopes such as chelates of $^{153}$Sm, $^{177}$Lu, $^{149}$Tb, $^{166}$Ho or $^{169}$Er may be used in radioisotope therapy (RIT). Depending on a bio-vectorizing group present on the chelate, a broad variety of diseases may be targeted, e.g., hyperthyroidism, proliferative diseases or blood disorders.

The present invention thus provides methods of treatment and/or prevention of diseases, comprising the administration of a therapeutically effective amount of a ligand and/or a chelate, preferably a chelate of a radioisotope, to a patient in need thereof. The invention further provides the use of a ligand and/or a chelate, preferably a chelate of a radioisotope, for the manufacture of a medicament, preferably a radiopharmaceutical.

EXAMPLES

The present invention is further illustrated by the following examples.

Example 1: Synthesis of Ligands According to the Invention

General Methods

Analytic HPLC was performed on a Prominence Shimadzu HPLC/LCMS-2020 equipped with a UV SPD-20 A detector. The chromatographic system employs HPLC (Vision HT C18 HL 5μ 250×4.6 mm) with H$_2$O and MeCN as eluents [isocratic 100% H$_2$O (5 min), linear gradient from 0 to 90% MeCN (10 min), isocratic 90% MeCN (5 min)] at a flow rate of 1 mL/min and UV detection at 254 and 350 nm. NMR spectra were recorded at the "Services communs" of the University of Brest. $^1$H and $^{13}$C NMR spectra were recorded using Bruker Avance 500 (500 MHz), Bruker Avance 400 (400 MHz), or BrukerAMX-3 300 (300 MHz) spectrometers. HRMS analyses were realized on a HRMS Q-Tof MaXis, sources ESI, APCI, APPI, nano-ESI (at the Institute of Organic and Analytic Chemistry [ICOA] in Orléans).

General Materials

Reagents were purchased from ACROS Organics and from Aldrich Chemical Co and used without further purification, except pyclen (I1) purchased from Glixx Laboratories Inc. Dialysis membranes (cut-off 100-500 Da) were purchased from Spectrumlabs. All solvents were dried and distilled prior to use according to standard methods.

Methyl 3,6,9,15-tetraazabicyclo[9.3.1]pentadecane-1 (15),11,13-triene-3-acetate (I4) was synthesized as previously described from 3,6,9,15-tetraazabicyclo[9.3.1] pentadeca-1(15),11,13-triene (pyclen, I1) and di-protected derivatives I2 and I3 (Le Fur, M. et al., WO 2017/109217 A1) by means of process summarized below:

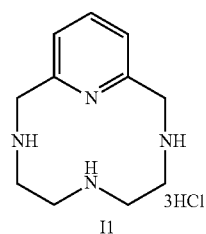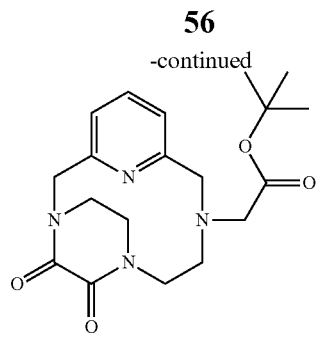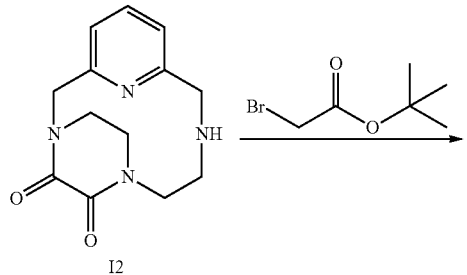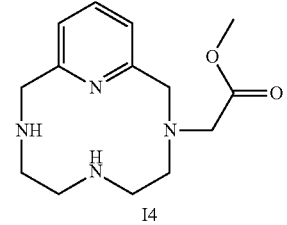
Example 1-1: Synthesis of Ligand S1
Scheme 1: Synthesis of the [Ln(S1)] complexes.
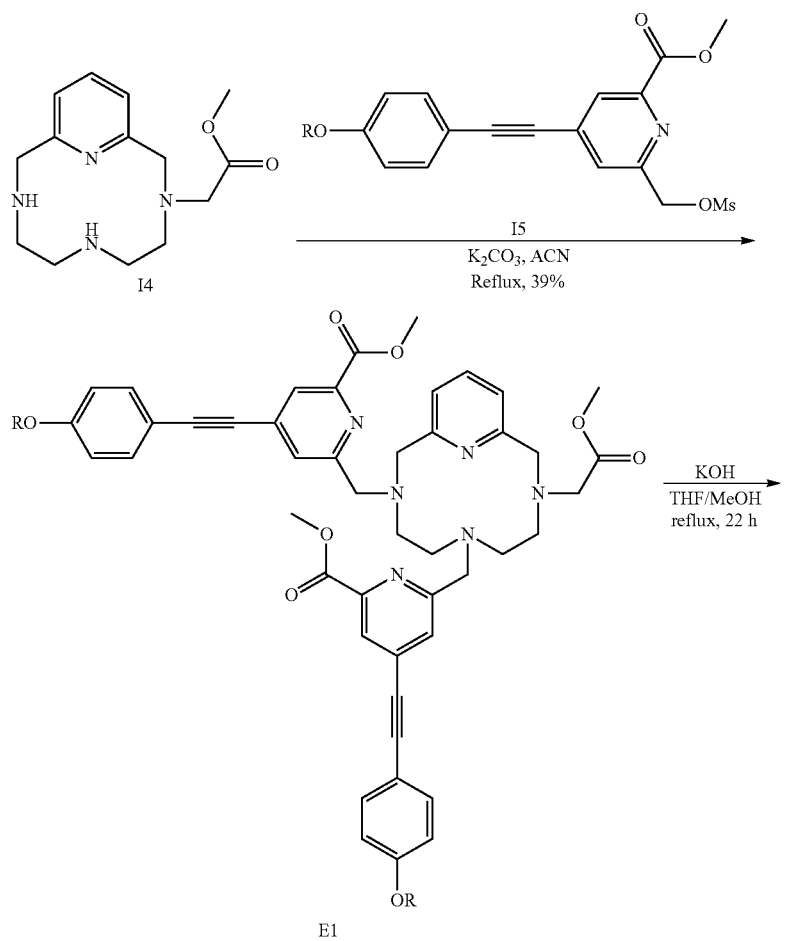

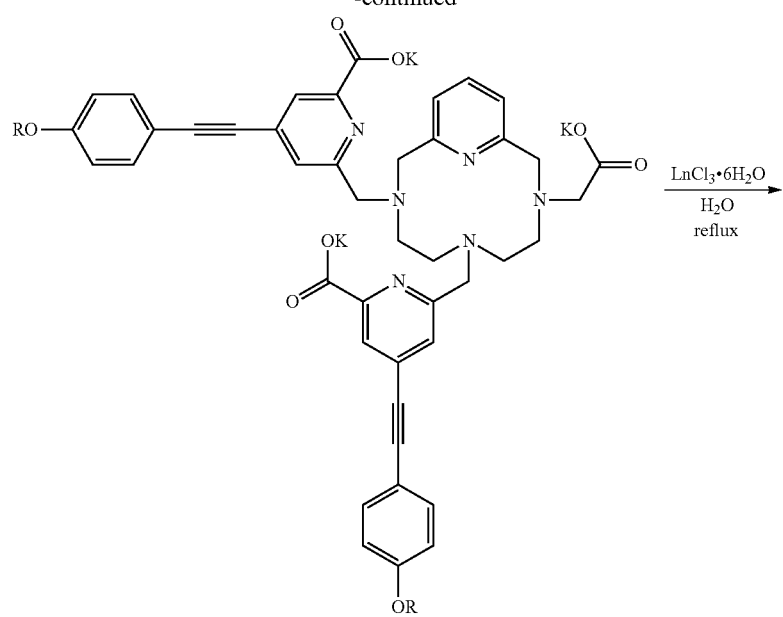
S1
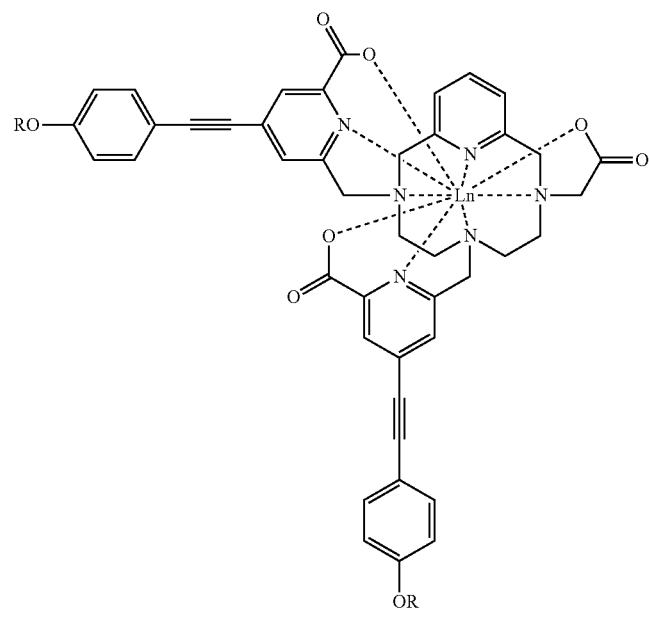
[Ln(S1)]
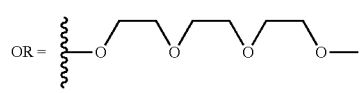

Methyl 4-((4-(2-(2-(2-methoxyethoxy)ethoxy)ethoxy)phenyl)ethynyl)-6-(((methylsulfonyl)oxy)methyl)picolinate (I5)

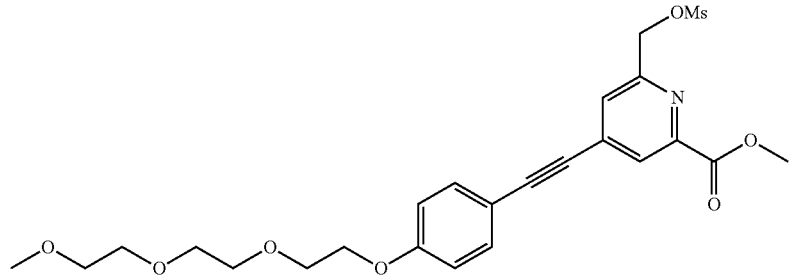

was synthesized as previously described (Walton, J. W., et al., *Chemical Communications*, 2013, Vol. 49, No. 16, pp. 1600-1602).

Synthesis of dimethyl 6,6'-((9-(2-methoxy-2-oxoethyl)-3,6,9-triaza-1(2,6)-pyridinacyclodecaphane-3,6-diyl)bis(methylene))bis(4-((4-(2-(2-(2-methoxyethoxy)ethoxy)ethoxy)phenyl)ethynyl)picolinate) (E1)

A solution of compound I4 (106 mg, 0.38 mmol) and $K_2CO_3$ (211 mg, 1.52 mmol, 4 eq) in $CH_3CN$ (9.5 mL) was stirred at room temperature for 30 min. To this solution was added dropwise a solution of mesylated antenna I5 (396 mg, 0.78 mmol, 2.05 eq) in $CH_3CN$ (14 mL). The reaction mixture was stirred at room temperature for 15 h and solvents were evaporated to dryness. The residue was taken up in $CH_2Cl_2$ and the residual salts were filtered on celite. Solvents were evaporated to dryness and the crude was purified by chromatography on neutral alumina (eluent: $CH_2Cl_2$/MeOH 100/0 to 100/1.5) to give compound E1 (166 mg, 0.15 mmol, 39%) as a brown oil. Rf ($CH_2Cl_2$/MeOH 100/3)=0.29. $^1H$ NMR spectrum could not be described because of its complexity. $^{13}C$ NMR (75 MHz, $CDCl_3$) δ 171.6, 165.2, 164.4, 160.1, 159.9, 159.8, 158.7, 158.4, 157.8, 147.4, 147.3, 137.9, 134.4, 134.3, 133.5, 133.4, 127.8, 127.6, 125.1, 124.9, 121.3, 120.7, 114.7, 114.6, 113.3, 113.2, 97.0, 96.6, 84.7, 84.6, 71.7, 70.6, 70.4, 70.3, 69.3, 67.4, 62.5, 61.9, 61.6, 61.3, 59.3, 58.8, 57.1, 55.6, 54.8, 52.9, 52.7, 51.5. ESI-HR-MS (positive, MeOH) m/z calcd. for $[C_{60}H_{73}N_6O_{14}]^+$: 1101.5179, found: 101.5183, $[M+H]^+$; calcd. for $[C_{60}H_{74}N_6O_{14}]^{2+}$: 551.2626, found: 551.2631, $[M+2H]^{2+}$; calcd. for $[C_{60}H_{72}N_6NaO_{14}]^+$: 1123.4999, found: 1123.500, $[M+Na]^+$.

Synthesis of potassium 6,6'-((9-(carboxylatomethyl)-3,6,9-triaza-1(2,6)-pyridinacyclodecaphane-3,6-diyl)bis(methylene))bis(4-((4-(2-(2-(2-methoxyethoxy)ethoxy)ethoxy)phenyl)ethynyl)picolinate) (S1)

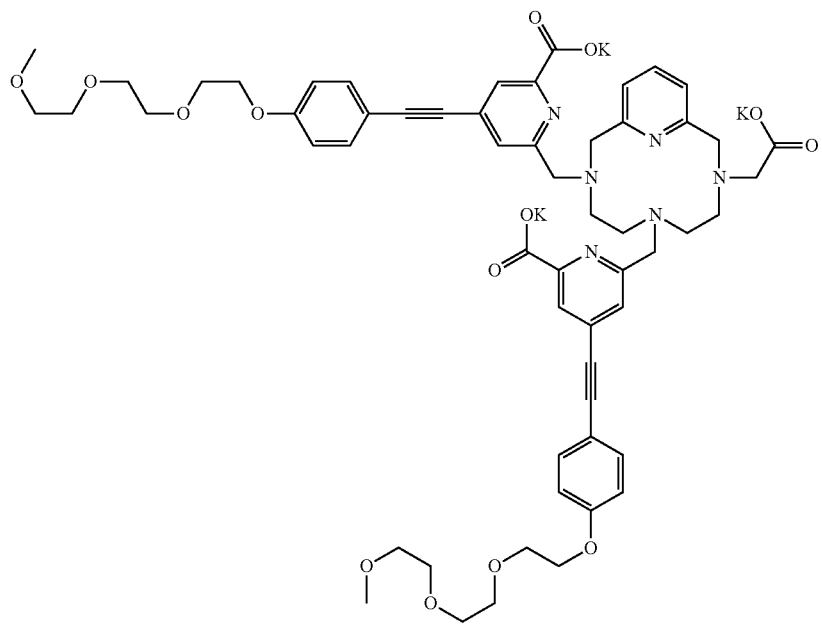

To a solution of compound E1 (130 mg, 0.12 mmol) in THF/MeOH (8/2 v/v, 7.9 mL) was added 1M KOH (1.57 mL). The reaction mixture was stirred at reflux for 22 h. Solvents were evaporated and the residue was submitted to a dialysis for 15 h (cut-off 100-500 Da) to give compound S1 as a brown oil. $^1$H NMR (500 MHz, D$_2$O) δ 7.74 (d, J=1.0 Hz, 1H), 7.61 (d, J=0.7 Hz, 1H), 7.47 (t, J=7.7 Hz, 1H), 7.18 (s, 1H), 7.13 (d, J=8.6 Hz, 2H), 7.08 (d, J=8.5 Hz, 2H), 6.93 (d, J=7.7 Hz, 1H), 6.87 (s, 1H), 6.76 (dd, J=8.8, 3.0 Hz, 4H), 6.73 (d, J=7.6 Hz, 1H), 4.08-3.51 (m, 36H), 3.31 (s, 3H), 3.31 (s, 3H). $^{13}$C NMR (126 MHz, D$_2$O) δ 181.2, 174.2, 174.0, 161.9, 161.8, 161.2, 160.2, 156.9, 156.4, 154.0, 140.9, 136.7, 136.4, 136.1, 135.7, 131.2, 129.7, 127.9, 126.7, 123.7, 123.3, 117.5, 116.6, 116.5, 98.8, 97.8, 88.7, 88.1, 73.8, 72.7, 72.4, 72.3, 71.7, 70.0, 69.9, 65.9, 61.1, 60.9, 60.0, 59.7, 59.2, 58.2, 57.3, 54.5, 50.5. ESI-HR-MS (positive, H$_2$O) m/z calcd. for [C$_{57}$H$_{64}$FeN$_6$O$_{14}$]$^+$: 1112.3824, found: 1112.3837, [M−2H+Fe]$^+$; calcd. for [C$_{57}$H$_{67}$N$_6$O$_{14}$]$^+$: 1059.4709, found: 1059.4720, [M+H]$^+$; calcd. for [C$_{57}$H$_{65}$FeN$_6$O$_{14}$]$^{2+}$: 556.6949, found: 556.6965, [M−H+Fe]$^{2+}$; calcd. for [C$_{57}$H$_{68}$N$_6$O$_{14}$]$^{2+}$: 530.2391, found: 530.2397, [M+2H]$^{2+}$.

Example 1-2: Synthesis of Ligand S2

Scheme 2: Synthesis of the [Ln(S2)] complexes

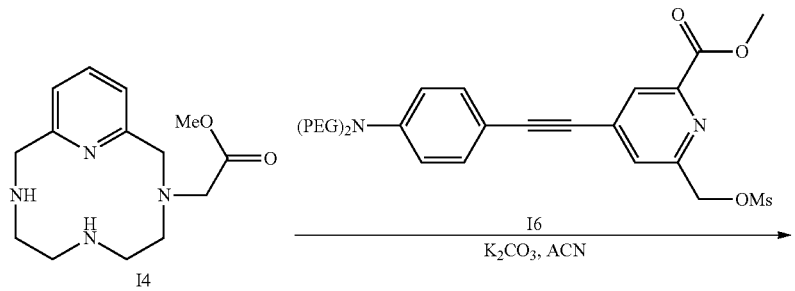

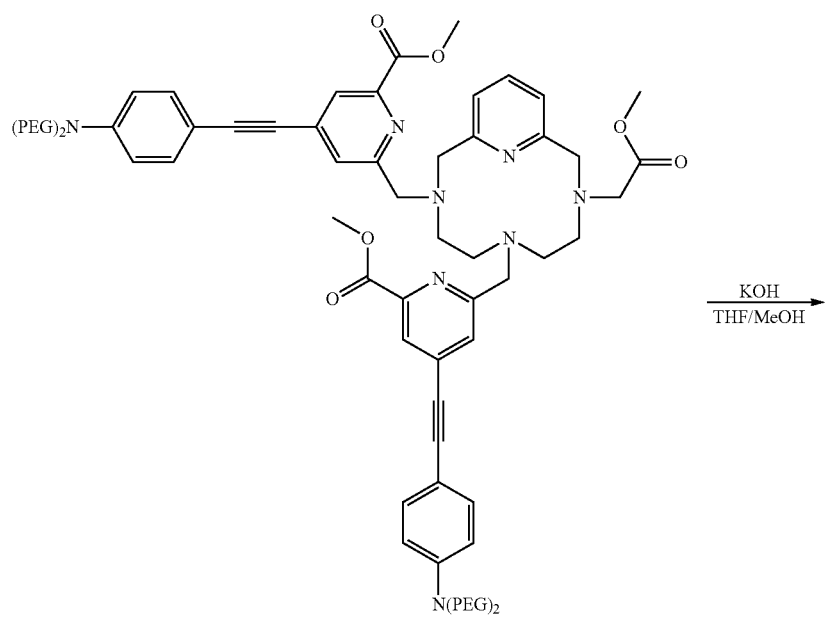

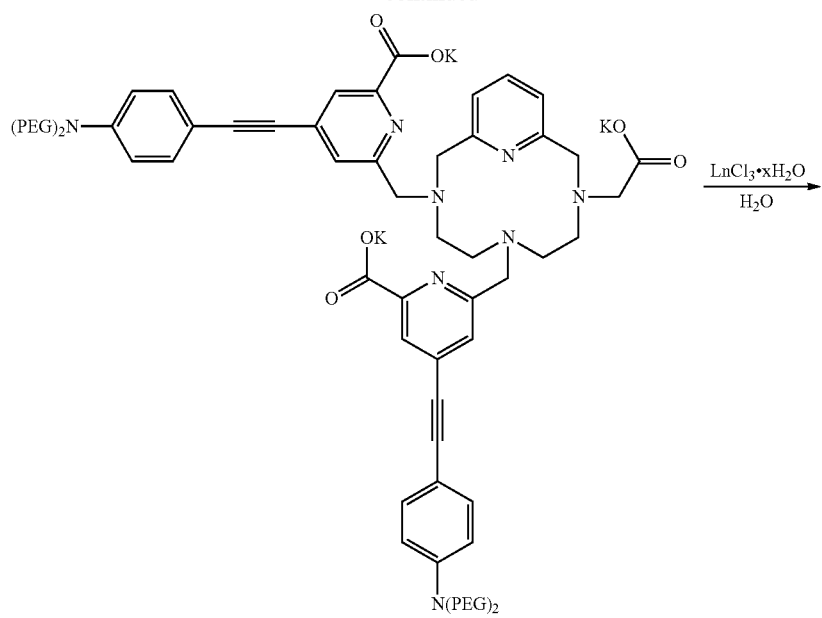
S2
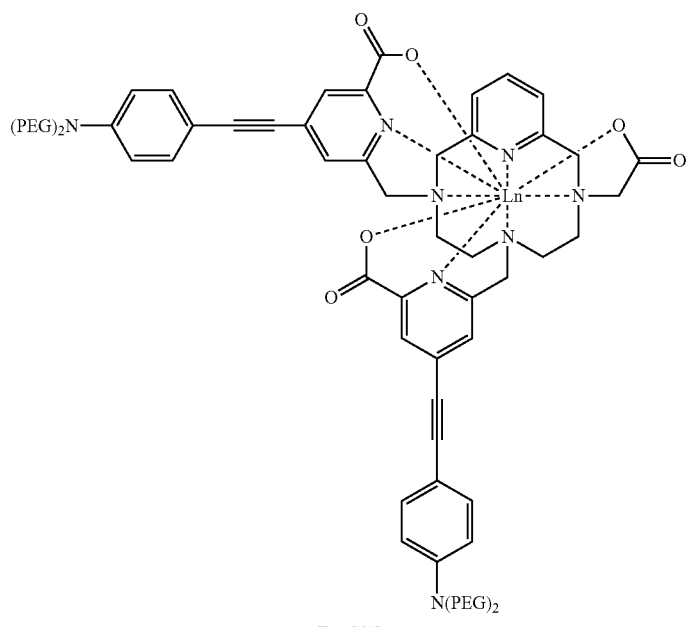
[Ln(S2)]
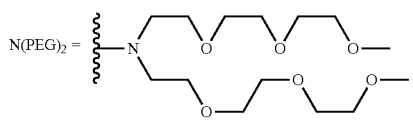

Methyl 4-((4-(bis(2-(2-(2-methoxyethoxy)ethoxy)ethyl)amino)phenyl)ethynyl)-6-(((methylsulfonyl)oxy)methyl)picolinate (I6)

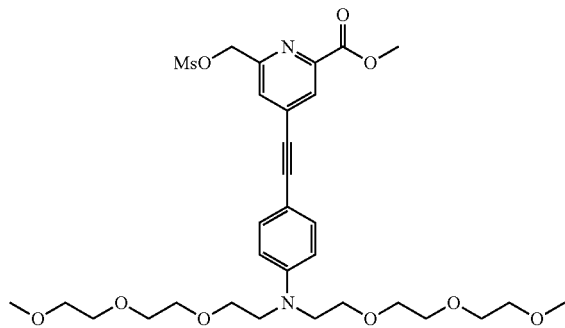

was synthesized as previously described (D'Aléo, A. et al., *Angewandte Chemie International Edition*, 2012, Vol. 51, pp. 6622-6625).

Synthesis of dimethyl 6,6'-((9-(2-methoxy-2-oxo-ethyl)-3,6,9-triaza-1(2,6)-pyridinacyclodecaphane-3,6-diyl)bis(methylene))bis(4-((4-(bis(2-(2-(2-methoxyethoxy)ethoxy)ethyl)amino)phenyl)ethynyl)picolinate) (E2)

A solution of compound I4 (92 mg, 0.33 mmol) and $K_2CO_3$ (183 mg, 1.32 mmol, 4 eq) in $CH_3CN$ (8.3 mL) was stirred at room temperature for 30 min. To this solution was added dropwise a solution of the mesylated antenna I6 (442 mg, 0.68 mmol, 2.05 eq) in $CH_3CN$ (12.3 mL). The reaction mixture was stirred at room temperature for 15 h and at 55° C. for 2 days before addition of 0.14 eq of the mesylated antenna I6. The reaction mixture was stirred at 55° C. for one more day and solvents were evaporated to dryness. The residue was taken up in $CH_2Cl_2$ and the residual salts were filtered on cotton. Solvents were evaporated to dryness. The residue was dissolved in the minimum of MeOH and a large excess of $Et_2O$ was added until the apparition of a yellow trouble. The solution was kept without stirring for two days and an oil was formed on the flask's walls. Solvents were removed and the oil in the flask was dissolved in $CHCl_3$ and solvents were evaporated to dryness to give compound E2 (102 mg, 0.073 mmol, 22%) as a brown oil. Rf (alumina, $CH_2Cl_2$/MeOH 100/2)=0.16. $^1H$ NMR spectrum could not be described because of its complexity. $^{13}C$ NMR (126 MHz, $CDCl_3$) δ 172.4, 165.5, 165.1, 159.3, 158.9, 158.5, 157.9, 148.8, 147.6, 137.6, 134.8, 133.6, 128.3, 125.3, 125.1, 122.1, 121.7, 111.4, 107.6, 98.7, 98.5, 84.7, 71.9, 70.7, 70.6, 70.5, 68.3, 63.4, 62.3, 61.8, 59.9, 59.0, 57.6, 54.2, 53.9, 53.7, 53.1, 52.9, 51.9, 51.9, 50.8, 50.8. ESI-HR-MS (positive, MeOH) m/z calcd. For $[C_{74}H_{103}NO_{18}]^+$: 1391.7385, found: 1391.7390, $[M+H]^+$; calcd. for $[C_{74}H_{104}N_8O_{18}]^{2+}$: 696.3729, found: 696.3741, $[M+2H]^{2+}$; calcd. for $[C_{74}H_{104}N_8O_{18}]^{3+}$: 464.5843, found: 464.5854, $[M+3H]^{3+}$.

Synthesis of potassium 6,6'-((9-(carboxylatomethyl)-3,6,9-triaza-1(2,6)-pyridinacyclodecaphane-3,6-diyl)bis(methylene))bis(4-((4-(bis(2-(2-(2-methoxyethoxy)ethoxy)ethyl)amino)phenyl)ethynyl)picolinate) (S2)

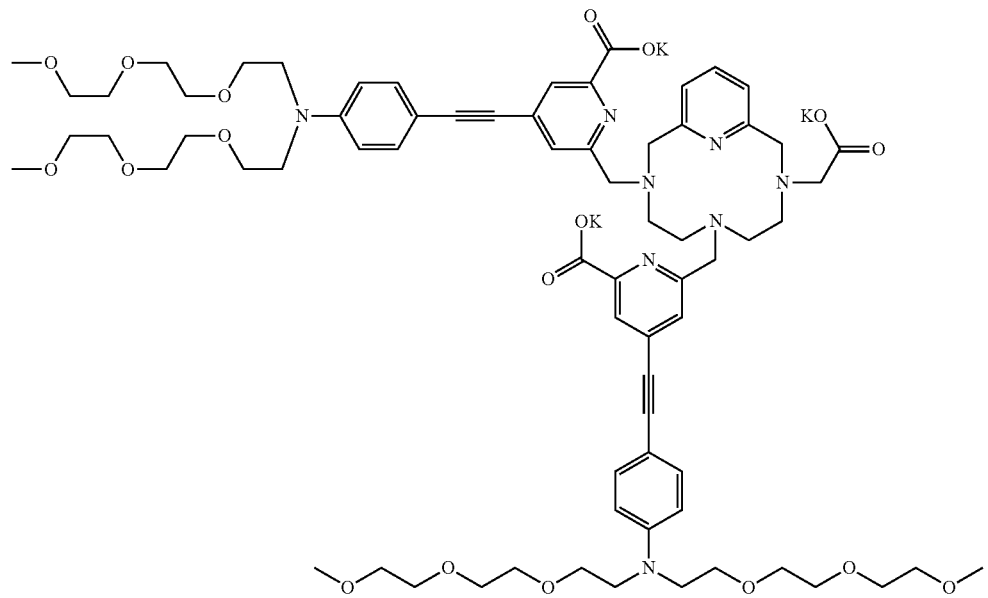

To a solution of compound E2 (89 mg, 63 μmol) in THF/MeOH (8/2 v/v, 4.3 mL) was added 1M KOH (850 μL). The reaction mixture was stirred at 65° C. for 1.5 days. Solvents were evaporated and the residue was submitted to a dialysis for 15 h (cut-off 100-500 Da) to give compound S2 (80 mg, 54 μmol, 85%) as a brown oil. $^1H$ NMR (500 MHz, $D_2O$): δ 7.82 (br s, 1H), 7.68-7.51 (m, 1H), 7.51-7.27 (m, 3H), 7.01 (s, 1H), 6.60 (d, J=6.9 Hz, 2H), 3.62-3.35 (m, 42H), 3.29 (2 s, 12H), some signals of the pyclen and the picolinate skeletons could not be observed. $^{13}$C NMR (126 MHz, D$_2$O): δ 173.9, 173.8, 162.7, 159.8, 157.1, 156.9, 156.5, 151.5, 141.2, 136.6, 136.5, 136.1, 128.7, 126.9, 126.5, 125.9, 114.6, 110.5, 110.4, 100.0, 88.9, 88.8, 73.9, 72.8, 72.4, 72.3, 70.6, 60.9, 52.9, some signals of the pyclen skeleton could not be observed. ESI-HR-MS (positive, H$_2$O) m/z calcd. for [C$_{71}$H$_{95}$FeN$_8$O$_{18}$]$^+$: 701.8151, found: 701.8065, [M−H+Fe]$^{2+}$; calcd. for [C$_{71}$H$_{96}$CaN$_8$O$_{18}$]$^+$: 694.3229, found: 694.3229, [M+Ca]$^{2+}$; calcd. for [C$_{71}$H$_{96}$FeN$_8$O$_{18}$]$^+$: 468.2059, found: 468.2070, [M+Fe]$^{3+}$; calcd. for [C$_{71}$H$_{97}$CaN$_8$O$_{18}$]$^{3+}$: 463.2177, found: 463.2186, [M+H+Ca]$^{3+}$.

Example 1-3: Synthesis of Ligand S3

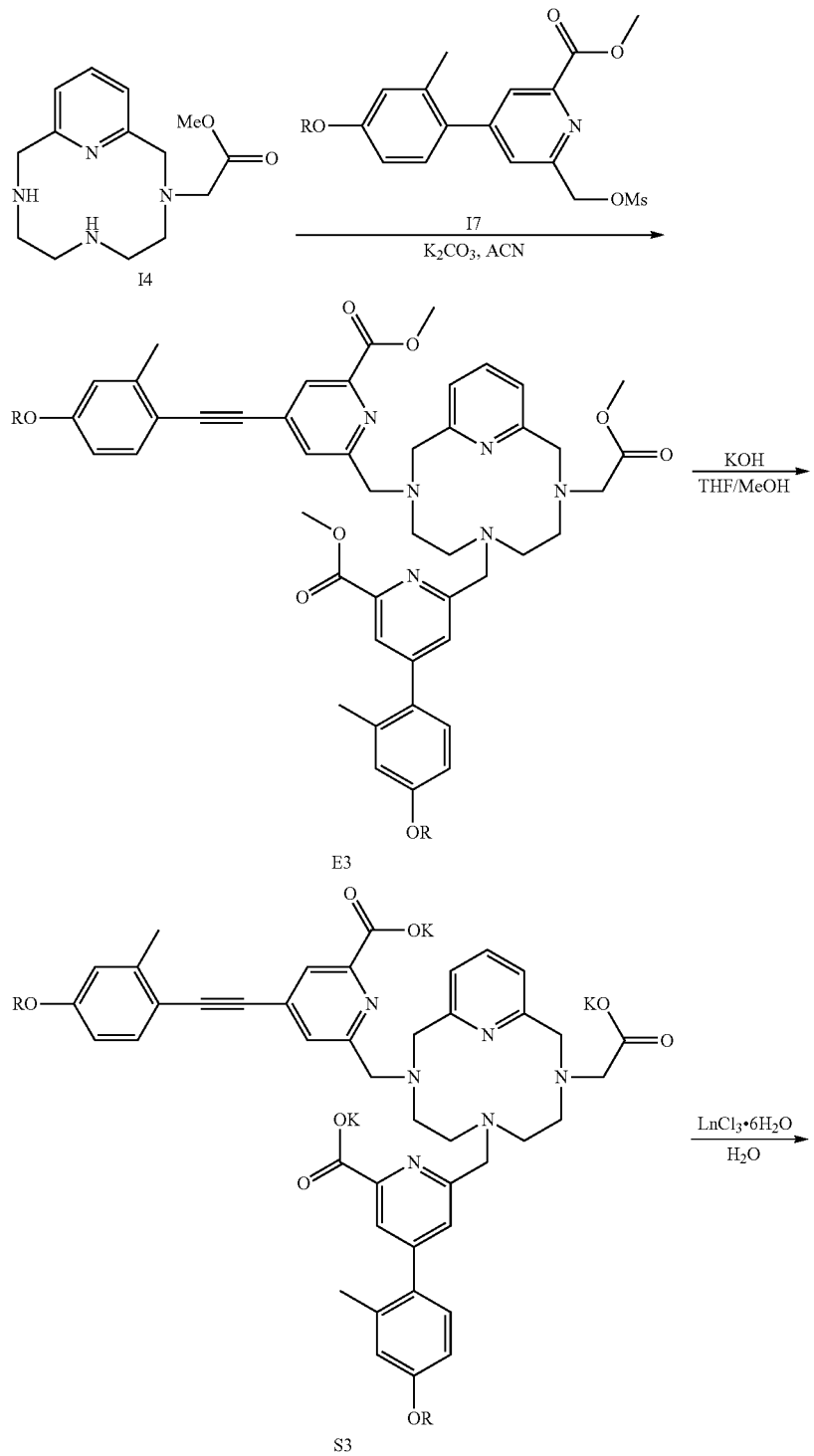

Scheme 3: Synthesis of the [Ln(S3)] complexes

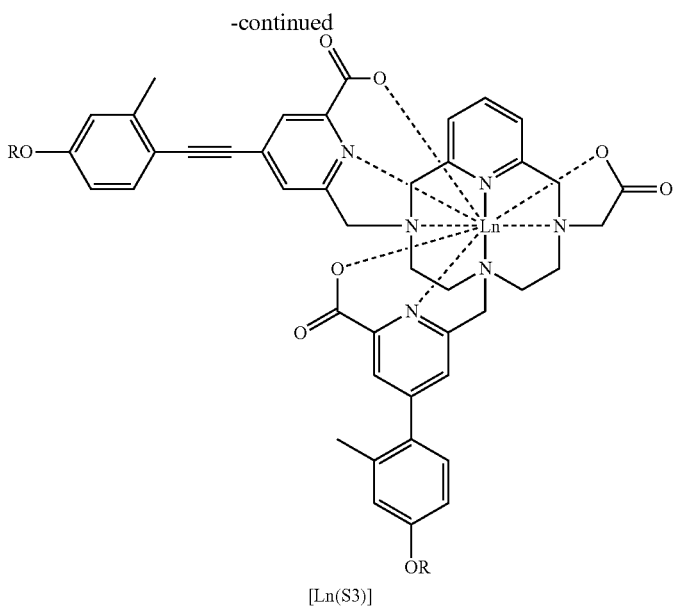

[Ln(S3)]

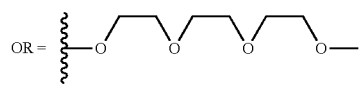

Methyl 4-(4-(2,5,8,11-tetraoxadodecyl)-2-methylphenyl)-6-(((methylsulfonyl)oxy)methyl)picolinate (I7)

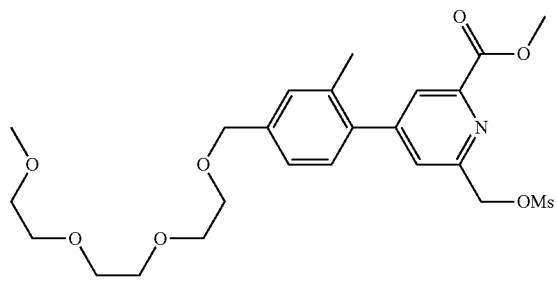

was synthesized as previously described (*Chemistry a European Journal*, 2018, Vol. 24, pp. 3408-3412).

Synthesis of dimethyl 6,6'-((9-(2-methoxy-2-oxoethyl)-3,6,9-triaza-1(2,6)-pyridinacyclodecaphane-3,6-diyl)bis(methylene))bis(4-(4-(2-(2-(2-methoxyethoxy)ethoxy)ethoxy)-2-methylphenyl)picolinate) (E3)

A solution of compound I4 (108 mg, 0.39 mmol) and $K_2CO_3$ (214 mg, 1.44 mmol, 4 eq) in $CH_3CN$ (9.7 mL) was stirred at room temperature for 30 min. To this solution was added dropwise a solution of the mesylated antenna I7 (398 mg, 0.80 mmol, 2.07 eq) in $CH_3CN$ (14.6 mL). The reaction mixture was stirred at 55° C. for 38 h, cooled down to room temperature, salts were filtrated on cotton and solvents were evaporated to dryness. The residue was taken up in dichloromethane and residual salts were filtered on cotton before evaporation of solvents to dryness. The residue was dissolved in the minimum of MeOH and a large excess of $Et_2O$ was added until the apparition of a white trouble. The solution was kept without stirring for two days and an oil was formed on the flask's walls. Solvents were removed and the oil in the flask was dissolved in $CHCl_3$ and solvents were evaporated to dryness. Purification of the residue by column chromatography (alumina, eluent $CH_2Cl_2$/MeOH 100/0.5 to 100/1.5) gave compound E3 (224 mg, 0.207 mmol, 53%) as a pale yellow oil. Rf (alumina, $CH_2Cl_2$/MeOH 100/2)=0.15. $^1H$ NMR (500 MHz, $CDCl_3$) δ 7.85 (s, 1H), 7.79 (s, 1H), 7.60 (t, J=7.7 Hz, 1H), 7.38 (s, 1H), 7.31 (s, 1H), 7.07 (m, 4H), 6.79 (m, 4H), 4.26 (d, J=14.5 Hz, 1H), 4.11 (dd, J=9.9, 5.6 Hz, 4H), 4.04 (dd, J=14.6, 10.2 Hz, 2H), 3.96 (s, 3H), 3.94-3.86 (m, 3H), 3.86-3.80 (m, 4H), 3.76 (d, J=15.4 Hz, 1H), 3.73-3.59 (m, 19H), 3.54-3.50 (m, 4H), 3.46 (m, 2H), 3.33 (s, 6H), 2.95 (t, J=12.0 Hz, 1H), 2.75-2.59 (m, 3H), 2.45-2.36 (m, 1H), 2.30 (m, 1H), 2.22 (s, 3H), 2.20 (s, 3H), 2.04 (m, 1H), 1.87-1.78 (m, 1H). $^{13}C$ NMR (126 MHz, $CDCl_3$) δ 171.8, 165.8, 165.0, 159.9, 159.3, 159.2, 158.9, 158.3, 157.9, 152.2, 152.1, 147.3, 147.2, 138.0, 136.4, 136.4, 136.3, 130.5, 130.1, 129.9, 127.2, 126.8, 124.3, 124.2, 121.4, 120.8, 117.0, 112.4, 71.8, 70.7, 70.5, 70.4, 69.5, 67.4, 62.9, 61.6, 61.4, 59.7, 58.9, 57.3, 55.8, 55.0, 52.9, 52.6, 51.7, 51.6, 20.5. ESI-HR-MS (positive, MeOH) m/z calcd. For $[C_{58}H_{77}N_6O_{14}]^+$: 1081.5492, found: 1081.5502, $[M+H]^+$; calcd. for $[C_{58}H_{76}N_6NaO_{14}]^+$: 1103.5311, found: 1103.5318, $[M+Na]^+$; calcd. for $[C_{58}H_{78}N_6O_{14}]^{2+}$: 541.2783, found: 541.2792, $[M+2H]^{2+}$.

Synthesis of potassium 6,6'-((9-(carboxylatomethyl)-3,6,9-triaza-1(2,6)-pyridinacyclodecaphane-3,6-diyl)bis(methylene))bis(4-(4-(2-(2-(2-methoxyethoxy)ethoxy)ethoxy)-2-methylphenyl)picolinate) (S3)

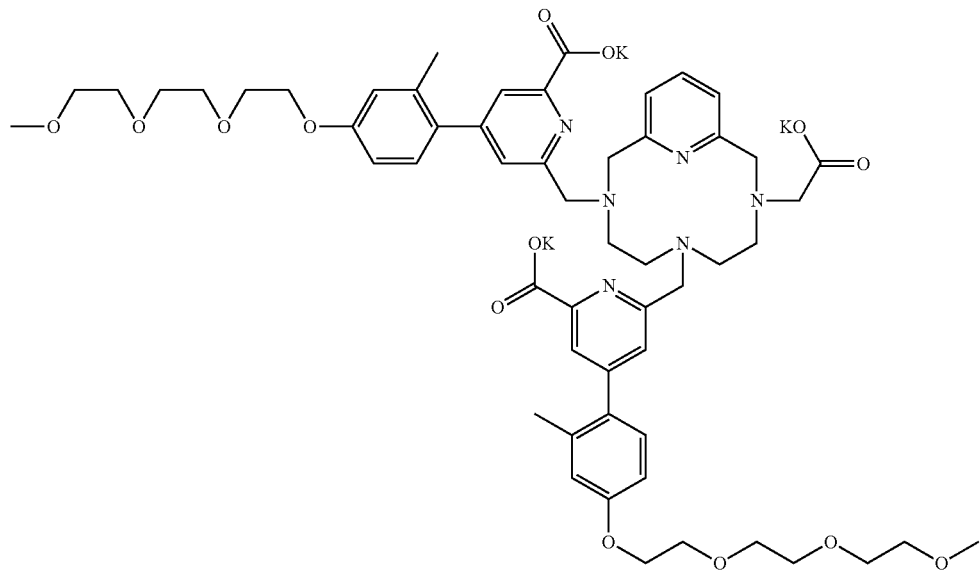

To a solution of compound E3 (80 mg, 74 μmol) in THF/MeOH (8/2 v/v, 4.9 mL) was added 1M KOH (990 μL). The reaction mixture was stirred at 65° C. for 44 h. Solvents were evaporated and the residue was submitted to a dialysis for 16 h (cut-off 100-500 Da) to give S3 (41 mg, 35 μmol, 48%) as a pale yellow oil. $^1$H NMR (500 MHz, D$_2$O): δ 7.80 (s, 1H), 7.53 (s, 1H), 7.37 (m, 2H), 6.85 (d, J=7.7 Hz, 1H), 6.71-6.61 (m, 5H), 6.61-6.53 (m, 2H), 6.14 (d, J=8.4 Hz, 1H), 4.59 (s, 2H), 4.13 (m, 2H), 4.09-4.01 (m, 2H), 3.90-3.83 (m, 4H), 3.79-3.52 (m, 28H), 3.34 (s, 3H), 3.33 (s, 3H), 3.28 (s, 2H), 2.99 (s, 2H), 1.91 (s, 3H), 1.84 (s, 3H). $^{13}$C NMR (126 MHz, D$_2$O): δ 181.3, 175.1, 174.7, 162.2, 161.6, 160.9, 160.8, 160.0, 156.6, 155.7, 154.2, 154.0, 153.1, 140.8, 139.8, 139.8, 133.7, 133.5, 133.0, 132.9, 129.4, 128.2, 127.5, 125.7, 123.2, 122.9, 119.8, 119.8, 115.1, 114.4, 73.9, 73.8, 72.6, 72.5, 72.4, 72.3, 72.2, 71.8, 71.7, 69.9, 69.8, 65.9, 62.1, 61.1, 60.9, 59.2, 58.6, 58.3, 55.0, 52.3, 22.6, 22.4. ESI-HR-MS (positive, H$_2$O) m/z calcd. for [C$_{55}$H$_{71}$N$_6$O$_{14}$]$^+$: 1039.5023, found: 1039.5031, [M+H]$^+$; calcd. for [C$_{55}$H$_{69}$CaN$_6$O$_{14}$]$^+$: 1077.4492, found: 1077.4500, [M−H+Ca]$^+$; calcd. for [C$_{55}$H$_{72}$N$_6$O$_{14}$]$^{2+}$: 520.2548, found: 520.2562, [M+2H]$^{2+}$; calcd. for [C$_{55}$H$_{70}$CaN$_6$O$_{14}$]$^{2+}$: 539.2282, found: 539.2297, [M+Ca]$^{2+}$; calcd. for [C$_{55}$H$_{69}$FeN$_6$O$_{14}$]$^{2+}$: 546.7105, found: 546.7127, [M−H+Fe]$^{2+}$.

Example 1-4: Synthesis of Ligand S4

Scheme 4: Synthesis of the [Eu(S4)] complexes

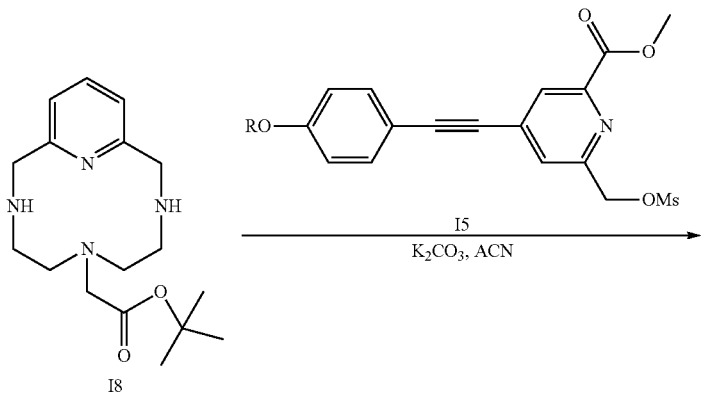

-continued
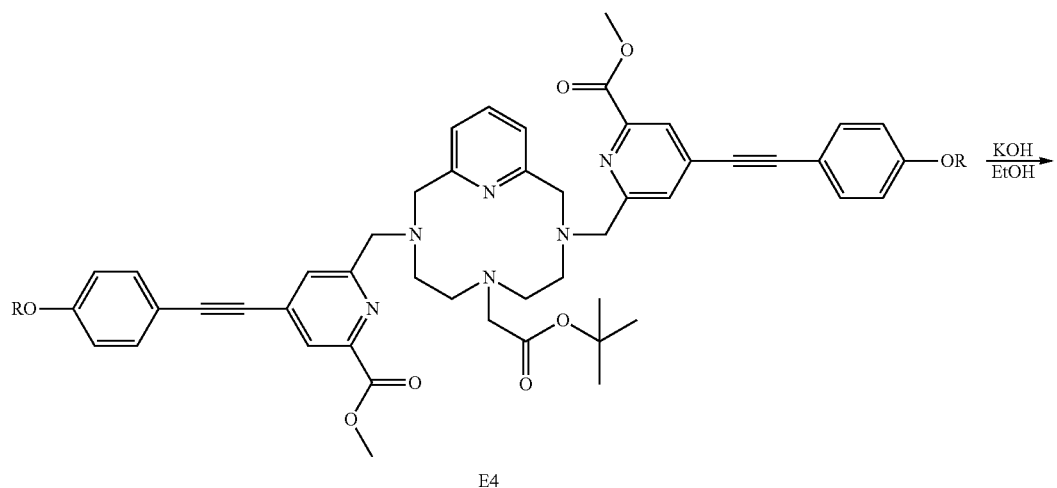
E4
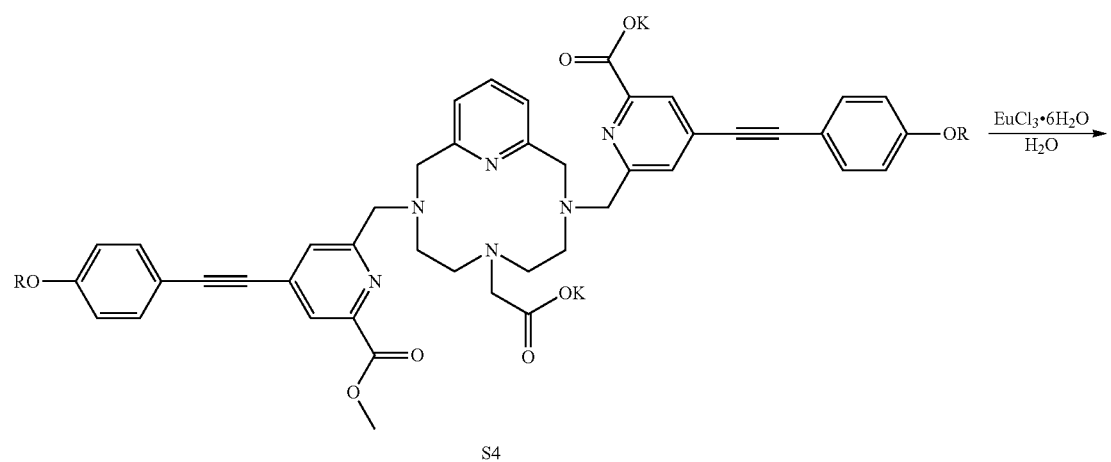
S4
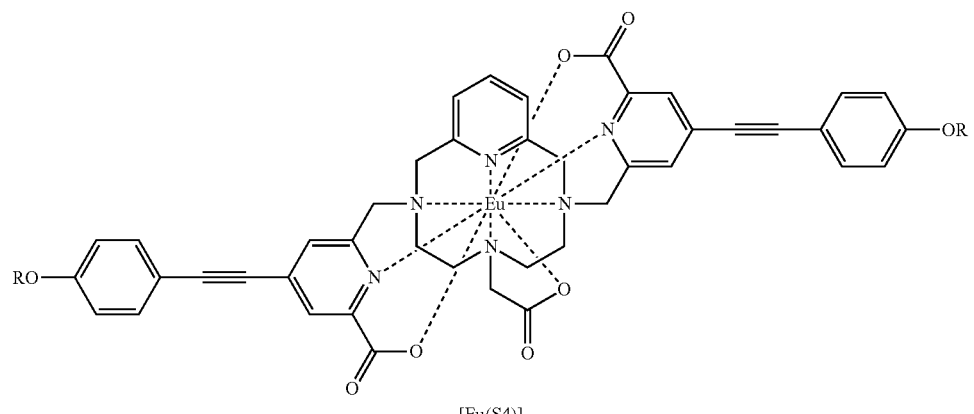
[Eu(S4)]
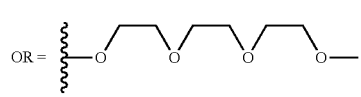

Tert-butyl 2-(3,6,9-triaza-1(2,6)-pyridinacyclodecaphane-6-yl)acetate (I8)

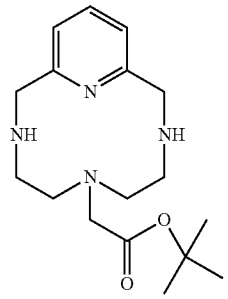 [SMILES: CC(C)(C)OC(=O)CN1CCNCc2cccc(n2)CNCC1]

was synthesized as previously described (Tetrahedron, 2001, Vol. 57, pp. 4713-4718). Methyl 4-((4-(2-(2-(2-methoxyethoxy)ethoxy)ethoxy)phenyl)ethynyl)-6-(((methylsulfonyl)oxy)methyl)picolinate (I5) was synthesized as previously described (Walton, J. W., et al., *Chemical Communications*, 2013, Vol. 49, No. 16, pp. 1600-1602).

Synthesis of dimethyl 6,6'-((6-(2-methoxy-2-oxoethyl)-3,6,9-triaza-1(2,6)-pyridinacyclodecaphane-3,9-diyl)bis(methylene))bis(4-((4-(2-(2-(2-methoxyethoxy)ethoxy)ethoxy)phenyl)ethynyl)picolinate) (E4)

A solution of compound I8 (113 mg, 0.35 mmol), $K_2CO_3$ (195 mg, 1.41 mmol, 4 eq) and NaI (108 mg, 0.73 mmol, 2.05 eq) in $CH_3CN$ (8.8 mL) was stirred at room temperature for 30 min. To this solution was added dropwise a solution of the mesylated antenna I5 (365 mg, 0.72 mmol, 2.05 eq) in $CH_3CN$ (13.2 mL). The reaction mixture was stirred at 60° C. for 3.5 days, cooled down to room temperature, salts were filtrated on cotton and solvents were evaporated to dryness. The residue was taken up in dichloromethane and residual salts were filtered on cotton before evaporation of solvents to dryness. NMR and mass analysis of this residue showed that it was a mixture of the mono- and di-alkylated compounds. 154 mg of this mixture and $K_2CO_3$ (58 mg, 0.42 mmol) were dissolved in $CH_3CN$ (7 mL) and the reaction mixture was stirred at 50° C. for 30 min. To this solution was added dropwise a solution of the mesylated antenna I5 (140 mg, 0.28 mmol) in $CH_3CN$ (7 m). The reaction mixture was stirred at reflux for 40 h before evaporation of solvents to dryness. The residue was taken up in dichloromethane and residual salts were filtered on cotton before evaporation of solvents to dryness. The residue was dissolved in the minimum of MeOH and a large excess of $Et_2O$ was added until the apparition of a white trouble. The solution was kept without stirring for two days and an oil was formed on the flask. Solvents were removed, the oil in the flask was dissolved in $CHCl_3$ and solvents were evaporated to dryness to give E4 (136 mg, 0.12 mmol, 33%) as a brown oil. $^1$H NMR (300 MHz, $CDCl_3$): The 1H NMR spectra could not be fully described because of its complexity: δ 7.97 (s, 1H), 7.61 (s, 2H), 7.48 (m, ?H), 7.09 (d, J=7.7 Hz, 2H), 6.91 (m, ?H), 4.37-3.47 (m, ?H), 3.37 (s, 12H), 2.92 (m, ?H), 2.61 (m, ?H), 1.79 (m, ?H), 1.32 (s, 9H). $^{13}$C NMR (75 MHz, $CDCl_3$) δ 170.5, 165.0, 159.9, 159.0, 158.7, 146.7, 137.9, 134.5, 133.5, 127.9, 125.2, 120.4, 114.8, 113.3, 96.8, 84.7, 81.7, 71.7, 70.6, 70.4, 70.3, 69.4, 67.4, 67.4, 62.7, 62.1, 58.8, 54.8, 53.7, 52.8, 27.9. ESI-HR-MS (positive, MeOH) m/z calcd. For $[C_{63}H_{79}N_6O_{14}]^+$: 1143.5649, found: 1143.5648, $[M+H]^+$; calcd. for $[C_{63}H_{78}N_6NaO_{14}]^+$: 1165.5468, found: 1165.5470, $[M+Na]^+$; calcd. for $[C_{63}H_{80}N_6O_{14}]^{2+}$: 572.2861, found: 572.2869, $[M+2H]^{2+}$.

Synthesis of potassium 6,6'-((6-(carboxylatomethyl)-3,6,9-triaza-1(2,6)-pyridinacyclodecaphane-3,9-diyl)bis(methylene))bis(4-((4-(2-(2-(2-methoxyethoxy)ethoxy)ethoxy)phenyl)ethynyl)picolinate) (S4)

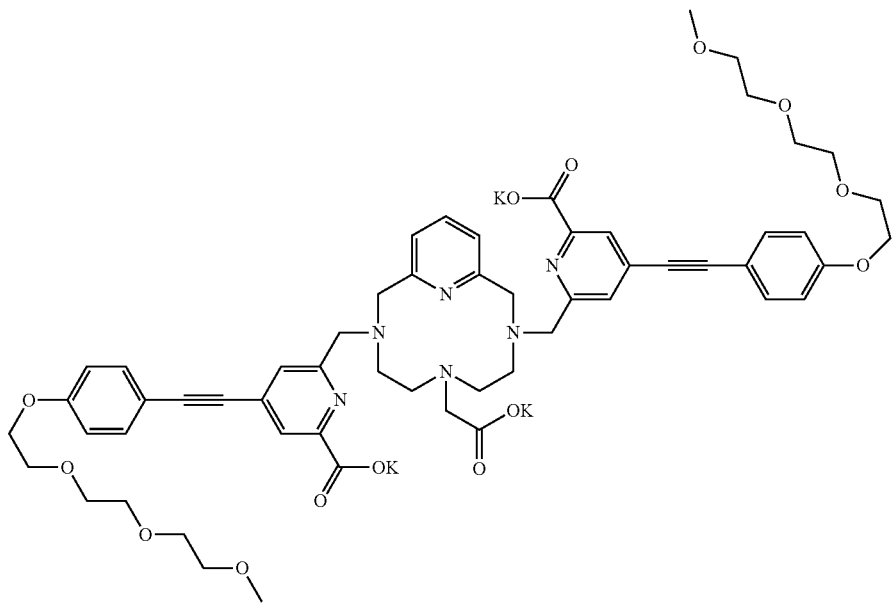

To a solution of compound E4 (52 mg, 47 μmol) in EtOH (1 mL) was added 1M KOH (2 mL). The reaction mixture was stirred at reflux for 29 h. Solvents were evaporated and the residue was submitted to a dialysis for 14 h (cut-off 100-500 Da) to give S4 (30 mg, 25 μmol, 54%) as a pale brown oil. $^1$H NMR spectrum was recorded but could not be described because of its complexity. $^{13}$C NMR (126 MHz, D$_2$O) δ 173.9, 173.3, 162.3, 161.8, 160.9, 156.3, 136.4, 135.9, 135.5, 128.9, 126.7, 122.8, 117.6, 116.3, 97.3, 88.7, 73.8, 72.5, 72.4, 72.2, 71.7, 65.5, 60.9, 55.0, 53.8, 51.5 some signal of the pyclen skeleton could not been observed.

ESI-HR-MS (positive, H$_2$O) m/z calcd. for [C$_{57}$H$_{64}$FeN$_6$O$_{14}$]$^+$: 1112.3824, found: 1112.3829, [M−2H+Fe]$^+$; calcd. for [C$_{57}$H$_{66}$NaN$_6$O$_{14}$]$^{2+}$: 549.2126, found: 549.2133, [M+Ca]$^{2+}$; calcd. for [C$_{57}$H$_{65}$FeN$_6$O$_{14}$]$^{2+}$: 556.6948, found: 556.6963, [M−H+Fe]$^{2+}$.

Example 1-5: Synthesis of Compounds I17 and I18

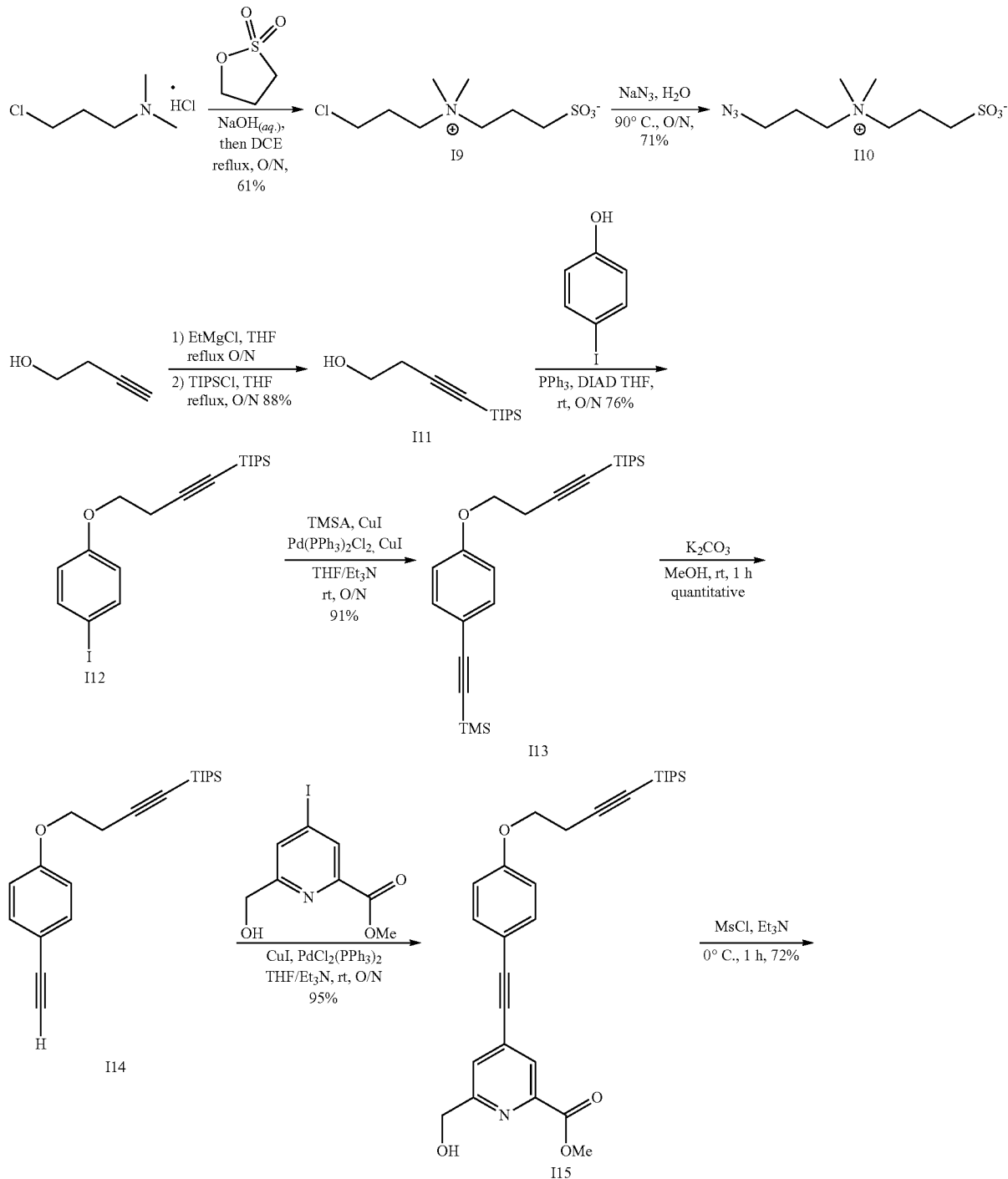

Scheme 5: Synthesis of compounds I17 andf I18

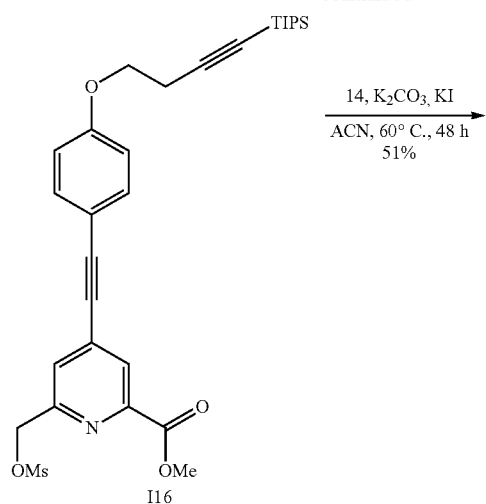
I16
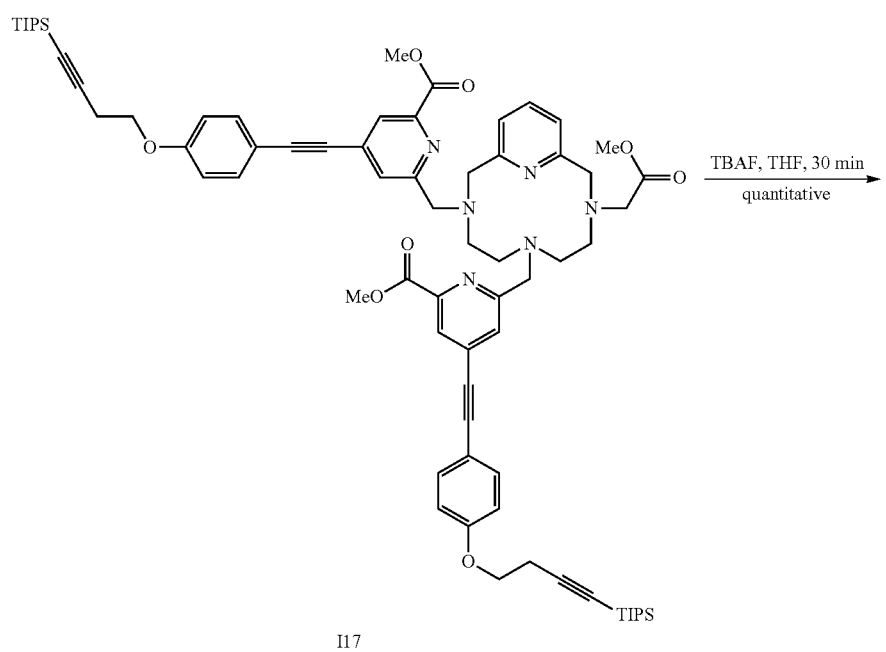
I17

-continued

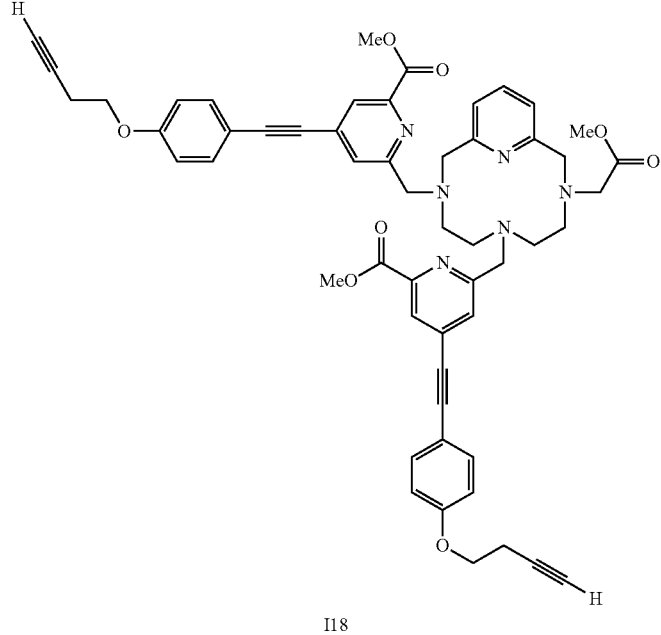 [SMILES: C#CCCOc1ccc(C#Cc2cc(CN3CCN(CC(=O)OC)Cc4cccc(n4)CN(Cc4cc(C#Cc5ccc(OCCC#C)cc5)cc(C(=O)OC)n4)CC3)nc(C(=O)OC)c2)cc1 ; "I18"]

I18

3-((3-chloropropyl)dimethylammonio)propane-1-sulfonate (I9)

ClC$_3$H$_6$N(CH$_3$)$_2$·HCl (3.16 g, 20.0 mmol, 1.0 eq.) was dissolved in 2 mL of NaOH$_{(aq)}$ solution (40%, w/v) and the suspension was stirred for 30 min. ClC$_3$H$_6$N(CH$_3$)$_2$ was collected using a separatory funnel and the aqueous phase was extracted with 5 mL of DCE. The organic layers were combined and dried over Na$_2$SO$_4$. 15 mL of DCE was further added, followed by 1,3-propanesultone (3.66 g, 30.0 mmol, 1.5 eq.), and the reaction mixture was refluxed at 70° C. overnight. The crude was cooled down and the formed precipitate was filtered, washed with 3*25 mL of DCM, and dried under vacuum to afford the pure product I9 as a white solid (2.95 g, 61%). $^1$H NMR (400 MHz, D$_2$O) δ: 3.79 (t, J=8.0 Hz, 2H), 3.63-3.55 (m, 4H), 3.21 (s, 6H), 3.06 (t, J=8.0 Hz, 2H), 2.41-2.28 (m, 4H). $^{13}$C NMR (100 MHz, D$_2$O) δ: 62.7, 61.9, 50.8, 47.3, 41.2, 25.2, 12.8. ESI-MS (positive, H$_2$O) m/z calcd. for [C$_8$H$_{19}$ClNO$_3$S]$^+$: 244.1, found: 244.0 [M+H]$^+$.

3-((3-azidopropyl)dimethylammonio)propane-1-sulfonate (I10)

NaN$_3$ (0.16 g, 2.48 mmol, 2.0 eq.) was added to an aqueous solution of I9 (0.30 g, 1.24 mmol, 1.0 eq.) in water (6 mL) under a nitrogen atmosphere. The reaction was stirred at 90° C. overnight. The mixture was cooled down and water was evaporated under vacuum. The white solid was washed by cold methanol and dried to yield the pure desired product I10 as a white solid (0.25 g, 71%). 1H NMR (400 MHz, D2O) δ: 3.62-3.51 (m, 6H), 3.22 (s, 6H), 3.08 (t, J=8.0 Hz, 2H), 2.36-2.28 (m, 2H), 2.21-2.14 (m, 2H). 13C NMR (100 MHz, D2O) δ: 62.5, 61.8, 50.8, 47.3, 47.3, 22.1, 18.4. ESI-MS (positive, H2O) m/z calcd. for [C8H18N4O3SNa]+: 273.1, found: 272.8 [M+Na]+.

4-(triisopropylsilyl)but-3-yn-1-ol (I11)

To a solution of 4-butyn-1-ol (2.50 mL, 2.25 g, 32.1 mmol, 1.0 eq.) in dry THF (25 mL) under argon was added ethylmagnesium chloride (2.1 M in THF, 27 mL, 67.4 mmol, 2.1 eq.) over 10 minutes at room temperature. The mixture was refluxed for 12 hours resulting in a cloudy white solution. The reaction was cooled to room temperature and a solution of triisopropylchlorosilane (6.88 mL, 6.20 g, 32.1 mmol, 1.0 eq.) in THF (25 mL) was added over a period of 10 minutes. The mixture was refluxed overnight. The reaction was cooled to room temperature, poured into 10% HCl, extracted with ether, dried over MgSO$_4$, filtered, and concentrated to a brown oil. Purification by vacuum distillation afforded I11 (6.36 g, 88%) as a colorless oil. $^1$H NMR (400 MHz, CDCl$_3$) δ: 3.70 (t, J=8.0 Hz, 2H), 2.51 (t, J=8.0 Hz, 2H), 1.05 (br m, 3H), 1.03 (s, 18H). $^{13}$C NMR (100 MHz, CDCl$_3$) δ: 105.0, 83.0, 61.2, 24.4, 18.6, 17.7.

(4-(4-iodophenoxy)but-1-yn-1-yl)triisopropylsilane (I12)

4-(triisopropylsilyl)but-3-yn-1-ol (I11) (4.62 g, 20.0 mmol, 2.5 eq.), 4-iodophenol (1.80 g, 8.00 mmol, 1.0 eq.), and triphenylphosphine (5.42 g, 20.0 mmol, 2.5 eq.) were dissolved in 20 mL of anhydrous THF under argon via sonication. The solution was cooled to 0° C. and diisopropyl azodicarboxylate (DIAD) (4.18 mL, 20.0 mmol, 2.5 eq.) was added dropwise via syringe. The resulting mixture was warmed up to rt and stirred overnight. The crude was concentrated in vacuo and the residue was directly submitted to flash column chromatography (SiO$_2$, 10:0 to 8:2 CyHx-EA) to yield I12 as a colorless oil (2.60 g, 76%). $^1$H NMR (400 MHz, CDCl$_3$) δ: 7.54 (d, J=8.0 Hz, 2H), 6.68 (d, J=8.0 Hz, 2H), 4.03 (t, J=8.0 Hz, 2H), 2.72 (t, J=8.0 Hz, 2H), 1.06 (br m, 3H), 1.05 (s, 18H). $^{13}$C NMR (100 MHz, CDCl$_3$) δ: 158.4, 138.3, 117.1, 104.0, 83.1, 82.6, 66.5, 20.9, 18.6, 11.2.

Triisopropyl(4-(4-((trimethylsilyl)ethynyl)phenoxy)but-1-yn-1-yl)silane (I13)

Ethynyltrimethylsilane (0.92 mL, 0.66 g, 6.53 mmol, 2.5 eq.) and I12 (1.14 g, 2.61 mmol, 1.0 eq.) were dissolved in a mixture of anhydrous THF (14 mL) and triethylamine (12 mL). The solution was degassed with argon and followed by the addition of CuI (58.0 mg, 0.287 mmol, 11 mol %) and PdCl$_2$(PPh$_3$)$_2$ (94.0 mg, 0.131 mmol, 5 mol %). The reaction mixture was stirred at rt overnight. The volatiles were removed under reduced pressure and the resulting brown oil was purified by column chromatography (SiO$_2$, 10:0 to 8:2 CyHx-EA) to afford I13 as a white solid (950 mg, 91%). $^1$H NMR (400 MHz, CDCl$_3$) δ: 7.40 (d, J=8.0 Hz, 2H), 6.82 (d, J=8.0 Hz, 2H), 4.09 (t, J=8.0 Hz, 2H), 2.74 (t, J=8.0 Hz, 2H), 1.07 (br m, 18H+3H), 0.24 (s, 9H). $^{13}$C NMR (100 MHz, CDCl$_3$) δ: 158.7, 133.5, 115.6, 114.5, 105.2, 104.0, 92.6, 82.6, 66.4, 20.9, 18.6, 11.2, 0.1.

(4-(4-ethynylphenoxy)but-1-yn-1-yl)triisopropylsilane (I14)

I13 (900 mg, 2.22 mmol, 1.0 eq.) was mixed with K$_2$CO$_3$ (375 mg, 2.66 mmol, 1.2 eq.) in 44 mL of methanol. The suspension was stirred at rt for 1 h. The volatiles were removed under reduced pressure and the crude was re-dissolved in DCM and washed with water, yielding the pure adduct I14 quantitatively (720 mg) after removal of DCM by rotary evaporation. $^1$H NMR (400 MHz, CDCl$_3$) δ: 7.40 (d, J=8.0 Hz, 2H), 6.84 (d, J=8.0 Hz, 2H), 4.09 (t, J=8.0 Hz, 2H), 2.99 (s, 1H), 2.74 (t, J=8.0 Hz, 2H), 1.06 (br m, 18H+3H). $^{13}$C NMR (100 MHz, CDCl$_3$) δ: 158.9, 133.6, 114.6, 114.4, 103.9, 83.6, 82.6, 75.8, 66.4, 20.9, 18.6, 11.2.

Methyl-6-(hydroxymethyl)-4-((4-((4-(triisopropylsilyl)but-3-yn-1-yl)oxy)phenyl)ethynyl)picolinate (I15)

Methyl 6-(hydroxymethyl)-4-iodopicolinate (957 mg, 3.05 mmol, 1.3 eq.) and I14 (700 mg, 2.35 mmol, 1.0 eq.) were dissolved in a mixture of anhydrous THF (17 mL) and triethylamine (13 mL). The solution was degassed with argon and followed by the addition of CuI (50.0 mg, 0.258 mmol, 11 mol %) and PdCl$_2$(PPh$_3$)$_2$ (85.0 mg, 0.117 mmol, 5 mol %). The reaction mixture was stirred at rt overnight. The volatiles were removed under reduced pressure and the resulting brown oil was purified by column chromatography (SiO$_2$, 10:0 to 95:5 DCM-MeOH) to afford I15 as a white solid (1100 mg, 95%). $^1$H NMR (300 MHz, CDCl$_3$) δ: 7.96 (s, 1H), 7.75 (s, 1H), 7.49 (d, J=8.0 Hz, 2H), 6.95 (d, J=8.0 Hz, 2H), 4.76 (s, 2H), 4.13 (t, J=8.0 Hz, 2H), 3.98 (s, 3H), 2.76 (t, J=8.0 Hz, 2H), 1.09 (br m, 18H+3H). ESI-MS (positive, MeOH) m/z calcd. for [C$_{29}$H$_{38}$NO$_4$Si]$^+$: 492.7, found: 492.8 [M+H]$^+$.

Methyl-6-(((methylsulfonyl)oxy)methyl)-4-((4-((4-(triisopropylsilyl)but-3-yn-1-yl)oxy)phenyl)ethynyl)picolinate (I16)

I15 (1000 mg, 2.00 mmol, 1.0 eq.) was dissolved in anhydrous THF (20 mL) and Et$_3$N (0.85 mL, 6.0 mmol, 3.0 eq.) was added. The mixture was stirred at 0° C. and methanesulfonyl chloride (207 µL, 2.60 mmol, 1.3 eq.) was added subsequently. The reaction was monitored by TLC and stopped upon completion (around 1 h). The solvent was removed under reduced pressure and the residue was dissolved in DCM (15 mL) and washed with NaCl solution (saturated, 10 mL). The aqueous layer was re-extracted with DCM (3*10 mL). The organic layers were combined, dried over MgSO$_4$, and the solvent was removed under reduced pressure. The crude was purified by column chromatography (SiO$_2$, 10:0 to 95:5 DCM-MeOH) to afford I16 as a colorless oil (820 mg, 72%). $^1$H NMR (400 MHz, CDCl$_3$) δ: 8.14 (s, 1H), 7.70 (s, 1H), 7.50 (d, J=8.0 Hz, 2H), 6.91 (d, J=8.0 Hz, 2H), 5.41 (s, 2H), 4.13 (t, J=8.0 Hz, 2H), 4.01 (s, 3H), 3.16 (s, 3H), 2.75 (t, J=8.0 Hz, 2H), 1.05 (br m, 18H+3H). $^{13}$C NMR (100 MHz, CDCl$_3$) δ: 164.8, 159.7, 154.5, 147.8, 134.6, 133.7, 126.6, 126.3, 114.9, 113.7, 103.8, 96.7, 84.9, 82.7, 70.6, 66.4, 53.1, 38.0, 20.8, 18.5, 11.1. ESI-MS (positive, MeOH) m/z calcd. for [C$_{30}$H$_{40}$NO$_6$SSi]$^+$: 570.2, found: 570.5 [M+H]$^+$.

Synthesis of dimethyl 6,6'-((9-(2-methoxy-2-oxoethyl)-3,6,9-triaza-1(2,6)-pyridinacyclodecaphane-3,6-diyl)bis(methylene))bis(4-((4-((4-(triisopropylsilyl)but-3-yn-1-yl)oxy)phenyl)ethynyl)picolinate)) (I17)

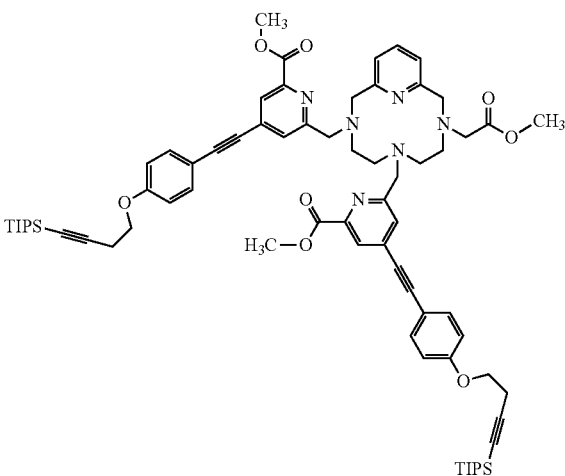

A solution of adduct I4 (80 mg, 0.28 mmol, 1.0 eq.) and K$_2$CO$_3$ (200 mg, 1.40 mmol, 5 eq) in ACN (4.5 mL) was stirred at room temperature for 30 min. To this solution was added dropwise a solution of compound I16 (405 mg, 0.70 mmol, 2.5 eq) in ACN (14 mL). The reaction mixture was stirred at 60° C. for 48 h and the solvents were evaporated to dryness. The residue was taken up in DCM and the residual salts were filtered off. Solvents were evaporated under pressure and the crude was purified by chromatography on neutralized silica (eluent: DCM/MeOH/NH$_3$ 99/1/0.1 to 96/4/0.6) to give the pure ligand I17 (175 mg, 51%) as a brown oil. $^{13}$C NMR (100 MHz, CDCl$_3$) δ 171.9, 165.6, 164.8, 160.6, 159.8, 159.8, 159.1 158.8, 158.1, 147.6, 147.6, 138.2, 134.8, 134.6, 133.9, 133.8, 128.3, 127.9, 125.4, 125.1, 121.6, 121.1, 115.0, 113.7, 113.6, 103.9, 97.3, 96.8, 85.0, 84.9, 66.5, 62.9, 61.7, 61.6, 59.8, 57.4, 56.1, 55.1, 53.2, 52.8, 51.8, 51.6, 21.0, 18.6, 11.2. ESI-MS (positive, MeOH) m/z calcd. for [C$_{72}$H$_{93}$N$_6$O$_8$Si$_2$]$^+$: 1225.6, found: 1225.3 [M+H]$^+$.

Synthesis of dimethyl 6,6'-((9-(2-methoxy-2-oxo-ethyl)-3,6,9-triaza-1(2,6)-pyridinacyclodecaphane-3,6-diyl)bis(methylene))bis(4-((4-(but-3-yn-1-yloxy)phenyl)ethynyl)picolinate) (I18)

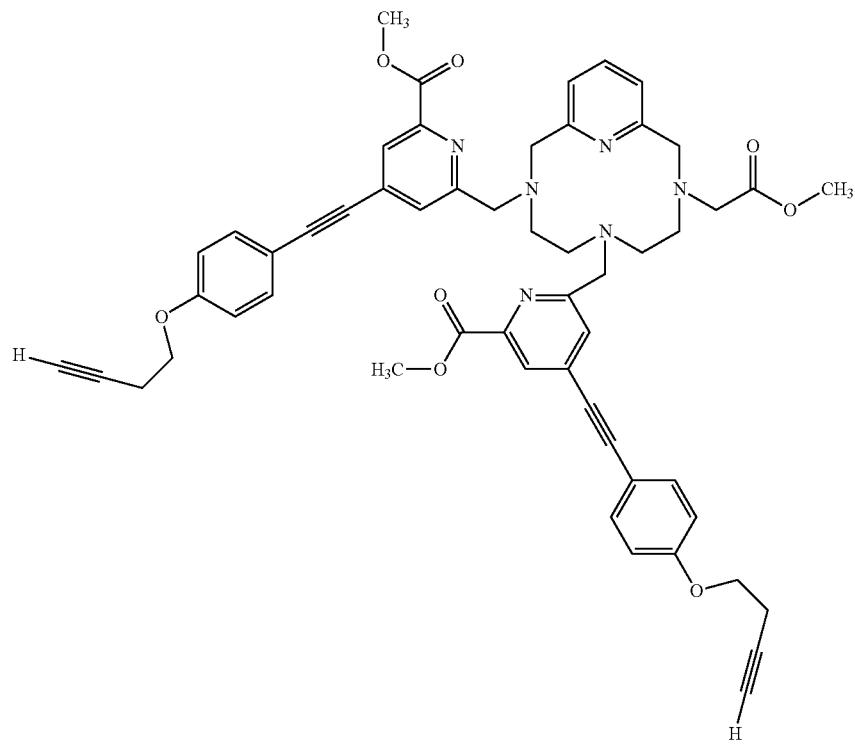 [SMILES: C#CCCOc1ccc(C#Cc2cc(CN3CCN(CC(=O)OC)Cc4cccc(n4)CN(Cc4cc(C#Cc5ccc(OCCC#C)cc5)cc(C(=O)OC)n4)CC3)nc(C(=O)OC)c2)cc1]

To a solution of I17 (25.0 mg, 20 mmol, 1.0 eq.) in tetrahydrofuran (1.0 mL) was added tetrabutylammonium fluoride (1.0 M in tetrahydrofuran, 50 µL, 50 mmol, 2.5 eq.) at room temperature. The mixture was stirred at the same temperature and the reaction was followed by LCMS until completion (around 30 min). The mixture was poured into water, extracted three times with DCM, dried over Na$_2$SO$_4$ and concentrated under pressure. The product I18 was used in the following reaction without further purification. ESI-MS (positive, MeOH) m/z calcd. for [C$_{54}$H$_{53}$N$_6$O$_8$]$^+$: 913.4, found: 913.3 [M+H]$^+$.

Example 1-6: Synthesis of Ester E6

Scheme 6: Synthesis of ester E6

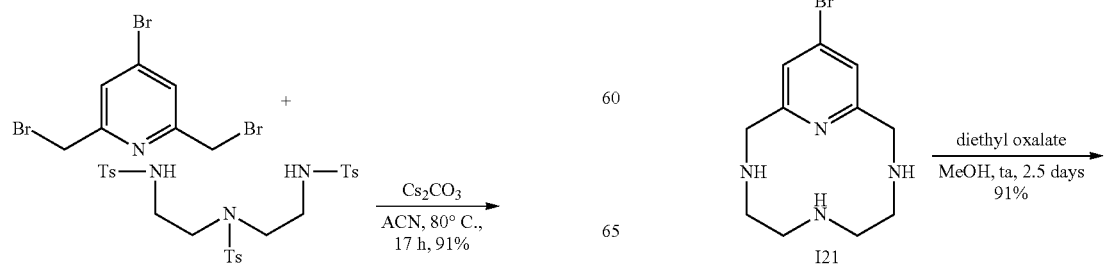

-continued

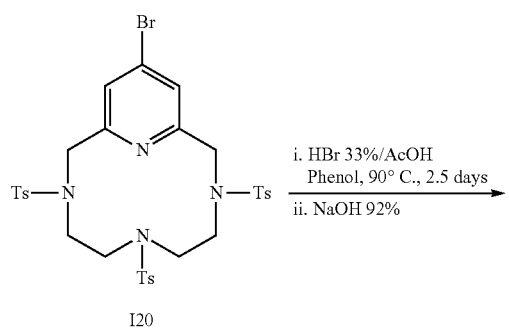

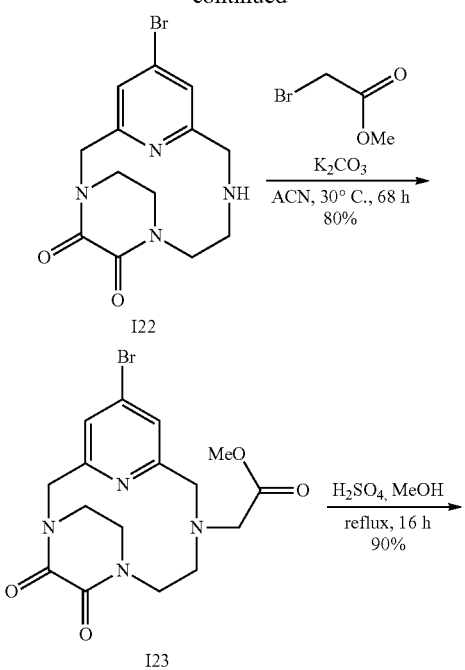

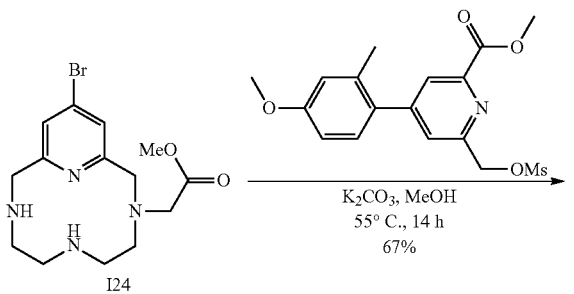

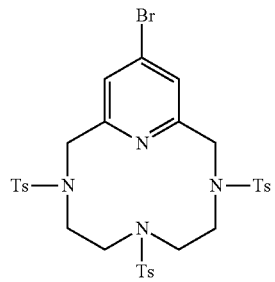 [SMILES: Cc1ccc(S(=O)(=O)N2CCN(S(=O)(=O)c3ccc(C)cc3)Cc3cc(Br)cc(n3)CN(S(=O)(=O)c3ccc(C)cc3)CC2)cc1]

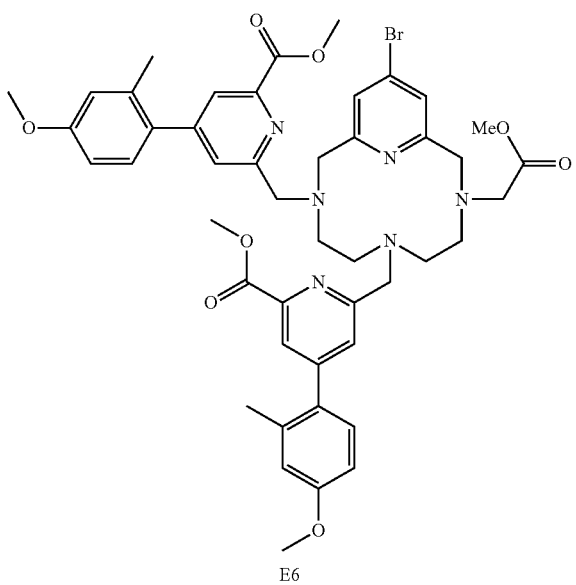

methyl 4-(4-methoxy-2-methylphenyl)-6-(((methylsulfonyl)oxy)methyl)picolinate (I19)

A solution of methyl 6-(hydroxymethyl)-4-(4-methoxy-2-methylphenyl)picolinate (442 mg, 1.54 mmol) and Et$_3$N (614 µL, 4.61 mmol, 3 eq) in CH$_2$Cl$_2$ (17 mL) was cooled down to 0° C. before dropwise addition of methane sulfonylchloride (179 µL, 2.3 mmol, 1.5 eq). The reaction mixture was then stirred at room temperature for 2 h before addition of saturated NaHCO$_3$ (200 mL). Phases were separated and the aqueous phase was extracted with CH$_2$Cl$_2$ (3*100 mL). The organic layers combined, washed with saturated NaHCO$_3$ (2*100 mL) and water (4*100 mL), dried over MgSO$_4$ and solvents were evaporated to dryness to give compound I19 (535 mg, 1.46 mmol, 95%) as an oil with a green reflection. $^1$H NMR (300 MHz, CDCl$_3$) δ 8.09 (d, J=1.3 Hz, 1H), 7.63 (s, 1H), 7.21-7.15 (m, 1H), 6.84 (m, 2H), 5.48 (s, 2H), 4.02 (s, 3H), 3.85 (s, 3H), 3.16 (s, 3H), 2.30 (s, 3H).

1$^4$-bromo-3,6,9-tritosyl-3,6,9-triaza-1(2,6)-pyridina-cyclodecaphane (I20)

A solution of 4-methyl-N,N-bis(2-((4-methylphenyl)sulfonamido)ethyl)benzenesulfonamide (6.268 g, 11.1 mmol), Cs$_2$CO$_3$ (7.582 g, 23.3 mmol, 2.1 eq.) in acetonitrile (264 mL) was stirred at 80° C. To this solution was added dropwise over 5.5 hours a solution of 4-bromo-2,6-bis(bromomethyl)pyridine (3.810 g, 11.1 mmol, 1 eq.) in acetonitrile (88 mL) at 70° C. The reaction mixture was stirred at 80° C. for 17 h before filtration of the insoluble solids (hereafter "solid 1"). The filtrate was evaporated to dryness, the residue was suspended in EtOH and the solution for stirred under reflux for 1 h. The yellow solid was filtered and washed with EtOH to give compound I20 (2.016 g, 2.69 mmol, 24%) as a yellow solid. The solid 1 was dissolved in CH$_2$Cl$_2$ (150 mL) and H$_2$O (150 mL). The layers were separated and the aqueous phase was extracted with CH$_2$Cl$_2$ (4*50 mL). The combined organic phases were dried over MgSO$_4$ and solvents were evaporated to dryness to give compound I20 (5.593 g, 7.48 mmol, 67%) as a yellow solid. $^1$H NMR (300 MHz, CDCl$_3$) δ 7.42 (t, J=7.3 Hz, 6H), 7.05 (m, 8H), 3.99 (s, 4H), 3.05 (t, J=7.3 Hz, 4H), 2.64 (br s, 4H), 2.18 (s, 6H), 2.15 (s, 3H). $^{13}$C NMR (75 MHz, CDCl$_3$) δ 156.5, 143.9, 143.6, 135.9, 135.2, 135.1, 129.9, 129.8, 127.2, 54.5, 49.9, 47.7, 21.5.

1⁴-bromo-3,6,9-triaza-1(2,6)-pyridinacyclodecaphane (I21)

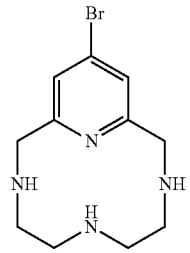 [SMILES: Brc1cc2nc(c1)CNCCNCCNC2]

To a solution of compound I20 (6.086 g, 8.1 mmol) in HBr (33% solution in acetic acid, 313 mL) was added phenol (27 mL). The reaction mixture was slowly warmed from 70° C. to 90° C. and the resulting gases were neutralized in a saturated solution of sodium hydroxide. The reaction mixture was then stirred at 90° C. for 2.5 days and was then allowed to cooled down to room temperature. The resulting solid was filtrated, washed with $CH_2Cl_2/Et_2O$ 1/1 and dried under vacuum to give a brownish solid. This solid was dissolved in NaOH 1M (30 mL) and the reaction mixture was stirred at room temperature for 1.5 h. Solvents were evaporated to dryness and the residue was then suspended in acetonitrile (100 mL). The mixture was then stirred at room temperature for 3 h, and the residual salts were filtered on cotton. The filtrate was evaporated to dryness to give compound I21 (2.157 g, 7.6 mmol, 92%). $^1$H NMR (300 MHz, $D_2O$) δ 7.42 (s, 2H), 3.87 (s, 4H), 2.80-2.66 (m, 4H), 1.92 (br s, 4H). $^1$H NMR (300 MHz, $D_2O$) δ 163.6, 136.4, 126.7, 54.9, 50.2, 49.9.

3⁴-bromo-5-aza-1(1,4)-piperazina-3(2,6)-pyridinacycloheptaphane-1²,1³-dione (I22)

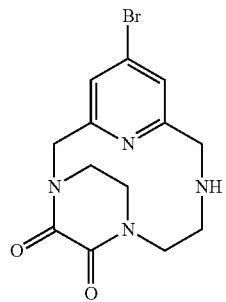 [SMILES: O=C1C(=O)N2CCN1CCNCc1cc(Br)cc(n1)C2]

To a solution of compound I21 (1.028 g, 3.6 mmol) in MeOH (25 mL) was added dropwise a solution of diethyl oxalate (490 μL, 3.6 mmol, 1 eq) in MeOH (12.5 mL). The reaction mixture was stirred at room temperature for 2.5 days, before addition of a solution of 0.3 eq of diethyl oxalate. The reaction mixture was stirred at 50° C. for 24 h before evaporation of solvents to dryness. The residue was then purified by precipitation in $MeOH/CH_2Cl_2$, followed by a second precipitation in $MeOH/Et_2O$ to give compound I22 (1.122 g, 3.3 mmol, 91%) as a white foam. $^1$H NMR (300 MHz, $CDCl_3$) δ 7.24 (s, 1H), 7.16 (s, 1H), 5.63 (d, J=16.7 Hz, 1H), 4.72-4.58 (m, 1H), 4.08 (d, J=16.7 Hz, 1H), 4.00 (d, J=17.7 Hz, 1H), 3.92-3.62 (m, 3H), 3.33-3.16 (m, 2H), 3.14-3.04 (m, 1H), 2.91-2.76 (m, 2H). $^{13}$C NMR (75 MHz, $CDCl_3$) δ 163.1, 161.3, 160.9, 155.5, 133.5, 123.9, 123.0, 55.4, 52.6, 48.4, 48.2, 45.2, 44.9. ESI-HR-MS (positive, $H_2O$) m/z calcd. for $[C_{13}H_{16}BrN_4O_2]^+$: 339.0451, found: 339.0451.

methyl 2-(3⁴-bromo-1²,1³-dioxo-5-aza-1(1,4)-piperazina-3(2,6)-pyridinacycloheptaphane-5-yl)acetate (I23)

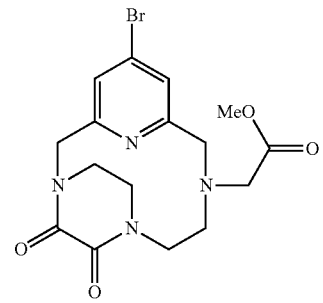 [SMILES: COC(=O)CN1CCN2CCN(Cc3cc(Br)cc(n3)C1)C(=O)C2=O]

A solution of compound I22 (500 mg, 1.47 mmol) and $K_2CO_3$ (611 mg, 4.42 mmol, 3 eq) in acetonitrile (64 mL) was stirred at room temperature for 30 min. To this reaction mixture was added dropwise a solution of methyl bromoacetate (153 μL, 1.62 mmol, 1.1 eq) in acetonitrile (12.5 mL). The reaction mixture was stirred at 30° C. for 62 h before filtration of the salts. Solvents were evaporated to dryness and the residue was taken up in chloroform. Residuals salts were filtered on cotton and the chloroform was evaporated to dryness. Purification of the residue by precipitation in $MeOH/Et_2O$ gave compound I23 (488 mg, 1.19 mmol, 80%) as a white foam. $^1$H NMR (300 MHz, $CDCl_3$) δ 7.24 (s, 1H), 7.08 (s, 1H), 5.59 (d, J=16.8 Hz, 1H), 4.42 (m, 1H), 4.20-4.00 (m, 3H), 3.96 (s, 2H), 3.70 (s, 3H), 3.50 (d, J=18.1 Hz, 1H), 3.32 (d, J=18.2 Hz, 2H), 3.27-3.14 (m, 1H), 3.03 (m, 2H), 2.73 (ddd, J=14.1, 6.5, 3.4 Hz, 1H). $^{13}$C NMR (75 MHz, $CDCl_3$) δ 172.2, 162.7, 160.5, 160.1, 155.9 133.3, 123.5, 122.9, 61.3, 56.7, 52.7, 52.2, 51.4, 46.8, 46.4, 45.5. ESI-HR-MS (positive, $H_2O$) m/z calcd. for $[C_{16}H_{20}BrN_4O_4]^+$: 411.0662, found: 411.0658, calcd. for $[C_{16}H_{19}BrN_4NaO_4]^+$: 433.0482, found: 433.0476.

methyl 2-(1⁴-bromo-3,6,9-triaza-1(2,6)-pyridinacyclodecaphane-3-yl)acetate (I24)

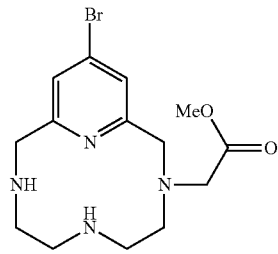 [SMILES: COC(=O)CN1CCNCCNCc2cc(Br)cc(n2)C1]

To a solution of compound I23 (488 mg, 1.19 mmol) in MeOH (35 mL) was added dropwise concentrated $H_2SO_4$ (3.5 mL). The reaction was stirred under reflux for 16 h, and the temperature was then cooled down to room temperature before addition of a saturated solution of $K_2CO_3$ until pH=7. Solvents were evaporated to dryness and the residue was taken up in DCM/MeOH 98/2. The salts were filtered on cotton on the filtrate was evaporated to dryness. The residue was dissolved in $H_2O$ (20 mL) and the impurities were extracted with $CH_2Cl_2$ (2*10 mL). The aqueous phase was evaporated to dryness to give compound I24 (384 mg, 1.07 mmol, 90%) as a yellow oil. $^1$H NMR (400 MHz, $CDCl_3$) δ 7.15 (s, 1H), 7.14 (s, 1H), 3.97 (s, 2H), 3.91 (s, 2H), 3.66 (s, 3H), 3.63 (s, 2H), 2.99 (t, J=4.9 Hz, 4H), 2.35 (m, 2H), 2.27 (m, 2H). $^{13}$C NMR (75 MHz, $CDCl_3$) δ 171.9, 162.4, 160.4, 133.5, 123.3, 123.1, 58.2, 57.4, 52.6, 52.2, 51.3, 47.5, 47.3, 46.7. ESI-HR-MS (positive, $H_2O$) m/z calcd. for $[C_{14}H_{22}BrN_4O_2]^+$: 357.0921, found: 357.0921, calcd. for $[C_{14}H_{21}BrN_4NaO_2]^+$: 379.0740, found: 379.0739. calcd. for $[C_{14}H_{23}BrN_4O_2]^{2+}$: 179.0497, found: 179.0494.

Synthesis of dimethyl 6,6'-((1⁴-bromo-9-(2-methoxy-2-oxoethyl)-3,6,9-triaza-1(2,6)-pyridinacyclododecaphane-3,6-diyl)bis(methylene))bis(4-(4-methoxy-2-methylphenyl)picolinate) (E6)

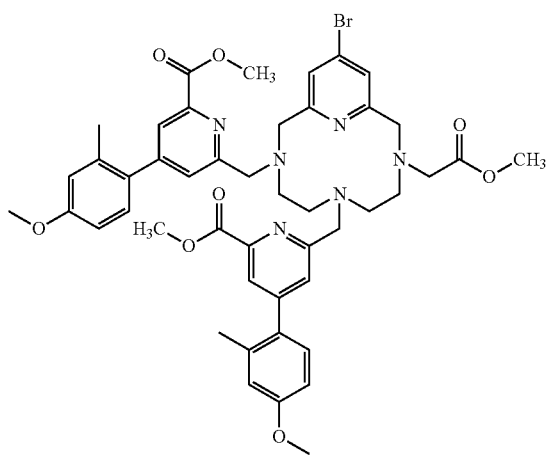

A solution of compound I24 (239 mg, 0.67 mmol) and $K_2CO_3$ (370 mg, 2.66 mol, 4 eq) in acetonitrile (16.7 mL) was stirred at room temperature for 30 min. To this solution was added dropwise a solution of mesylated antenna I19 (506 mg, 1.38 mmol, 2.07 eq) in acetonitrile (25 mL) and the reaction mixture was stirred at 55° C. for 14 h to give a milky solution. Salts were filtered and the filtrate was evaporated to dryness. The residue was taken up in $CH_2Cl_2$ and residual salts were filtered on cotton. The filtrate was evaporated to dryness. Purification of the residue by chromatography on activated alumina gel (eluent: DCM/MeOH 100/0 to 100/2) gave compound E6 (406 mg, 0.45 mmol, 67%) as a yellow oil. $^1$H NMR (500 MHz, $CDCl_3$), due to its complexity, some signals could not be described δ 7.86 (s, 1H), 7.81 (s, 1H), 7.40 (s, 1H), 7.35 (s, 1H), 7.28 (s, 1H), 7.20 (s, 1H), 7.10 (m, 2H), 6.82-6.74 (m, 4H), 4.29 (d, J=15.0 Hz, 1H), 4.13 (d, J=15H, 1H), 4.07 (d, J=15 Hz, 1H), 3.96 (s, 3H), 3.80 (s, 3H), 3.79 (s, 3H), 3.72 (s, 3H), 3.67 (s, 3H), 4.00-3.63 (5H hidden in the others signals), 3.55 (d, J=15.8 Hz, 1H), 3.43 (d, J=17.5 Hz, 1H), 3.08 (m, 1H), 2.77 (d, J=14.7 Hz, 1H), 2.70 (br s, 2H), 2.54-2.47 (m, 1H), 2.36 (d, J=13.2 Hz, 1H), 2.24 (s, 3H), 2.23 (s, 3H), 2.23-2.22 (m, 1H), 1.96-1.87 (m, 1H). $^{13}$C NMR (125 MHz, $CDCl_3$) δ 171.5, 165.8, 165.0, 160.6, 159.9, 159.5, 158.2, 152.3, 152.2, 147.1*2, 136.4*2, 134.2, 130.6, 129.9, 129.7, 127.2, 126.8, 124.3, 124.1, 123.7, 116.3, 111.8*2, 62.9, 61.2, 60.7, 59.7, 56.8, 56.0, 55.2, 55.0, 52.9, 52.5, 51.6, 51.3, 20.5. ESI-HR-MS (positive, H2O) m/z calcd. for $[C_{46}H_{52}BrN_6O_8]^+$: 895.3025, found: 895.3029, calcd. for $[C_{46}H_{51}BrN_6NaO_8]^+$: 917.2844, found: 917.2847. calcd. for $[C_{46}H_{53}BrN_6O_8]^{2+}$: 448.1549, found: 448.1551.

Example 2: Synthesis of Chelates According to the Invention

General Materials and Methods

General materials and methods are as described in Example 1.

Example 2-1: Synthesis of Eu Chelate [Eu(S1)]

Ligand S1 (25 mg, 21.3 µmol) was dissolved in $H_2O$ (10 mL). The pH was adjusted to 6.42 with HCl 0.2M before addition of $EuCl_3·6H_2O$ (15 mg, 1.5 eq). The pH was then adjusted to 5.82 with KOH 1M. The reaction mixture was stirred at room temperature for 1 h and the pH checked again. The reaction mixture was stirred at reflux for 20 h and solvents were evaporated to dryness. Purification of the residue by flash chromatography (cartridge C18 from Reveleris, Gradient: $H_2O$/MeOH 100/0 to 2/8 over 35 min) gave the Eu complex [Eu(S1)] (8 mg, 6.6 µmol, 31%) as a yellow solid. ESI-HR-MS (positive, MeOH) m/z calcd. for $[C_{57}H_{64}EuN_6O_{14}]^+$: 1209.3687, found: 1209.3708, $[M+H]^+$; calcd. for $[C_{57}H_{65}EuN_6O_{14}]^{2+}$: 605.1880, found: 605.1891, $[M+2H]^{2+}$.

Example 2-2: Synthesis of Sm Chelate [Sm(S1)]

Ligand S1 (22 mg, 18.7 µmol) was dissolved in $H_2O$ (10 mL). The pH was controlled (8.29) before addition of $SmCl_3·6H_2O$ (10 mg, 1.5 eq). The pH was then adjusted to 5.55 with KOH 1M. The reaction mixture was stirred at reflux for 1 h and the pH checked again. The reaction mixture was stirred at reflux for 17 h, resulting in the formation of a solid on the flask's walls. The reaction mixture was filtered on cotton and rinsed with $H_2O$. The solid stuck on the cotton was dissolved with MeOH and combined with the solid on the flask's walls to give the Sm(III) complex [Sm(S1)] (13 mg, 10.8 µmol, 58%) as a brown oil. ESI-HR-MS (positive, MeOH) m/z calcd. for $[C_{57}H_{64}N_6O_{14}Sm]^+$: 1208.3672, found: 1208.3688, $[M+H]^+$; calcd. for $[C_{57}H_{65}N_6O_{14}Sm]^{2+}$: 604.6872, found: 604.6876, $[M+2H]^{2+}$.

Example 2-3: Synthesis of Yb Chelate [Yb(S2)]

Compound S2 (69 mg, 47 µmol) was dissolved in $H_2O$ (10 mL). The pH was adjusted to 6.45 with HCl 0.2M before addition of $YbCl_3·xH_2O$ (55 mg, 141 µmol, 3 eq). The pH was then adjusted to 6.19 with KOH 1M. The reaction mixture was stirred at room temperature for 4 h and the pH checked again. The reaction mixture was stirred at room temperature for 70 h, resulting in the formation of a precipitate. The reaction mixture was filtered on cotton and rinsed with $H_2O$ to remove the salts in excess and the precipitate on the cotton was then dissolved thanks to MeOH. Evaporation of the MeOH gave the Yb(III) complex [Yb(S2)] (31 mg, 20 µmol, 43%) as a yellow oil. ESI-HR-MS (positive, MeOH) m/z calcd. for $[C_{71}H_{95}N_8O_{18}Yb]^{21}$:

760.8071, found: 760.8077, [M+3H]$^{2+}$; calcd. for [C$_{71}$H$_{96}$N$_8$O$_{18}$Yb]$^{3+}$: 507.5405, found: 507.5419, [M+4H]$^{3+}$.

Example 2-4: Synthesis of Dy Chelate [Dy(S3)]

Compound S3 (30 mg, 26 μmol) was dissolved in H$_2$O (10 mL). The pH was adjusted to 6.36 with HCl 0.2M before addition of DyCl$_3$·6H$_2$O (15 mg, 39 μmol, 1.5 eq). The pH was then adjusted to 7.51 with KOH 1M. The reaction mixture was stirred at room temperature for 1 h and the pH checked again. The reaction mixture was stirred at 30° C. for 2.5 days before evaporation of solvents to dryness. The residue was submitted to a dialysis for 19 h (cut-off 100-500 Da) to give the Dy(III) complex [Dy(S3)] (31 mg, 26 μmol, 100%). ESI-HR-MS (positive, MeOH) m/z calcd. for [C$_{55}$H$_{68}$DyN$_6$O$_{14}$]$^+$: 1200.4078, found: 1200.4097, [M+H]$^+$; calcd. for [C$_{55}$H$_{69}$DyN$_6$O$_{14}$]$^{2+}$: 600.7076, found: 600.7093, [M+2H]$^{2+}$; calcd. for [C$_{55}$H$_{68}$DyN$_6$NaO$_{14}$]$^{2+}$: 611.6986, found: 611.6991, [M+H+Na]$^{2+}$; calcd. for [C$_{55}$H$_{67}$CaDyN$_6$CaO$_{14}$]$^{2+}$: 619.6811, found: 619.6826, [M+Ca]$^{2+}$.

Example 2-5: Synthesis of Tb Chelate [Tb(S3)]

Compound S3 (40 mg, 35 μmol) was dissolved in H$_2$O (10 mL). The pH was adjusted to 6.74 with HCl 0.2M before addition of TbCl$_3$·6H$_2$O (19 mg, 52 μmol, 1.5 eq). The pH was then adjusted to 6.63 with KOH 1M. The reaction mixture was stirred at room temperature for 1 h and the pH checked again. The reaction mixture was stirred at 30° C. for 2.5 days before evaporation of solvents to dryness. The residue was submitted to a dialysis for 19 h (cut-off 100-500 Da) to give the Tb(III) complex [Tb(S3)] (41 mg, 35 μmol, 100%). ESI-HR-MS (positive, MeOH) m/z calcd. for [C$_{55}$H$_{68}$N$_6$O$_{14}$Tb]$^+$: 1195.4041, found: 1195.4047, [M+H]$^+$; calcd. for [C$_{55}$H$_{67}$N$_6$NaO$_{14}$Tb]$^+$: 1217.3861, found: 1217.3861, [M+Na]$^+$; calcd. for [C$_{55}$H$_{69}$N$_6$O$_{14}$Tb]$^{2+}$: 598.2057, found: 598.2070, [M+2H]$^{2+}$; calcd. for [C$_{55}$H$_{68}$N$_6$NaO$_{14}$Tb]$^{2+}$: 609.1967, found: 609.1960, [M+H+Na]$^{2+}$; calcd. for [C$_{55}$H$_{67}$N$_6$CaO$_4$Tb]$^{2+}$: 617.1792, found: 617.1804, [M+Ca]$^{2+}$; calcd. for [C$_{55}$H$_{67}$FeN$_6$O$_{14}$Tb]$^{2+}$: 625.1654, found: 625.1671, [M+Fe]$^{2+}$.

Example 2-6: Synthesis of Eu Chelate [Eu(S4)]

Compound S4 (29 mg, 25 μmol) was dissolved in H$_2$O (10 mL). The pH was adjusted to 7.15 with HCl 0.2M before addition of EuCl$_3$·6H$_2$O (14 mg, 37 μmol, 1.5 eq) and the pH was controlled at 4.56. The reaction mixture was stirred at reflux for 1 h and the pH checked again. The reaction mixture was stirred at reflux for 2.5 days, resulting in the formation of an oil on the flask's walls. The reaction mixture was filtered on cotton and rinsed with H$_2$O to remove the salts in excess and the precipitate on the cotton was then dissolved thanks to MeOH. Evaporation of the MeOH gave the Eu(III) complex [Eu(S4)](18 mg, 15 μmol, 60%) as a yellow oil. ESI-HR-MS (positive, MeOH) m/z calcd. for [C$_{57}$H$_{64}$EuN$_6$O$_{14}$]$^+$: 1209.3687, found: 1209.3697, [M+H]$^+$; calcd. for [C$_{57}$H$_{65}$EuN$_6$O$_{14}$]$^{2+}$: 605.1880, found: 605.1895, [M+2H]$^{2+}$.

Example 2-7: Synthesis of Eu Chelate [Eu(S7')]

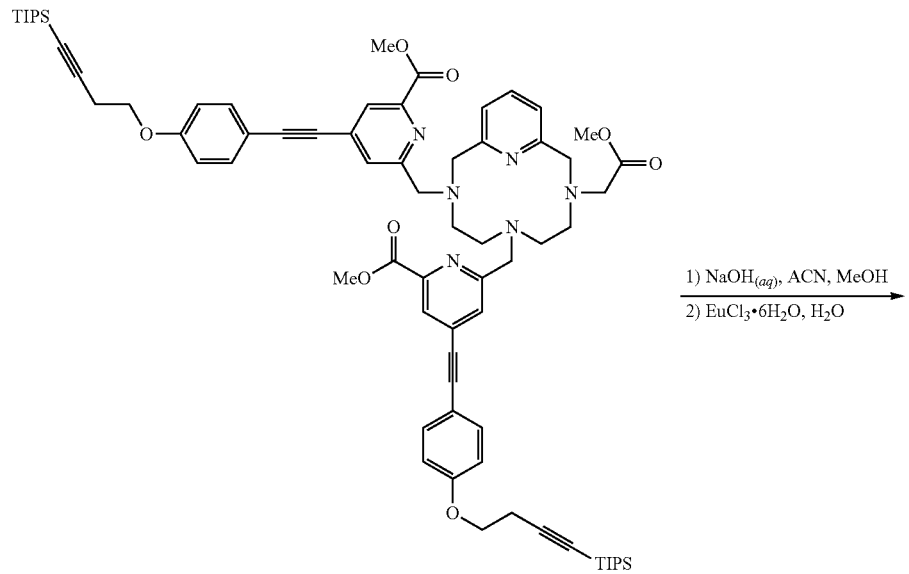

Scheme 7: Synthesis of [Eu(S7')] chelate

-continued

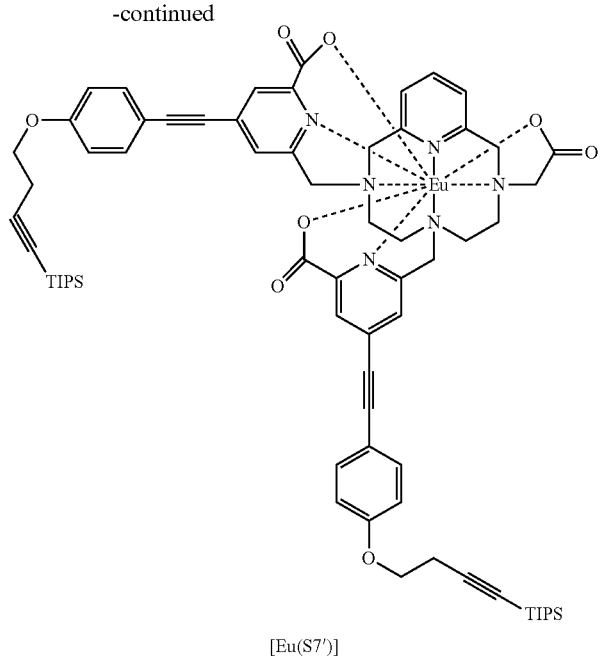

[Eu(S7')]

To a solution of compound I17 (50 mg, 0.04 mmol) in THF/MeOH (8/2 v/v, 3 mL) was added 1M NaOH (0.53 mL). The reaction mixture was stirred at reflux for 22 h. Solvents were evaporated and then the compound was dissolved in H$_2$O (5 m). The pH was adjusted to 6.4 with HCl 0.2M before the addition of EuCl$_3$·6H$_2$O (5 mg, 1.5 eq). The pH was readjusted to 5.8 with NaOH 1M. The reaction mixture was stirred at room temperature for 1 h and the pH was checked again. The reaction mixture was stirred at reflux for 20 h and the europium complex was collected by centrifugation (30 mg, 56%).

Example 2-8: Synthesis of Eu Chelates [Eu(S8')] and [Eu(S5')]

Scheme 8: Synthesis of [Eu(S8')] and [Eu(S5')] Chelates

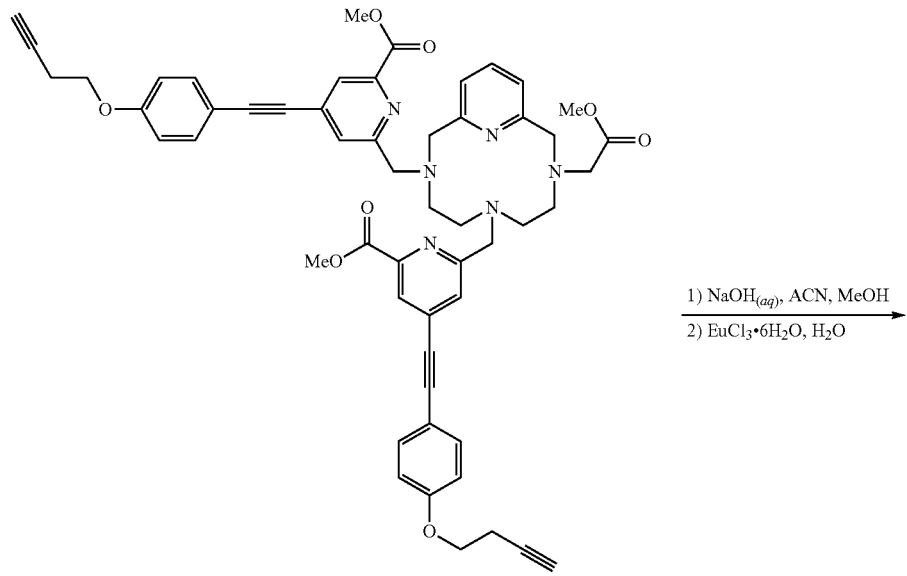

I18

1) NaOH$_{(aq)}$, ACN, MeOH
2) EuCl$_3$·6H$_2$O, H$_2$O

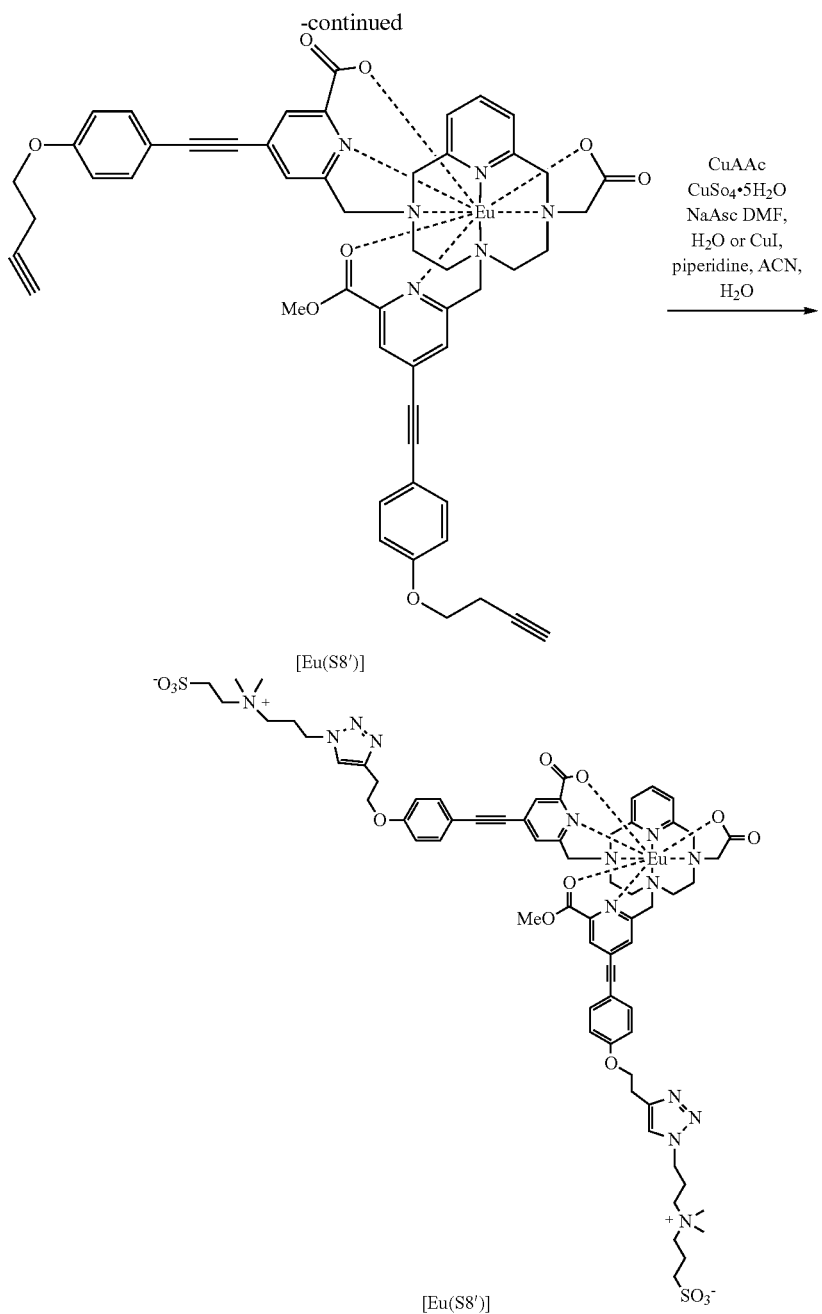

[Eu(S8')] was obtained following the same complexation procedure used for [Eu(S7')]. (yield=44%).

[Eu(S8')] can be used to introduce the water-solubilizing anchor 110 using copper(I)-catalysed azide alkyne cycloaddition (CuAAC). In a typical procedure, the alkynyl lanthanide complex [Eu(S8')] (0.2 mmol), the clickable water-solubilizing azide 110 (2.2 eq.), and CuI (5%) were placed in a microwave vial along with a magnetic stirring bar. The reactants were suspended in a 4:1:1 mixture of $CH_3CN$, piperidine, water (0.2 M). The vial was sealed, and the mixture was heated at 100° C. for 45 mins. The mixture was cooled down to room temperature and the volatiles were evaporated. The crude was redissolved in DCM and the solid part was collected.

Example 3: Spectroscopic Data of Chelates

Methods

Absorption spectra were recorded on a JASCO V-650 spectrophotometer as solutions in spectrophotometric-grade methanol or water (ca. $10^{-5}$ or $10^{-6}$ mol·L$^{-1}$). Emission spectra were measured by using a Horiba-Jobin-Yvon Fluorolog-3 fluorimeter. Spectra were corrected for both excitation-source light-intensity variation and emission spectral responses. Luminescence lifetimes were obtained by pulsed excitation with a FL-1040 UP xenon lamp. Luminescence quantum yields, D, were measured with dilute solutions in water or organic solvents with an absorbance of less than 0.1.

$$\frac{\Phi_x}{\Phi_r} = \frac{A_r(\lambda)}{A_x(\lambda)} \frac{n_x^2}{n_r^2} \frac{D_x}{D_r}$$

The reference is quinine bisulfate in an aqueous solution of sulfuric acid 1N ($\Phi_r$=0.546). Excitation of reference and sample compounds was performed at the same wavelength.

Example 3-1: Spectroscopic Data of Chelates According to the Invention

Spectroscopic data of complexes of Example 2 above are provided in Table 5 below.

TABLE λ5

| Complex | $\lambda_{abs}$ (nm) | Φ | $\varepsilon^{max}$ (L.mol$^{-1}$. cm$^{-1}$) | B$^{(*)}$ (L.mol$^{-1}$. cm$^{-1}$) | τ (ms) |
|---|---|---|---|---|---|
| [Eu(S1)] | 336 (H$_2$O) | 30% (H$_2$O) | 41000 (MeOH) | 12300 | 1.05 (H$_2$O) |
| [Sm(S1)] | 335 (H$_2$O) | 1% (H$_2$O) | 47000 (MeOH) | 470 | <0.01 (H$_2$O) |

TABLE λ5-continued

| Complex | $\lambda_{abs}$ (nm) | Φ | $\varepsilon^{max}$ (L.mol$^{-1}$. cm$^{-1}$) | B$^{(*)}$ (L.mol$^{-1}$. cm$^{-1}$) | τ (ms) |
|---|---|---|---|---|---|
| [Dy(S3)] | 302 (H$_2$O) | 2% (H$_2$O) | 15000 (MeOH) | 300 | — |
| [Tb(S3)] | 300 (H$_2$O) | 72% (H$_2$O) | 18000 (MeOH) | 10800 | 1.59 (H$_2$O) |
| [Eu(S4)] | 333 (H$_2$O) | 10% (H$_2$O) | 44000 (MeOH) | 4400 | 0.77 (H$_2$O) |

(*)B = Φ * εmax and is estimated with Φ in H$_2$O and ε in MeOH

The spectroscopic properties of chelates according to the invention as shown in Table 5 are on the range of the best lanthanide chelates for use in fluorescence which are known in prior art.

Example 3-2: Comparative Spectroscopic Data of Chelates

Prior art compounds for which comparative data are presented hereafter are shown in Table 6 below.

TABLE 6

| Reference | Complex | Formula |
|---|---|---|
| *Inorg. Chem.* 2011, 50, 4987-4999. | [Eu(C5)] | 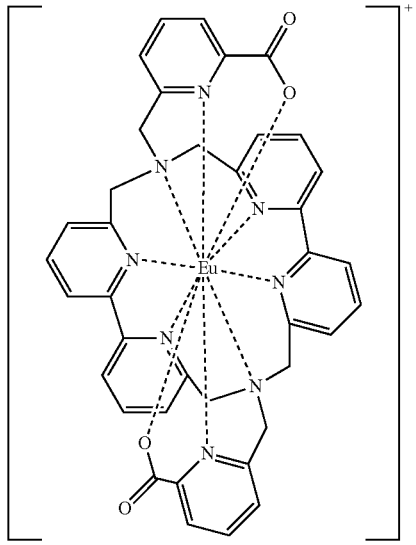 |

TABLE 6-continued
| Reference | Complex | Formula |
|---|---|---|
| | [Eu(C6)] | 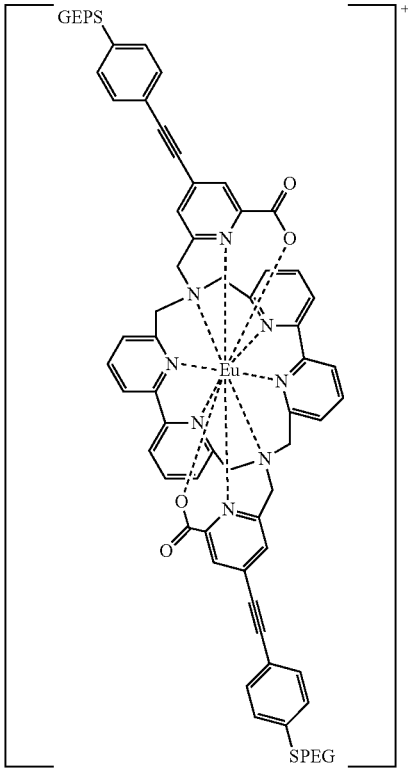<br>wherein —SPEG represents —S(CH$_2$CH$_2$O)$_3$CH$_3$. |
| Eur. J. Inorg. Chem. 2017, 2122-2129. | [Eu(C7)] | 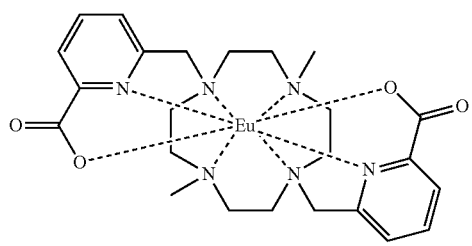 |

TABLE 6-continued
| Reference | Complex | Formula |
|---|---|---|
| *Inorg. Chem.* 2016, 55, 7020-7025 | [Eu(C8)] | 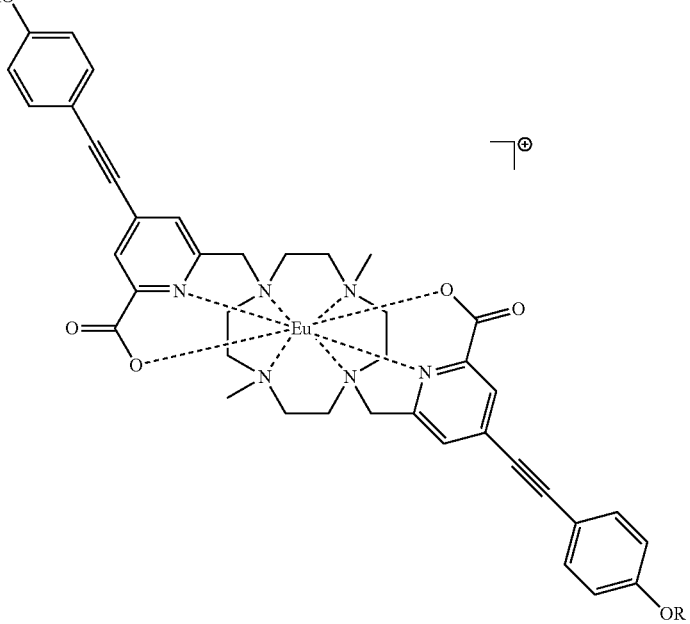 wherein —OR represents —O(CH$_2$CH$_2$O)$_3$CH$_3$. |
| *Helv. Chim. Acta* 2009, 92, 2257-2273. | [Tb(C9)] | 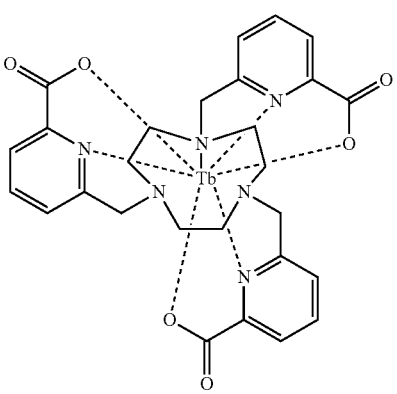 |

TABLE 6-continued

| Reference | Complex | Formula |
|---|---|---|
| *Dalton Trans.*, 2015, 44, 4918-4924<br>*J. Am. Chem. Soc.* 2017, 139, 7693-7696 | [Tb(C10)] | |
| *J. Am. Chem. Soc.* 2017, 139, 7693-7696 | [Tb(C11)] | wherein —OR represents —O(CH$_2$CH$_2$O)$_3$CH$_3$. |
| *Inorganic Chemistry* 2018 57 (12), 6932-6945 | [Eu(C3)] | |

TABLE 6-continued

| Reference | Complex | Formula |
|---|---|---|
| *Inorganic Chemistry* 2018 57 (12), 6932-6945 | [Eu(C4)] | (structure of Eu complex) |
| *Inorganic Chemistry* 2018 57 (12), 6932-6945 | [Tb(C4)] | (structure of Tb complex) |

Spectroscopic data issued from prior art documents, from Applicant's comparative data and from Example 3-1 above are provided in Table 7 below.

In the experiments reported in Table 7, addition of an arylalkyne- (C6, C8) or alkoxyaryl-based (C10, C11)chromophore on the picolinate arm of an azamacrocyclic ligand

TABLE 7

| Reference | Complex | $\lambda_{abs}$ (nm) | $\Phi$ | $\epsilon^{max}$ (L.mol$^{-1}$.cm$^{-1}$) | B (L.mol$^{-1}$.cm$^{-1}$) | $\tau$ (ms) |
|---|---|---|---|---|---|---|
| Inorg. Chem. 2011 | [Eu(C5)] | 308 | 13% (H$_2$O) | 18000 | 2340 | 1.80 ($\tau_{Eu}$) |
|  | [Eu(C6)] | 330 (H$_2$O) | 1% (H$_2$O) | 53000 | 530 | 0.53 ($\tau_{Eu}$) |
| Eur. J. Inorg. Chem. 2017 | [Eu(C7)] | 330 (H$_2$O) | 10% (H$_2$O) | 9300 | 930 | 0.96 |
| Inorg. Chem. 2016 | [Eu(C8)] | — | 1% (H$_2$O) | 40500 | 405 | 0.47 |
| Helv. Chim. Acta 2009 | [Th(C9)] | — | 60% (H$_2$O) | 15800 | 9480 | 2.00 (H$_2$O) |
| Dalton Trans., 2015 | [Th(C10)] | 308 | 15% (MeOH) | 33000 | 4950 | 0.23 (MeOH) |
| J. Am. Chem. Soc. 2017 | [Th(C11)] | — | 13% (MeOH) | — | — | 0.22 (MeOH) |
| Comparative data | [Eu(C4)] | — | 22% (H$_2$O) | 15000 | 3300 | 1.52 (H$_2$O) |
| Example 3-1 | [Eu(S1)] | 336 (H$_2$O) | 30% (H$_2$O) | 41000 (MeOH) | 12300 | 1.05 (H$_2$O) |
| Comparative data | [Eu(C3)] | — | 16% (H$_2$O) | 15000 | 2400 | 0.98 (H$_2$O) |
| Example 3-1 | [Eu(S4)] | 333 (H$_2$O) | 10% (H$_2$O) | 44000 (MeOH) | 4400 | 0.77 (H$_2$O) |
| Comparative data | [Tb(C4)] | — | 90% (H$_2$O) | 15000 | 13500 | 2.48 (H$_2$O) |
| Example 3-1 | [Tb(S3)] | 300 (H$_2$O) | 72% (H$_2$O) | 10800 (MeOH) | 18000 | 1.59 (H$_2$O) | was carried out in order to render the ligand compatible for two-photon (Near-IR) and/or in order to improve its spectroscopic properties.

However, the experimental data shown in Table 7 unambiguously shows that this modification of the ligand can incur a decrease of the emission quantum yield and/or molar absorption, leading to a decrease of the brightness, and/or an increase of the lifetime of the chelate. Thus, the lanthanide chelate does not yield good spectroscopic performance and/or is not suitable for in vitro assays. For example, both brightness and lifetime are divided by about 4 for [Eu(C6)] chelate compared to [Eu(C5)] chelate.

By contrast, significant increase in brightness of europium (Eu) chelates is observed when the picolinate arms of the ligands according to the invention are substituted by arylalkyne- or alkoxyaryl-based chromophore (S1: about 4-fold increase and S4: about 3-fold increase). Brightness of the terbium (Tb) chelate [Tb(C4)] was already very high for this lanthanide, especially due to a high emission quantum yield (90%), so that [Tb(S3)] and [Tb(C4)] chelates have comparable brightness. However, as [Tb(S3)] chelate emits in 700-900 nm wavelength range, it is advantageous over [Tb(C4)] for use in two-photon absorption in vivo assays.

The invention claimed is:

1. A compound of Formula (A):

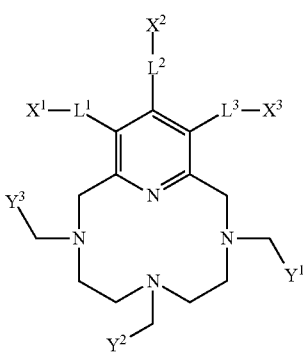

or a salt thereof;
wherein
$Y^1$, $Y^2$ and $Y^3$ each independently represents —COOH or a picolinate of Formula (i):

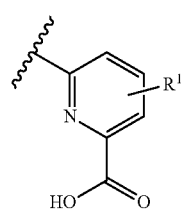

wherein each $R^1$ independently represents
a chromophore group of Formula (ii):

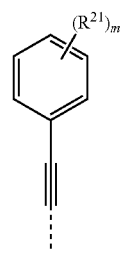

wherein
m is an integer ranging from 0 to 2;
each $R^{21a}$ independently represents —O-polyether, —S-polyether, —N(polyether)R, or —O-$L^{41}$-polyether;
wherein
R represents hydrogen, alkyl, or polyether;
$L^{41}$ represents alkyl, said alkyl optionally additionally comprising a coupling product through which $R^{21a}$ is bound to $L^{41}$; and
each $R^{21b}$ represents independently alkyl;
or a chromophore group of Formula (iii):

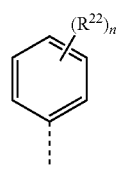

wherein
n is an integer ranging from 0 to 2;
each $R^{22a}$ independently represents —O-polyether, —S-polyether, —N(polyether)R, or —O-$L^{42}$-polyether;
wherein
R represents hydrogen, alkyl, or polyether;
$L^{42}$ represents alkyl, said alkyl optionally additionally comprising a coupling product through which $R^{22a}$ is bound to $L^{42}$; and
each $R^{22b}$ represents independently alkyl;
provided that at least two among $Y^1$, $Y^2$ and $Y^3$ represents a picolinate of Formula (i);
$L^1$, $L^2$ and $L^3$ each independently represents
a single bond; or
a linker selected from alkyl, aryl, arylalkyl, alkylaryl, heteroalkyl, heteroaryl, heteroarylalkyl, alkylheteroaryl, alkenyl, and alkynyl; said linker optionally additionally comprising a coupling product through which $X^1$, $X^2$ and $X^3$ are bounded to $L^1$, $L^2$ and $L^3$ respectively;
$X^1$, $X^2$ and $X^3$ each independently represents:
a hydrogen atom;
a coupling function selected from amine; isothiocyanate; isocyanate; activated ester; carboxylic acid; activated carboxylic acid; alcohol; alkene; alkyne; halide; azide; siloxy; phosphonic acid; thiol; tetrazine; norbornen; oxoamine; aminooxy; thioether; haloacetamide; glutamate; glutaric anhydride, succinic anhydride, maleic anhydride; aldehyde; ketone; hydrazide; chloroformate; and maleimide; or a bio-vectorizing group selected from antibody; hapten; peptide; protein; polysaccharide; fatty acid; liposome; lipid; polyamine; nanoparticle; polymeric microparticle; macrocyclic chelate; cationic group suitable for cellular internalization; and combinations thereof.

2. The compound according to claim 1, wherein the salt of said compound of formula (A) is a carboxylate salt thereof.

3. The compound according to claim 1, wherein m is 0 or 1 and/or n is 0 or 1.

4. The compound according to claim 1, wherein the chromophore group of Formula (iii) comprises at least one $R^{22b}$ group in ortho-position which represents methyl.

5. The compound according to claim 1, wherein said compound is of Formula (B-1) or of Formula (B-2):

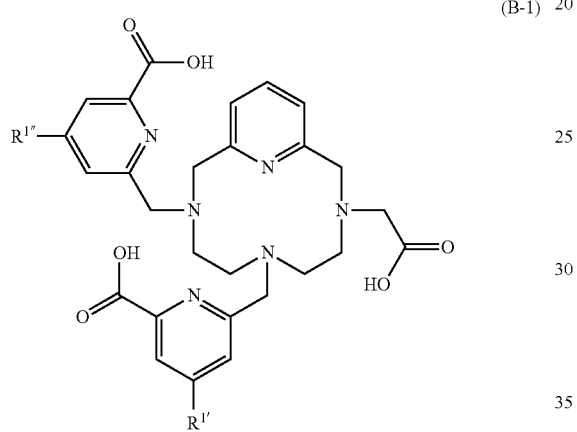

(B-1)

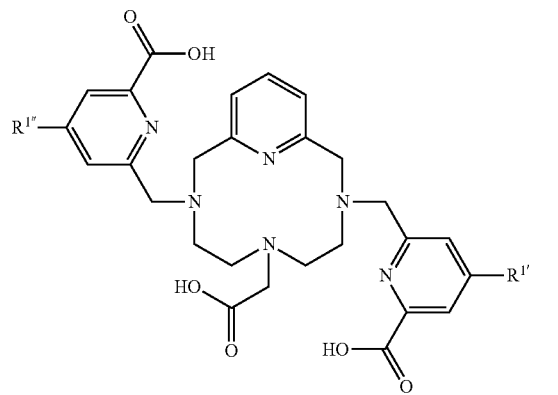

(B-2)

or a carboxylate salt thereof;

wherein $R^{1'}$ and $R^{1'''}$ each represents independently $R^1$ as defined in claim 1.

6. The compound according to claim 5, wherein said compound is of Formula (C-1) or of Formula (C-2):

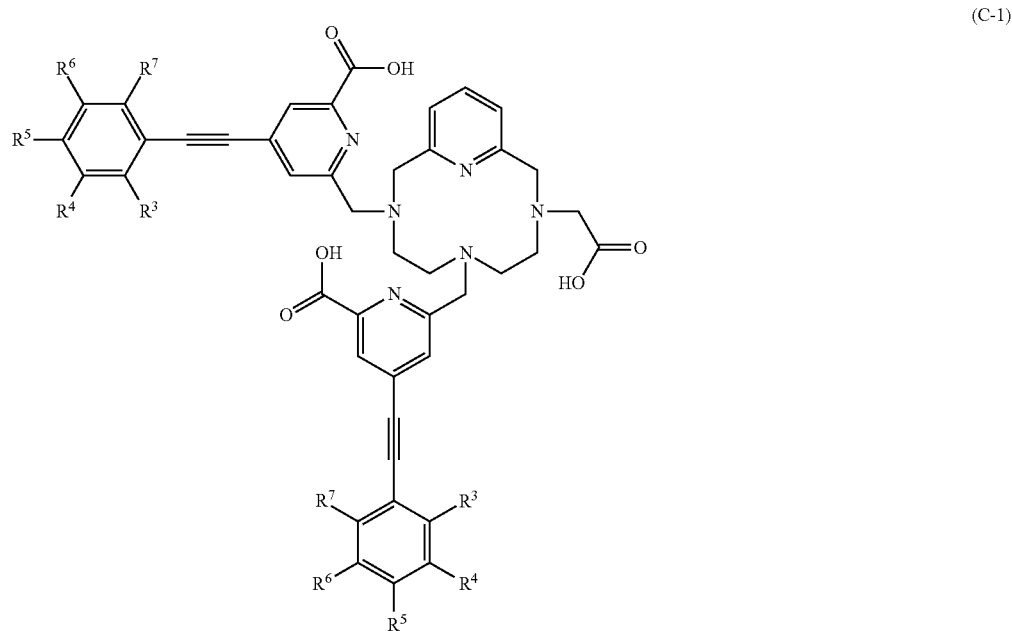

(C-1)

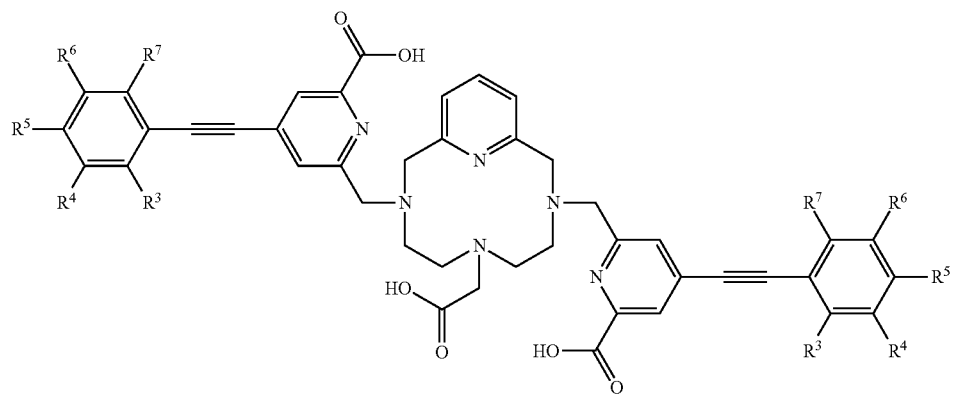

(C-2)

or a carboxylate salt thereof;

wherein $R^3$, $R^4$, $R^6$, and $R^7$ independently represent hydrogen or alkyl; and $R^5$ represent —O-polyether or —NRR', wherein R and R' represents independently polyether.

7. The compound according to claim 5, wherein said compound is of Formula (C-3) or of Formula (C-4):

wherein $R^8$, $R^9$, $R^{11}$, and $R^{12}$ independently represent hydrogen or alkyl; and $R^{10}$ represents —O-polyether.

8. The compound according to claim 1, wherein said compound is a triple potassium carboxylate salt of a compound of Formula (A).

(C-3)

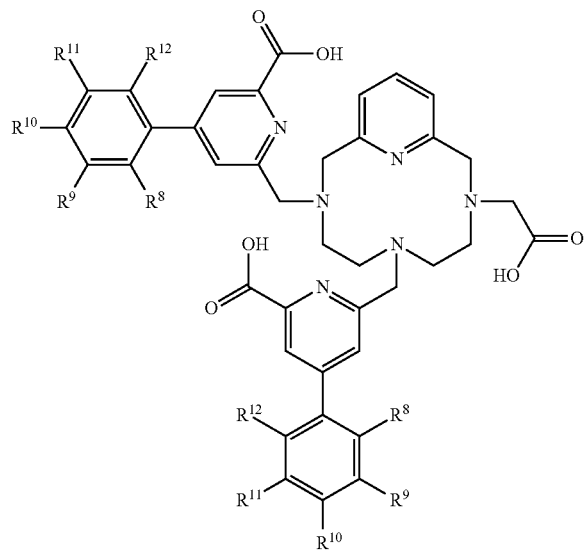

(C-4)

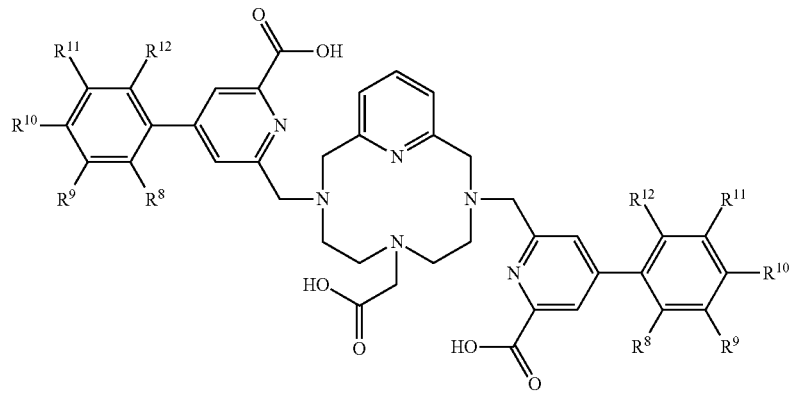

or a carboxylate salt thereof;

9. The compound according to claim 1, wherein the polyether in said chromophore group is a polyethylene glycol (PEG).

10. The compound according to claim 1, wherein $L^1$, $L^2$ and $L^3$ each independently represents a single bond; or a linker selected from alkyl, arylalkyl, heteroalkyl, heteroaryl, heteroarylalkyl, alkylheteroaryl, alkenyl, and alkynyl; said linker optionally additionally comprising a coupling product through which $X^1$, $X^2$ and $X^3$ are bounded to $L^1$, $L^2$ and $L^3$ respectively.

11. The compound according to claim 1, wherein said compound is selected from:

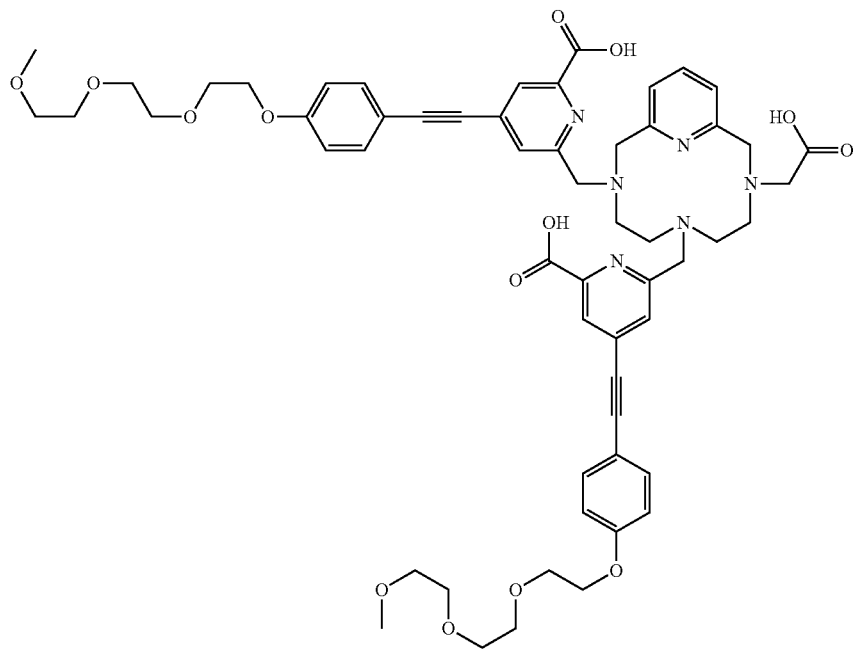

A1

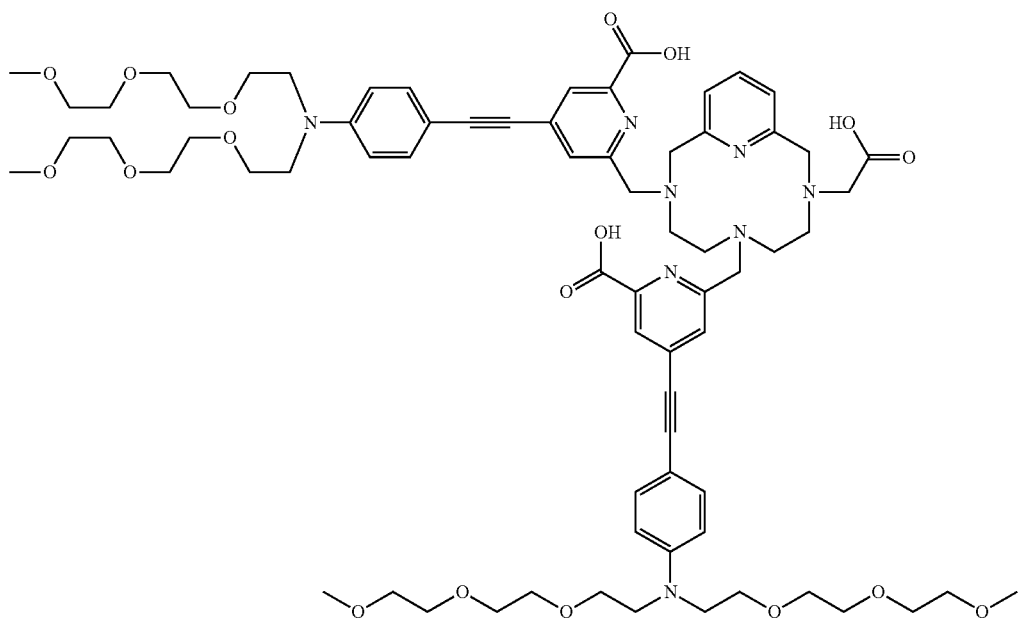

A2

-continued

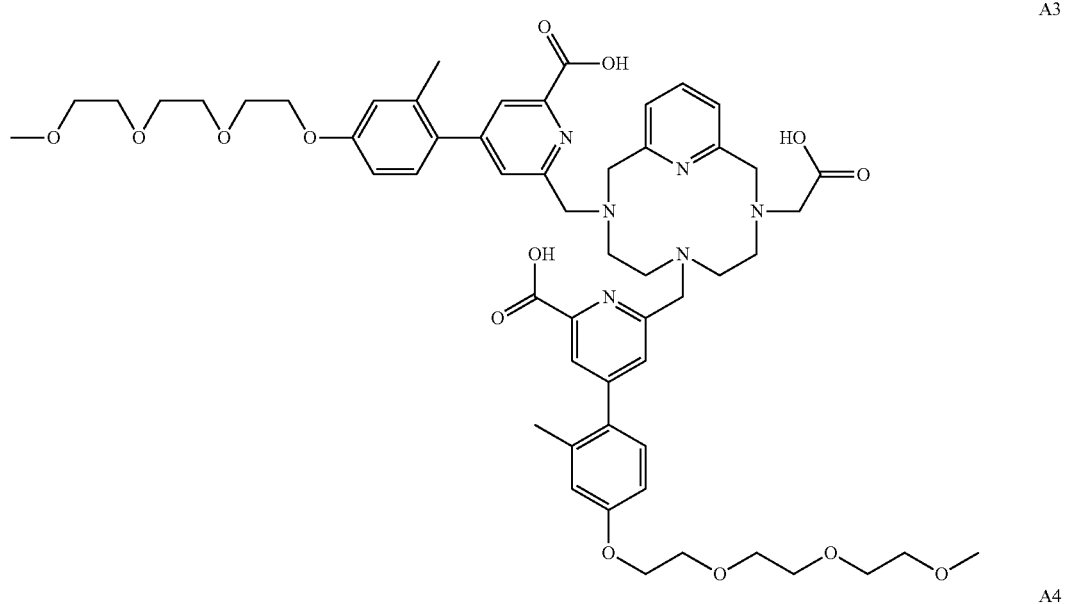

A3

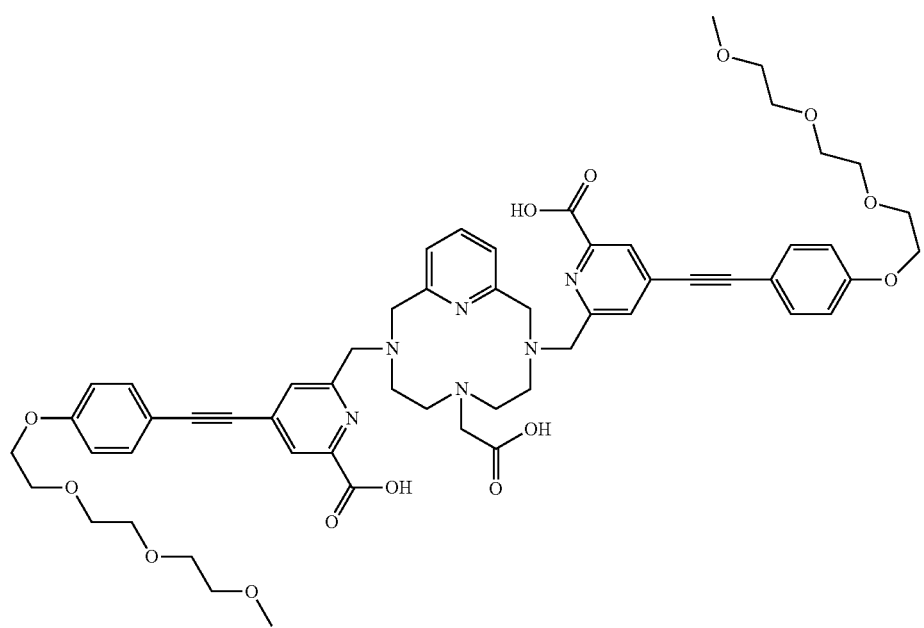

A4 and carboxylate salts thereof.

12. A chelate resulting from the complexation of a compound according to claim 1 with a lanthanide cation selected from neodymium (III), samarium (III), europium (III), terbium (III), dysprosium (III), erbium (III), and ytterbium (III).

13. A pharmaceutical composition comprising the chelate according to claim 12, in association with at least one pharmaceutically acceptable excipient.

14. A process for manufacturing a chelate from the complexation of a compound according to claim 1 comprising a step of contacting the compound with a lanthanide cation selected from neodymium (III), samarium (III), europium (III), terbium (III), dysprosium (III), erbium (III), and ytterbium (III).

15. A compound of Formula (E):

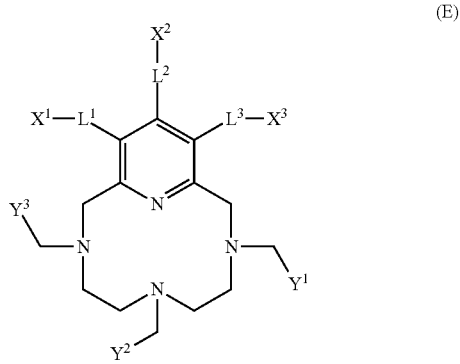

(E)

wherein
Y¹, Y² and Y³ each independently represents —COOR$^E$ or a picolinate ester of Formula (i-E):

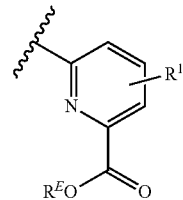
(i-E)

wherein each R$^E$ independently represents alkyl; and
each R¹ independently represents a chromophore group of Formula (ii) as defined in claim 1 or a chromophore group of Formula (iii) as defined in claim 1;
provided that at least two among Y¹, Y² and Y³ represents a picolinate ester of Formula (i-E); and
L¹, L², L³, X¹, X², and X³ are as defined in claim 1.

16. A method of in vitro biological imaging comprising:
a step of treatment of a biological sample with a chelate according to claim 12, and then
a step of analysis of said biological sample by an imaging method.

17. A method of in vivo biological imaging comprising:
a step of administration of a chelate according to claim 12 to a subject, and then
a step of analysis of an organ and/or tissue of said subject by an imaging method.

* * * * *